(12) United States Patent
Larson et al.

(10) Patent No.: US 12,378,598 B2
(45) Date of Patent: *Aug. 5, 2025

(54) DIGITAL ANALYTE ANALYSIS

(71) Applicant: Bio-Rad Laboratories, Inc., Hercules, CA (US)

(72) Inventors: Jonathan William Larson, Chelsea, MA (US); Qun Zhong, Lexington, MA (US); Darren Roy Link, Lafayette, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/465,623

(22) Filed: Sep. 12, 2023

(65) Prior Publication Data
US 2024/0002910 A1 Jan. 4, 2024

Related U.S. Application Data

(63) Continuation of application No. 17/574,780, filed on Jan. 13, 2022, which is a continuation of application
(Continued)

(51) Int. Cl.
*C12Q 1/6816* (2018.01)
*C12Q 1/6827* (2018.01)
(Continued)

(52) U.S. Cl.
CPC ......... *C12Q 1/6816* (2013.01); *C12Q 1/6827* (2013.01); *C12Q 1/686* (2013.01);
(Continued)

(58) Field of Classification Search
None
See application file for complete search history.

(56) References Cited

U.S. PATENT DOCUMENTS 6,171,850 B1 1/2001 Nagle et al.
6,323,040 B1 11/2001 Raz et al.
(Continued)

FOREIGN PATENT DOCUMENTS

WO  WO-2008143646 A2 * 11/2008 ........ B01L 3/502784
WO  2009059430 A1    5/2009
(Continued)

OTHER PUBLICATIONS

Vogelstein & Kinzler, Digital PCR, Proc Natl Acad Sci USA. Aug. 3, 1999;96(16):9236-41. doi: 10.1073/pnas.96.16.9236.*
(Continued)

*Primary Examiner* — Aaron A Priest
*Assistant Examiner* — Tian Nmn Yu
(74) *Attorney, Agent, or Firm* — Thomas C. Meyers; Sullivan & Worcester LLP

(57) ABSTRACT

The invention generally relates to droplet based digital PCR and methods for analyzing a target nucleic acid using the same. In certain embodiments, methods of the invention involve forming sample droplets containing, on average, a single target nucleic acid, amplifying the target in the droplets, excluding droplets containing amplicon from the target and amplicon from a variant of the target, and analyzing target amplicons.

13 Claims, 40 Drawing Sheets
Specification includes a Sequence Listing.

Related U.S. Application Data

No. 15/688,250, filed on Aug. 28, 2017, now Pat. No. 11,254,968, which is a continuation of application No. 15/019,355, filed on Feb. 9, 2016, now Pat. No. 9,745,617, which is a continuation of application No. 13/773,868, filed on Feb. 22, 2013, now Pat. No. 9,441,266, which is a continuation of application No. 13/026,120, filed on Feb. 11, 2011, now Pat. No. 9,074,242.

(60) Provisional application No. 61/388,937, filed on Oct. 1, 2010, provisional application No. 61/347,158, filed on May 21, 2010, provisional application No. 61/331,490, filed on May 5, 2010, provisional application No. 61/304,163, filed on Feb. 12, 2010.

(51) Int. Cl.
*C12Q 1/686* (2018.01)
*C12Q 1/6883* (2018.01)
*C12Q 1/6886* (2018.01)

(52) U.S. Cl.
CPC ......... *C12Q 1/6883* (2013.01); *C12Q 1/6886* (2013.01); *C12Q 2600/172* (2013.01)

(56) References Cited

U.S. PATENT DOCUMENTS

| | | | |
|---|---|---|---|
| 6,960,437 B2 | 11/2005 | Enzelberger et al. | |
| 7,118,910 B2 | 10/2006 | Unger et al. | |
| 9,127,310 B2 | 9/2015 | Larson | |
| 9,222,128 B2 | 12/2015 | Saxonov | |
| 9,222,132 B2 | 12/2015 | Drmanac | |
| 9,366,632 B2 | 6/2016 | Link | |
| 9,399,797 B2 | 7/2016 | Hutchison | |
| 9,494,520 B2 | 11/2016 | Link | |
| 9,745,617 B2 | 8/2017 | Larson | |
| 10,166,522 B2 | 1/2019 | Hindson | |
| 10,612,081 B2 | 4/2020 | Hutchison | |
| 11,254,968 B2 | 2/2022 | Larson | |
| 12,031,175 B2 | 7/2024 | Larson | |
| 2003/0083276 A1 | 5/2003 | Li et al. | |
| 2004/0180346 A1* | 9/2004 | Anderson | C07D 473/34 435/6.1 |
| 2005/0129582 A1 | 6/2005 | Breidford et al. | |
| 2006/0032746 A1 | 2/2006 | Knott et al. | |
| 2007/0003442 A1 | 1/2007 | Link et al. | |
| 2007/0052781 A1 | 3/2007 | Fraden et al. | |
| 2007/0065823 A1 | 3/2007 | Dressman et al. | |
| 2007/0202525 A1* | 8/2007 | Quake | C12Q 1/6883 435/6.12 |
| 2008/0003142 A1 | 1/2008 | Link et al. | |
| 2008/0014589 A1 | 1/2008 | Link et al. | |
| 2008/0023330 A1 | 1/2008 | Viovy et al. | |
| 2008/0241830 A1* | 10/2008 | Vogelstein | C12Q 1/6886 435/6.12 |
| 2009/0029478 A1* | 1/2009 | Puskas | C12P 19/34 436/94 |
| 2009/0053719 A1* | 2/2009 | Lo | C12Q 1/6851 435/6.11 |
| 2009/0069194 A1* | 3/2009 | Ramakrishnan | C12Q 1/6851 435/6.12 |
| 2009/0087847 A1* | 4/2009 | Lo | G16B 20/00 435/6.12 |
| 2009/0239308 A1* | 9/2009 | Dube | C12Q 1/6837 435/288.7 |
| 2010/0003687 A1 | 1/2010 | Simen et al. | |
| 2010/0022414 A1 | 1/2010 | Link et al. | |
| 2010/0055677 A1* | 3/2010 | Colston, Jr. | C12Q 1/04 435/7.1 |
| 2010/0069250 A1* | 3/2010 | White, III | C12Q 1/6851 435/6.19 |
| 2010/0105112 A1 | 4/2010 | Merton et al. | |
| 2010/0137163 A1 | 6/2010 | Link et al. | |
| 2010/0173394 A1 | 7/2010 | Colston et al. | |
| 2010/0273173 A1 | 10/2010 | Hirai | |
| 2010/0273219 A1 | 10/2010 | May et al. | |
| 2010/0304978 A1* | 12/2010 | Deng | C12Q 1/6879 435/6.12 |
| 2011/0159499 A1 | 6/2011 | Hindson et al. | |
| 2011/0250597 A1 | 10/2011 | Larson et al. | |
| 2012/0164633 A1 | 6/2012 | Laffler | |
| 2012/0190032 A1 | 7/2012 | Ness et al. | |
| 2012/0208724 A1 | 8/2012 | Steemers et al. | |
| 2012/0220494 A1 | 8/2012 | Samuels et al. | |
| 2012/0258516 A1 | 10/2012 | Schultz et al. | |
| 2012/0288857 A1 | 11/2012 | Livak | |
| 2012/0289414 A1 | 11/2012 | Mitra et al. | |
| 2012/0329050 A1 | 12/2012 | Nadeau et al. | |
| 2013/0022973 A1* | 1/2013 | Hansen | C12Q 1/6851 435/6.11 |
| 2013/0099018 A1 | 4/2013 | Miller et al. | |
| 2013/0116130 A1 | 5/2013 | Fu et al. | |
| 2013/0261196 A1 | 10/2013 | Diamond et al. | |
| 2016/0194700 A1 | 7/2016 | Edwards | |
| 2024/0002910 A1 | 1/2024 | Larson | |
| 2024/0132939 A1 | 4/2024 | Larson | |

FOREIGN PATENT DOCUMENTS

| | | |
|---|---|---|
| WO | 2010151776 A2 | 12/2010 |
| WO | 2012022976 A1 | 2/2012 |
| WO | 2012048341 A1 | 4/2012 |
| WO | 2012083225 A2 | 6/2012 |

OTHER PUBLICATIONS

Kiss et al, High-throughput quantitative polymerase chain reaction in picoliter droplets, Anal Chem. Dec. 1, 2008;80(23):8975-81. doi: 10.1021/ac801276c.*

Reichman, Jay. "Handbook of optical filters for fluorescence microscopy." Chroma Technology Corporation (2000) (Year: 2000).*

Sapsford et al. Materials for fluorescence resonance energy transfer analysis: beyond traditional donor-acceptor combinations. Angew Chem Int Ed Engl. Jul. 10, 2006;45(28):4562-89. doi: 10.1002/anie. 200503873. PMID: 16819760. (Year: 2006).*

Kiss et al, High-throughput quantitative polymerase chain reaction in picoliter droplets, Anal Chem. Dec. 1, 2008;80(23):8975-81. doi: 10.1021/ac801276c (Year: 2008).*

Baker, M. Clever PCR: more genotyping, smaller volumes. Nature Methods 7:351-56 (2010).

BioRad, Droplet Digital PCR Applications Guide, Feb. 1, 2010.

Kiss et al., High-throughput quantitative polymerase chain reaction in picoliter droplets, Anal Chem 80(23):8975-81 (2008).

Vogelstein & Kinzler, Digital PCR, Proc Nat'l Acad Sci USA 3:96(16):9236-41 (1999).

Hindson, B.J., et al., "High-Throughput Droplet Digital PCR System for Absolute Quantitation of DNA Copy Number", Hindson, B.J., et al., "High-Throughput Droplet Digital PCR System for Absolute Quantitation of DNA Copy Number" Anal. Chem. (2011) 83:8604-8610, 2011, 8604-8610.

Tewhey, Tewhey, 2009, Microdroplet-based PCR enrichment for larg-scale targeted sequencing, Nat Biotech 27 (11):1025-1031.

Birtwell, 2020, Microparticle encoding technologies for high-throughput multiplexed suspension assays, Integ Bio 5-6 (1):345-62.

Han et al., 2001, Quantum-dot-tagged microbeads for multiplexed optical coding of biomolecules, Nat Biotech 19 (7):631-35.

Li et al, 2009, Sensitive digital quantification of DNA methylation in clinical samples, Nat Biotech 27(9):858-63.

Morgan, 2004, Cytometric bead array: a multiplexed assay platform with applications in various areas of biology, Elsevier 110(3):252-66.

Pekin et al., 2010, Droplet-based microfluidics for the quantitative detection of rare mutations, 14th Int Conf on Mini Systems for Chem and Life Sci, (1):58-60.

(56) References Cited

OTHER PUBLICATIONS

Reichman, 2000, Handbook of optical filters for fluorescence microscopy, Chroma Tech Corp.
Sapsford et al., 2006, Materials for fluorescence resonance energy transfer analysis: beyond traditional donor-acceptor combinations, Angew Chem Int Ed Engl 45(28):4562-89.
Yeung, 2008, Fluorescence energy transfer-labeled primers for high-performance forensic DNA profiling, Electrophoresis (29):2251-59.
Fan, 2007, Detection of aneuploidy with digital polymerase chain reaction, Anal Chem 79:75767579.
Huang, 2007, Identification of 8 foodborne pathogens by multicolor combinational probe coding technology in a single realtime PCR, Clin Chem 53(10):17418.
Kiss, 2008, High throughput quantitative polymerase chain reaction in picoliter droplets, Anal Chem 80(23):897581.
Li, 2009, Sensitive digital quantificaiton of DNA methylation in clinical samples, Nat Biotech 27(9):85863.
Sapsford, 2006, Materials for fluorescence resonance energy transfer analysis, Angew Chem Int Ed Engl 45 (28):456289.

* cited by examiner

- Mixture of multiple primers and probes
- 5 Taqman Assays in each droplet
  - Expression Analysis
  - Precise Quantification of copy number
  - Requires 1/5 the DNA of 5 opti-plex reactions
- Each reaction has a unique location in 2D scatter plot

- Off-axis populations are generated by making blends of probes
- Expands optical space available for multiplexing assays

One Color One Target

Single molecule amplification produces of fluorescence burst of a quantized intensity.

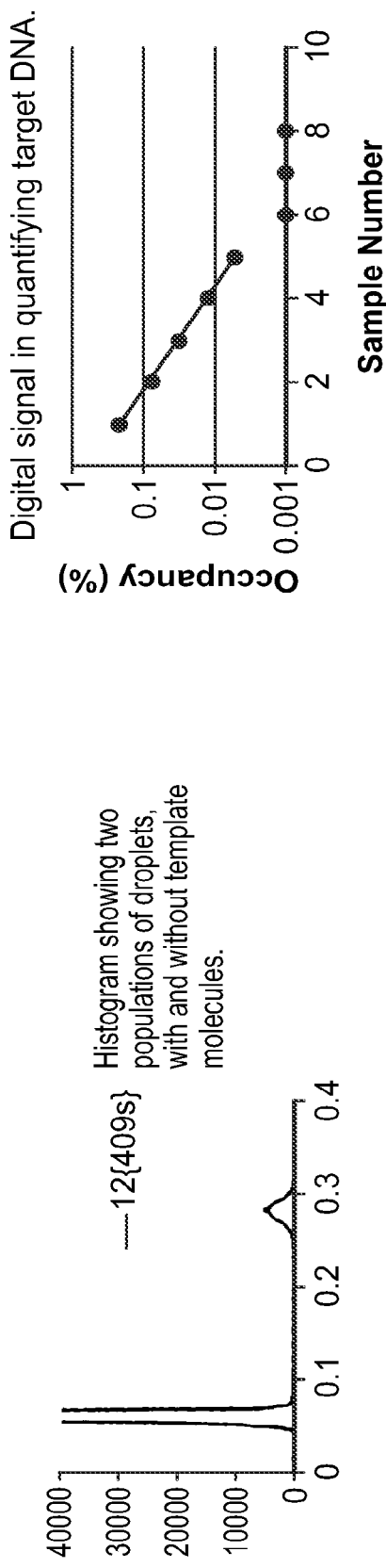
FIG. 7D  Histogram showing two populations of droplets, with and without template molecules.
FIG. 7E
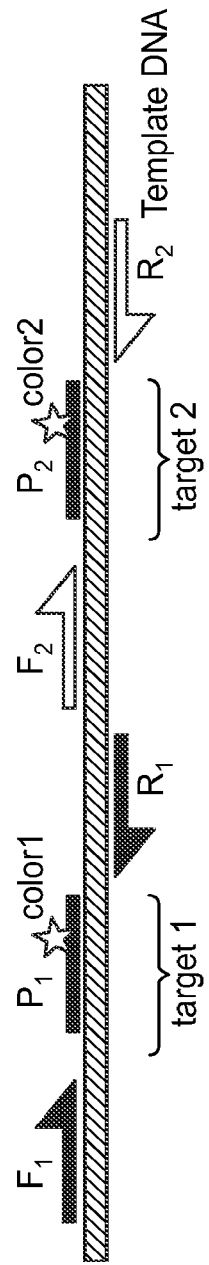
FIG. 8A  Two Colors Two Targets

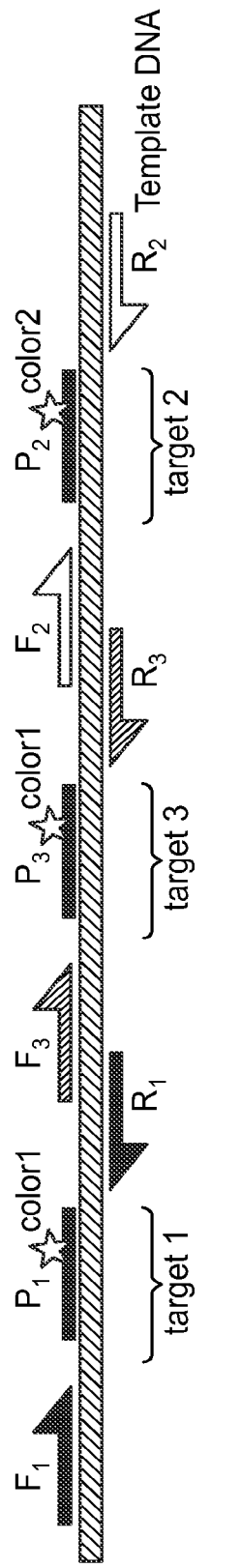
FIG. 9A  Two Colors THREE Targets
FIG. 9B  Single molecule amplification produces of fluorescence burst of a quantized intensity. Laser spot Histogram showing four populations of droplets: with target1, with target2, with target3 and without any of the three targets.

FIG. 12A

Tuning the Intensity of Target 2

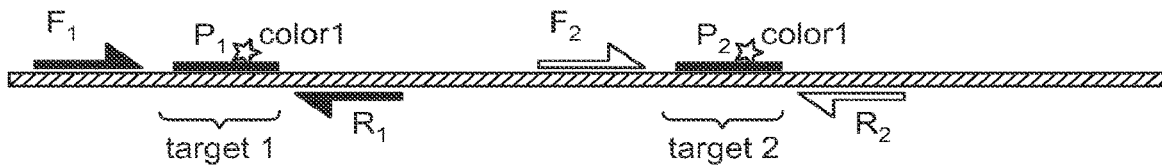

Probe 2 has a single base missmatch to target two and will produce a digital readout of lower signal intensity

FIG. 12B

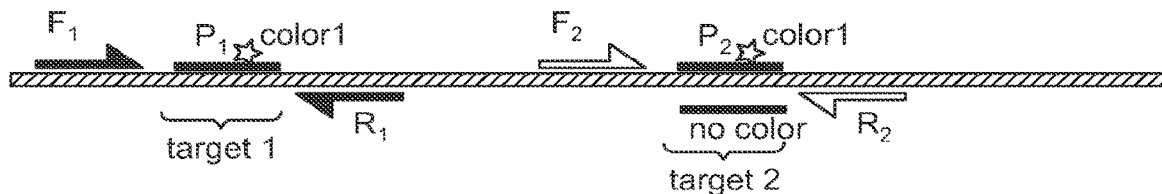

Probe 2 is a blend of identical probes doth with and without a fluorophore to reduce the overall intensity of the fluorescent signal

FIG. 12C

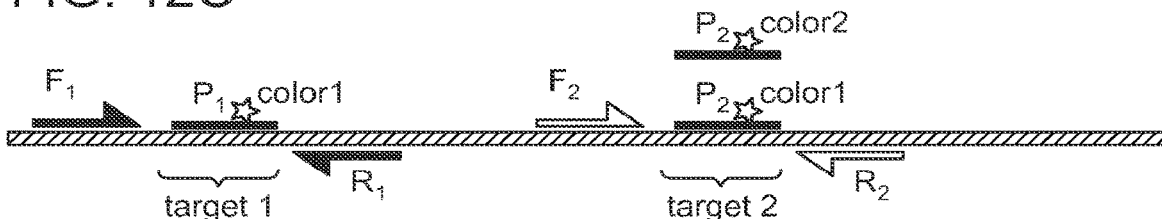

Probe 2 is a blend of identical probes each with a different color fluorophore to produce a multi-color fluorescent burst.

Relative intensity of signals from multiple targets of the same color can be generated in a variety of ways. Examples include: FIG.12A) using a single base missmatch of the probe and target to distinguish different targets. FIG.12B) blend identical probes with and without fluorophores. FIG.12C) blend identical probes with two or more different color fluorophores.

SEQUENCE LISTING

```
Sequence total quantity: 14
SEQ ID NO: 1             moltype = DNA  length = 27
FEATURE                  Location/Qualifiers
misc_feature             1..27
                         note = Synthetic oligonucleotide
source                   1..27
                         mol_type = other DNA
                         organism = synthetic construct
SEQUENCE: 1
aatgcttttt aacatccata taaagct                                      27

SEQ ID NO: 2             moltype = DNA  length = 25
FEATURE                  Location/Qualifiers
misc_feature             1..25
                         note = Synthetic oligonucleotide
source                   1..25
                         mol_type = other DNA
                         organism = synthetic construct
SEQUENCE: 2
ccttaattta aggaatgtga gcacc                                        25

SEQ ID NO: 3             moltype = DNA  length = 16
FEATURE                  Location/Qualifiers
misc_feature             1..16
                         note = Synthetic oligonucleotide
source                   1..16
                         mol_type = other DNA
                         organism = synthetic construct
SEQUENCE: 3
```

```
cagggtttca gacaaa                                                           16

SEQ ID NO: 4              moltype = DNA  length = 27
FEATURE                   Location/Qualifiers
misc_feature              1..27
                          note = Synthetic oligonucleotide
source                    1..27
                          mol_type = other DNA
                          organism = synthetic construct
SEQUENCE: 4
aatgctttt aacatccata taaagct                                                27

SEQ ID NO: 5              moltype = DNA  length = 25
FEATURE                   Location/Qualifiers
misc_feature              1..25
                          note = Synthetic oligonucleotide
source                    1..25
                          mol_type = other DNA
                          organism = synthetic construct
SEQUENCE: 5
ccttaattta aggaatgtga gcacc                                                 25

SEQ ID NO: 6              moltype = DNA  length = 18
FEATURE                   Location/Qualifiers
misc_feature              1..18
                          note = Synthetic oligonucleotide
source                    1..18
                          mol_type = other DNA
                          organism = synthetic construct
SEQUENCE: 6
tgattttgtc taaaaccc                                                         18

SEQ ID NO: 7              moltype = DNA  length = 24
FEATURE                   Location/Qualifiers
misc_feature              1..24
                          note = Synthetic oligonucleotide
source                    1..24
                          mol_type = other DNA
                          organism = synthetic construct
SEQUENCE: 7
caacctactc ttctcagacg tgta                                                  24

SEQ ID NO: 8              moltype = DNA  length = 23
FEATURE                   Location/Qualifiers
misc_feature              1..23
                          note = Synthetic oligonucleotide
source                    1..23
                          mol_type = other DNA
                          organism = synthetic construct
SEQUENCE: 8
tcgaagtgat ccagtgggta gtg                                                   23

SEQ ID NO: 9              moltype = DNA  length = 21
FEATURE                   Location/Qualifiers
misc_feature              1..21
                          note = Synthetic oligonucleotide
source                    1..21
                          mol_type = other DNA
                          organism = synthetic construct
SEQUENCE: 9
caggagatgc ccgcccagct c                                                     21

SEQ ID NO: 10             moltype = DNA  length = 25
FEATURE                   Location/Qualifiers
misc_feature              1..25
                          note = Synthetic oligonucleotide
source                    1..25
                          mol_type = other DNA
                          organism = synthetic construct
SEQUENCE: 10
tgctgatgct ttgggaagta tgtta                                                 25
```

```
SEQ ID NO: 11          moltype = DNA  length = 18
FEATURE                Location/Qualifiers
misc_feature           1..18
                       note = Synthetic oligonucleotide
source                 1..18
                       mol_type = other DNA
                       organism = synthetic construct
SEQUENCE: 11
catgagtggc tatcatac                                                     18

SEQ ID NO: 12          moltype = DNA  length = 25
FEATURE                Location/Qualifiers
misc_feature           1..25
                       note = Synthetic oligonucleotide
source                 1..25
                       mol_type = other DNA
                       organism = synthetic construct
SEQUENCE: 12
tgtcaggaaa agatgctgag tgatt                                             25

SEQ ID NO: 13          moltype = DNA  length = 17
FEATURE                Location/Qualifiers
misc_feature           1..17
                       note = Synthetic oligonucleotide
source                 1..17
                       mol_type = other DNA
                       organism = synthetic construct
SEQUENCE: 13
atgagtggct gtcatac                                                      17

SEQ ID NO: 14          moltype = DNA  length = 18
FEATURE                Location/Qualifiers
misc_feature           1..18
                       note = Synthetic oligonucleotide
source                 1..18
                       mol_type = other DNA
                       organism = synthetic construct
SEQUENCE: 14
catgagtggc tgtcatac                                                     18
```

DIGITAL ANALYTE ANALYSIS

SEQUENCE LISTING

This application contains a sequence listing which has been submitted in extensible Markup Language (XML) format via the Patent Center and is hereby incorporated by reference in its entirety. The XML-formatted sequence listing, created on Jun. 27, 2025, is named RDT-548US-17CON3_ST26.xml and is 18,823 bytes in size.

FIELD OF THE INVENTION

The invention generally relates to droplet based digital PCR and methods for analyzing a target nucleic acid using the same.

BACKGROUND

Assays have been developed that rely on analyzing nucleic acid molecules from bodily fluids for the presence of mutations, thus leading to early diagnosis of certain diseases such as cancer. In a typical bodily fluid sample however, any abnormal nucleic acids containing mutations of interest are often present in small amounts (e.g., less than 1%) relative to a total amount of nucleic acid in the bodily fluid sample. This can result in a failure to detect the small amount of abnormal nucleic acid due to stochastic sampling bias.

The advent of PCR and real-time PCR methodologies has greatly improved the analysis of nucleic acids from both throughput and quantitative perspectives. While traditional PCR techniques typically rely on end-point, and sometimes semi-quantitative, analysis of amplified DNA targets via agarose gel electrophoresis, real-time PCR (or qPCR) methods are geared toward accurately quantifying exponential amplification as the reaction progresses. qPCR reactions are monitored either using a variety of highly sequence specific fluorescent probe technologies, or by using non-specific DNA intercalating fluorogenic dyes.

As the need for higher throughput in analyzing multiple targets in parallel continues to escalate in the fields of genomics and genetics, and as the need for more efficient use of sample grows in medically related fields such as diagnostics, the ability to perform and quantify multiple amplifications simultaneously within the same reaction volume (multiplexing) is paramount for both PCR and qPCR. While end-point PCR can support a high level of amplicon multiplexing, such ample capacity for multiplexing probe-based qPCR reactions remains elusive for a number of reasons. For example, most commercial real-time thermal cyclers only support up to four differently colored fluorophores for detection as a consequence of the limited spectral resolution of common fluorophores, translating into a multiplexing capacity of 4×. Additionally, while optimization of single target primer/probe reactions is now standard practice, combining primers and probes for multiple reactions changes the thermodynamic efficiencies and/or chemical kinetics, necessitating potentially extensive troubleshooting and optimization. Very high multiplexing of greater than 100× has been demonstrated in a "one of many" detection format for pathogen identification using "sloppy" molecular beacons and melting points as fingerprints, however the approach is restricted to applications with a slim likelihood of the presence of multiple simultaneous targets. A half-multiplexing method achieved 19× in a two step reaction with general multiplexed preamplification in the first step, followed by separate single-plex quantitative PCR in the second step. However a general purpose single-pot solution to qPCR multiplexing does not yet exist.

Digital PCR (dPCR) is an alternative quantitation method in which dilute samples are divided into many separate reactions. See for example, Brown et al. (U.S. Pat. Nos. 6,143,496 and 6,391,559) and Vogelstein et al. (U.S. Pat. Nos. 6,440,706, 6,753,147, and 7,824,889), the content of each of which is incorporated by reference herein in its entirety. The distribution from background of target DNA molecules among the reactions follows Poisson statistics, and at so called "terminal dilution" the vast majority of reactions contain either one or zero target DNA molecules for practical intents and purposes. In another case, at so called "limiting dilution" some reactions contain zero DNA molecules, some reactions contain one molecule, and frequently some other reactions contain multiple molecules, following the Poisson distribution. It is understood that terminal dilution and limiting dilution are useful concepts for describing DNA loading in reaction vessels, but they have no formal mathematical definition, nor are they necessarily mutually exclusive. Ideally, at terminal dilution, the number of PCR positive reactions (PCR(+)) equals the number of template molecules originally present. At limiting dilution, Poisson statistics are used to uncover the underlying amount of DNA. The principle advantage of digital compared to qPCR is that it avoids any need to interpret the time dependence of fluorescence intensity—an analog signal—along with the main underlying uncertainty of non-exponential amplification during early cycles.

SUMMARY

The invention generally relates to the manipulation of nucleic acid in droplets, and in particular, nucleic acid amplification and detection. In one aspect, the invention provides a droplet that contains a single nucleic acid template and a plurality of primer pairs specific for multiple target sites on the template. The single nucleic acid template can be DNA (e.g., genomic DNA, cDNA, etc.) or RNA. The template is amplified in the droplet for detection; and may preferably be amplified using a plurality of primer pairs as described herein.

The ability to amplify and detect single nucleic acids in droplets enables digital PCR, detection, counting, and differentiation among nucleic acids, especially those present in heterogeneous samples. Thus, the invention applies to digital amplification techniques and, in specific embodiments enables multiplex PCR in droplets. For example, multiplexing primers in droplets enables the simultaneous increase in the number of PCR droplets while keeping the amount of input DNA the same or lower and generate the same or greater amplicon yield. This results in an overall increase in the amount of PCR positive droplets and amplicon yield without the consumption of more DNA. Even though the number of PCR primer pairs per droplet is greater than one, there is only one template molecule per droplet, and thus, in some implementations, there is only one primer pair per droplet that is being utilized at one time. As such, the advantages of droplet PCR for eliminating bias from either allele specific PCR or competition between different amplicons is maintained. However, as described below in relation to detection of haplotypes, other implementations advantageously allow detection of multiple loci on a single template using multiple primer pairs, preferably designed to minimize bias. Microfluidic droplets for multiplex analysis according to the invention contain a plurality of probes that hybridize to amplicons produced in the droplets. Preferably, the droplet contains two or more probes, e.g., 2, 3, 4, 5, 6, 7, 8, 9, 10, 12, 14, 16, 18, 20, 25, 30, 35, 40, 45, 50, 55, 60, 60, 75, 80, 85, 90, 95, 100, 110, 120, 130, 140, 150, 160, 170, 180, 190, 200, 500, or more probes. Certain members of the plurality of probes include a detectable label. Members of the plurality of probes can each include the same detectable label, or a different detectable label. The detectable label is preferably a fluorescent label. The plurality of probes can include one or more groups of probes at varying concentrations. The one or more groups of probes can include the same detectable label which will vary in intensity upon detection, due to the varying probe concentrations. The droplets of the invention can further contain one or more reagents for conducting a polymerase chain reaction, such as a DNA or RNA polymerase, and/or dNTPs.

The present invention additionally relates to a method for detecting a plurality of targets in a biological sample using digital PCR in microfluidic droplets. The sample may be a human tissue or body fluid. Exemplary body fluids pus, sputum, semen, urine, blood, saliva, and cerebrospinal fluid.

One or more droplets are formed, each containing a single nucleic acid template and a heterogeneous mixture of primer pairs and probes, each specific for multiple target sites on the template. For example, a first fluid (either continuous, or discontinuous as in droplets) containing a single nucleic acid template (DNA or RNA) is merged with a second fluid (also either continuous, or discontinuous as in droplets) containing a plurality of primer pairs and a plurality of probes, each specific for multiple targets sites on the nucleic acid template to form a droplet containing the single nucleic acid template and a heterogeneous mixture of primer pairs and probes. The second fluid can also contain reagents for conducting a PCR reaction, such as a polymerase and dNTPs.

Certain members of the plurality of probes include a detectable label. Members of the plurality of probes can each include the same detectable label, or a different detectable label. The detectable label is preferably a fluorescent label. The plurality of probes can include one or more groups of probes at varying concentrations. The one or more groups of probes can include the same detectable label which varies in intensity upon detection, due to the varying probe concentrations.

The first and second fluids can each be in droplet form. Any technique known in the art for forming droplets may be used with methods of the invention. An exemplary method involves flowing a stream of the sample fluid containing the nucleic acid template such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets containing the first fluid. The carrier fluid may be any fluid that is immiscible with the sample fluid. An exemplary carrier fluid is oil. In certain embodiments, the carrier fluid includes a surfactant, such as a fluorosurfactant. The same method may be applied to create individual droplets from the second fluid containing the primer pairs (and, in some implementations, the amplification reagents). Either the droplets containing the first fluid, the droplets containing the second fluid, or both, may be formed and then stored in a library for later merging, aspects of certain implementations of which are described in U.S. patent application Ser. No. 12/504,764, hereby incorporated herein in its entirety for all purposes. Once formed, droplets containing the first and second fluids can be merged to form single droplets containing the single nucleic acid template and heterogeneous mixture of primer pairs and probes. Merging can be accomplished, for example, in the presence of an electric field. Moreover, it is not required that both fluids be in the form of droplets when merging takes places. One exemplary method for merging of fluid portions with droplets is taught, for example, in co-pending U.S. Patent Application No. 61/441,985, filed on even date herewith.

The nucleic acid template in each of the merged/formed droplets is amplified, e.g., by thermocycling the droplets under temperatures/conditions sufficient to conduct a PCR reaction. The resulting amplicons in the droplets can then be analyzed. For example, the presence of absence of the plurality of targets in the one or more droplets is detected optically, e.g., by the detectable label on the plurality of probes.

The invention further relates to methods for analyzing a target nucleic acid. More particularly, methods of the invention are able to detect polymerase errors that occur during a PCR reaction and are able to exclude from analysis amplification products that are a result of a polymerase error. Methods of the invention are particularly useful in digital PCR where a polymerase error may result in a partitioned section of sample being incorrectly identified as containing a mutant allele, i.e., a false positive. Such false positives greatly impact the validity and precision of digital PCR results. Methods of the invention are able to uniquely detect multiple targets with the same optical color. Methods of the invention are particularly useful in digital PCR where it is desirable to identify multiple different target molecules that may be present in the starting test fluid.

Methods of the invention involve forming sample droplets containing target nucleic acid. Ideally, methods of the invention comprise forming droplets for digital PCR. Preferred digital PCR droplets contain one copy of a nucleic acid to be amplified, although they may contain multiple copies of the same nucleic acid sequence. Any technique known in the art for forming sample droplets may be used with methods of the invention. One exemplary method involves flowing a stream of sample fluid including nucleic acids such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets. The carrier fluid may be any fluid that is immiscible with the sample fluid. An exemplary carrier fluid is oil. In certain embodiments, the carrier fluid includes a surfactant, such as a fluorosurfactant.

The targets are then amplified in the droplets. Any method known in the art may be used to amplify the target nucleic acids either linearly or exponentially. A preferred method is the polymerase chain reaction (PCR). For purposes of the invention, any amplification technique commonly known in the art may be implemented such as rolling circle amplification, isothermal amplification, or any combination of amplification methods using loci specific primers, nested-primers, or random primers (such primers, and/or primers used for PCR, are included in the term "amplification reagents"). Once amplified, droplets containing amplicon from the target and amplicon from a variant of the target are excluded. One method to exclude droplets that contain a heterogeneous population of amplicons from droplets that contain a homogeneous population of amplicons includes hybridizing detectably-labeled probes to the amplicons, flowing the droplets through a microfluidic channel, and excluding those droplets in which both amplicon from the target and amplicon from a variant of the target are detected.

Once droplets containing a heterogeneous population of amplicons are excluded, droplets that contain a homogeneous population of amplicons are analyzed. Any analytical technique known in the art may be used. In certain embodiments, analyzing the droplets involves determining a number of droplets that contain only wild-type target, and determining a number of droplets that contain only a variant of the target. Generally, the presence of droplets containing only the variant is indicative of a disease, such as cancer. The variant may be an allelic variant. An exemplary allelic variant is a single nucleotide polymorphism. The variant may also be a specific haplotype. Haplotypes refer to the presence of two or more variants on the same nucleic acid strand. Haplotypes can be more informative or predictive than genotypes when used to determine such things as the presence or severity of disease, response to drug therapy or drug resistance of bacterial or viral infections. Because each droplet contains only one template strand it is an ideal vessel for the determination of haplotypes. The detection of two or more variants in a single droplet that contains a single intact nucleic acid strand identifies the haplotype of the variants on that strand. The presence of two or more markers in the same droplet can be identified by such methods as the presence of dyes of multiple colors or the increase in the intensity of a single dye or a combination of both. Any method that allows the identification of multiple variants in a single droplet enables the determination of a samples haplotype.

In accordance with some implementations of the invention, a method is provided for analyzing a target nucleic acid that includes compartmentalizing a first fluid into portions, each portion containing a single target nucleic acid; amplifying the target in the portions; excluding portions containing amplicon from the target and amplicon from a variant of the target; and analyzing target amplicons.

In other aspects, the invention generally provides methods for detecting a recurrence of a cancer in a patient. Those methods may involve forming sample droplets containing a single target nucleic acid derived from a patient sample, flowing the sample droplets through a channel, amplifying the target in the droplets, detecting amplified target in the droplets, excluding droplets including a heterogeneous population of amplicons, and analyzing non-excluded droplets to determine the presence of mutant alleles indicative of recurrence. In certain embodiments, the analyzing step includes capturing amplicon obtained from the droplets using labeled capture probes. The sample may be a human tissue or body fluid. Exemplary body fluids are pus, sputum, semen, urine, blood, saliva, stool, and cerebrospinal fluid. In other aspects of the invention generally provide a method for forensic identification of low levels of target nucleic acid in an environment having multiple other sources of nucleic acid. Such methods may also be practiced using fluids compartmentalized in containers other than or in addition to droplets.

BRIEF DESCRIPTION OF THE DRAWINGS

FIG. 3A depicts the droplet generation chip; FIG. 3B depicts the droplet spacing for readout; and FIG. 3C depicts a cartoon of droplet readout by fluorescence.

FIG. 4A shows droplet fluorescence during readout for the most concentrated sample. Each discrete burst of fluorescence corresponded to an individual droplet. Two different groups of droplets were evident: PCR(+) droplets peaking at .about.0.8 V and PCR(-) droplets at .about.0.1 V; FIG. 4B shows a histogram of the peak fluorescence intensities of droplets from the complete data trace in (a). PCR(+) and PCR(-) droplets appeared as two very distinct populations centered at 0.78 and 0.10 V, respectively; FIG. 4B shows the serial dilution of template DNA. Open circles: measured occupancies; solid line: the best fit to Eqn 2 (A=0.15, f=4.8, R.sup.2-0.9999).

FIGS. 7A-E are a schematic depicting one-color detection of a genetic sequence with a microfluidic device.

FIGS. 8A-D are a schematic depicting two-color detection of two genetic sequences with a microfluidic device.

FIGS. 9A-D are a schematic depicting two-color detection of three genetic sequences with a microfluidic device.

FIG. 11A depicts a histogram of droplet peak fluorescence intensities; FIG. 11B shows a comparison of gene copy numbers measured by monochromatic dPCR.

FIGS. 12A-C are a schematic for tuning the intensity of a detectable label to a particular target with a microfluidic device.

FIG. 14A is a 2D histogram of droplet fluorescence intensities, shown as a heat map, for the 5-plex assay against the synthetic model chromosome for validation. The six well resolved droplet populations corresponded to the five individual assays plus the empty droplets; FIG. 14B shows the results of the SMA pilot study.

FIG. 15 shows 2-D histograms of droplet fluorescence intensity, shown as heat maps with hotter colors representing higher droplet counts, for the 9-plex assay against the synthetic model chromosome (left panel=Before optimization; right panel=After optimization).

DETAILED DESCRIPTION

Figure 1:
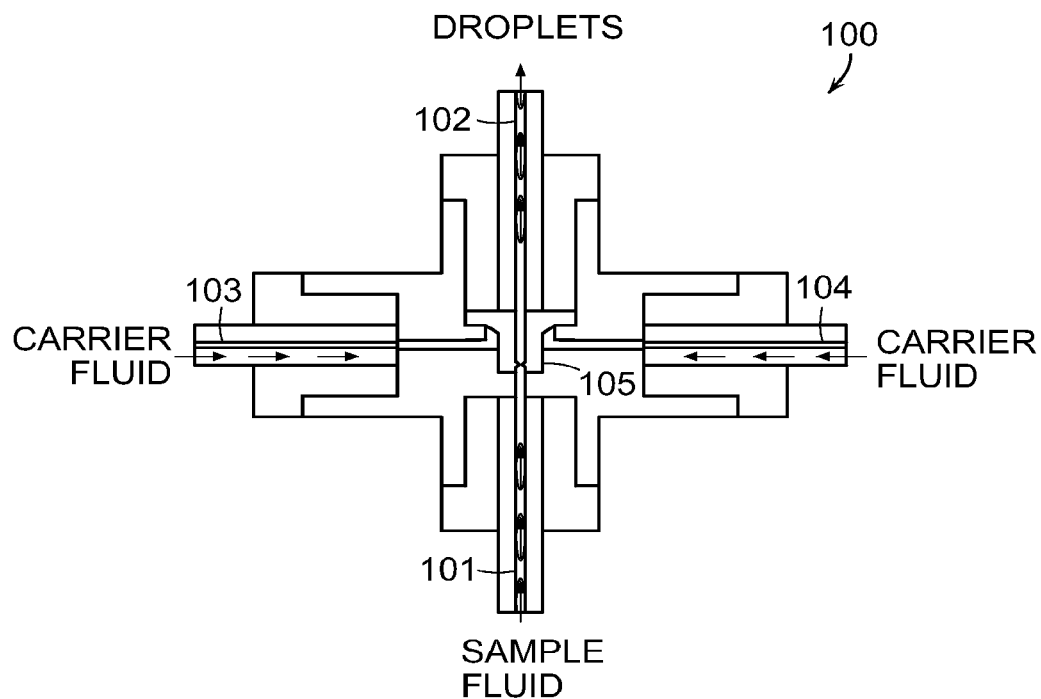
FIG. 1 depicts a droplet formation device.

The invention provides materials and methods for analysis of biomolecules. In one aspect, the invention provides for digital analysis in droplets, such as microfluidic droplets. The invention allows digital PCR to be conducted and provides for significantly reduced or eliminated errors.

Ideally, the sensitivity of digital PCR is limited only by the number of independent amplifications that can be analyzed, which has motivated the development of several ultra-high throughput miniaturized methods allowing millions of single molecule PCR reactions to be performed in parallel (discussed in detail elsewhere). In a preferred embodiment of the invention, digital PCR is performed in aqueous droplets separated by oil using a microfluidics system. In another preferred embodiment, the oil is a fluorinated oil such as the Fluorinert oils (3M). In a still more preferred embodiment the fluorinated oil contains a surfactant, such as PFPE-PEG-PFPE triblock copolymer, to stabilize the droplets against coalescence during the amplification step or at any point where they contact each other. Microfluidic approaches allow the rapid generation of large numbers (e.g. $10^6$ or greater) of very uniformly sized droplets that function as picoliter volume reaction vessels (see reviews of droplet-based microfluidics). But as will be described, the invention is not limited to dPCR performed in water-in-oil emulsions, but rather is general to all methods of reaction compartmentalization for dPCR. In the description that follows, the invention is described in terms of the use of droplets for compartmentalization, but it is understood that this choice of description is not limiting for the invention, and that all of the methods of the invention are compatible with all other methods of reaction compartmentalization for dPCR.

Methods of the invention involve novel strategies for performing multiple different amplification reactions on the same sample simultaneously to quantify the abundance of multiple different DNA targets, commonly known to those familiar with the art as "multiplexing". Methods of the invention for multiplexing dPCR assays promise greater plexity—the number of simultaneous reactions—than possible with existing qPCR or dPCR techniques. It is based on the singular nature of amplifications at terminal or limiting dilution that arises because most often only a single target allele is ever present in any one droplet even when multiple primers/probes targeting different alleles are present. This alleviates the complications that otherwise plague simultaneous competing reactions, such as varying arrival time into the exponential stage and unintended interactions between primers.

In one aspect, the invention provides materials and methods for improving amplicon yield while maintaining the sensitivity and specificity in droplet based digital PCR. More specifically, the invention provides droplets containing a single nucleic acid template and multiplexed PCR primers and methods for detecting a plurality of targets in a biological sample by forming such droplets and amplifying the nucleic acid templates using droplet based digital PCR.

Reactions within microfluidic droplets yield very uniform fluorescence intensity at the end point, and ultimately the intensity depends on the efficiency of probe hydrolysis. Thus, in another aspect of the methods of the invention, different reactions with different efficiencies can be discriminated on the basis of end point fluorescence intensity alone even if they have the same color. Furthermore, in another method of the invention, the efficiencies can be tuned simply by adjusting the probe concentration, resulting in an easy-to-use and general purpose method for multiplexing. In one demonstration of the invention, a 5-plex TaqMan® dPCR assay worked "right out of the box", in contrast to lengthy optimizations that typify qPCR multiplexing to this degree. In another aspect of the invention, adding multiple colors increases the number of possible reactions geometrically, rather than linearly as with qPCR, because individual reactions can be labeled with multiple fluorophores. As an example, two fluorophores (VIC and FAM) were used to distinguish five different reactions in one implementation of the invention.

Methods of the invention are able to detect polymerase errors that occur during an amplification reaction and are able to exclude from analysis those products that are a result of polymerase errors. In essence, methods of the invention increase the sensitivity of digital PCR by identifying amplification products that are false positives, and excluding those products from analysis.

Methods of the invention involve forming sample droplets containing a single target nucleic acid, amplifying the target in the droplets, excluding droplets containing amplicon from the target and amplicon from a variant of the target, and analyzing target amplicons.

Nucleic Acid Target Molecules

Nucleic acid molecules include deoxyribonucleic acid (DNA) and/or ribonucleic acid (RNA). Nucleic acid molecules can be synthetic or derived from naturally occurring sources. In one embodiment, nucleic acid molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain embodiments, the nucleic acid molecules are obtained from a single cell. Biological samples for use in the present invention include viral particles or preparations. Nucleic acid molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA. In certain embodiments, the nucleic acid molecules are bound as to other target molecules such as proteins, enzymes, substrates, antibodies, binding agents, beads, small molecules, peptides, or any other molecule and serve as a surrogate for quantifying and/or detecting the target molecule.

Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Nucleic acid molecules may be single-stranded, double-stranded, or double-stranded with single-stranded regions (for example, stem- and loop-structures).

Droplet Formation

Methods of the invention involve forming sample droplets where some droplets contain zero target nucleic acid molecules, some droplets contain one target nucleic acid molecule, and some droplets may or may not contain multiple nucleic acid molecules (corresponding to limiting or terminal dilution, respectively, as defined above). In the preferred embodiment, the distribution of molecules within droplets obeys the Poisson distribution. However, methods for non-Poisson loading of droplets are known to those familiar with the art, and include but are not limited to active sorting of droplets, such as by laser-induced fluorescence, or by passive one-to-one loading. The description that follows assumes Poisson loading of droplets, but such description is not intended to exclude non-Poisson loading, as the invention is compatible with all distributions of DNA loading that conform to limiting or terminal dilution.

The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41,780) and European publication number EP2047910 to Raindance Technologies Inc. The content of each of which is incorporated by reference herein in its entirety.

Figure 2:
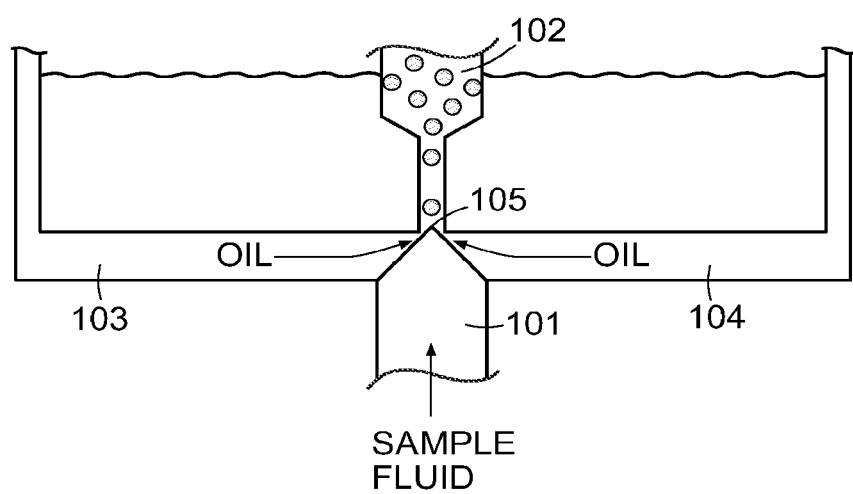
FIG. 2 depicts a portion of the droplet formation device of FIG. 1.

FIG. 1 shows an exemplary embodiment of a device 100 for droplet formation. Device 100 includes an inlet channel 101, and outlet channel 102, and two carrier fluid channels 103 and 104. Channels 101, 102, 103, and 104 meet at a junction 105. Inlet channel 101 flows sample fluid to the junction 105. Carrier fluid channels 103 and 104 flow a carrier fluid that is immiscible with the sample fluid to the junction 105. Inlet channel 101 narrows at its distal portion wherein it connects to junction 105 (See FIG. 2). Inlet channel 101 is oriented to be perpendicular to carrier fluid channels 103 and 104. Droplets are formed as sample fluid flows from inlet channel 101 to junction 105, where the sample fluid interacts with flowing carrier fluid provided to the junction 105 by carrier fluid channels 103 and 104. Outlet channel 102 receives the droplets of sample fluid surrounded by carrier fluid.

The sample fluid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with nucleic acid molecules can be used. The carrier fluid is one that is immiscible with the sample fluid. The carrier fluid can be a non-polar solvent, decane (e g., tetradecane or hexadecane), fluorocarbon oil, silicone oil or another oil (for example, mineral oil).

In certain embodiments, the carrier fluid contains one or more additives, such as agents which increase, reduce, or otherwise create non-Newtonian surface tensions (surfactants) and/or stabilize droplets against spontaneous coalescence on contact. Surfactants can include Tween, Span, fluorosurfactants, and other agents that are soluble in oil relative to water. In some applications, performance is improved by adding a second surfactant, or other agent, such as a polymer or other additive, to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be coated with a surfactant or a mixture of surfactants. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

In certain embodiments, the carrier fluid may be caused to flow through the outlet channel so that the surfactant in the carrier fluid coats the channel walls. In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Flourinert (3M)), which then serves as the carrier fluid.

One approach to merging sample fluids, using a device called a lambda injector, involves forming a droplet, and contacting the droplet with a fluid stream, in which a portion of the fluid stream integrates with the droplet to form a mixed droplet. In this approach, only one phase needs to reach a merge area in a form of a droplet. Further description of such method is shown in the co-owned and co-pending U.S. patent application to Yurkovetsky, et al. (U.S. patent application Ser. No. 61/441,985), the content of which is incorporated y reference herein in its entirety.

According to a method for operating the lambda injector, a droplet is formed as described above. After formation of the sample droplet from the first sample fluid, the droplet is contacted with a flow of a second sample fluid stream. Contact between the droplet and the fluid stream results in a portion of the fluid stream integrating with the droplet to form a mixed droplet.

The droplets of the first sample fluid flow through a first channel separated from each other by immiscible carrier fluid and suspended in the immiscible carrier fluid. The droplets are delivered to the merge area, i.e., junction of the first channel with the second channel, by a pressure-driven flow generated by a positive displacement pump. While droplet arrives at the merge area, a bolus of a second sample fluid is protruding from an opening of the second channel into the first channel. Preferably, the channels are oriented perpendicular to each other. However, any angle that results in an intersection of the channels may be used.

The bolus of the second sample fluid stream continues to increase in size due to pumping action of a positive displacement pump connected to channel, which outputs a steady stream of the second sample fluid into the merge area. The flowing droplet containing the first sample fluid eventually contacts the bolus of the second sample fluid that is protruding into the first channel. Contact between the two sample fluids results in a portion of the second sample fluid being segmented from the second sample fluid stream and joining with the first sample fluid droplet to form a mixed droplet. In certain embodiments, each incoming droplet of first sample fluid is merged with the same amount of second sample fluid.

In certain embodiments, an electric charge is applied to the first and second sample fluids. Description of applying electric charge to sample fluids is provided in Link et al. (U.S. patent application number 2007/0003442) and European Patent Number EP2004316 to Raindance Technologies Inc, the content of each of which is incorporated by reference herein in its entirety. Electric charge may be created in the first and second sample fluids within the carrier fluid using any suitable technique, for example, by placing the first and second sample fluids within an electric field (which may be AC, DC, etc.), and/or causing a reaction to occur that causes the first and second sample fluids to have an electric charge, for example, a chemical reaction, an ionic reaction, a photocatalyzed reaction, etc.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can be used.

The electric field facilitates rupture of the interface separating the second sample fluid and the droplet. Rupturing the interface facilitates merging of bolus of the second sample fluid and the first sample fluid droplet. The forming mixed droplet continues to increase in size until it a portion of the second sample fluid breaks free or segments from the second sample fluid stream prior to arrival and merging of the next droplet containing the first sample fluid. The segmenting of the portion of the second sample fluid from the second sample fluid stream occurs as soon as the shear force exerted on the forming mixed droplet by the immiscible carrier fluid overcomes the surface tension whose action is to keep the segmenting portion of the second sample fluid connected with the second sample fluid stream. The now fully formed mixed droplet continues to flow through the first channel.

In other embodiments, the rupture of the interface can be spontaneous, or the rupture can be facilitated by surface chemistry. The invention is not limited in regard to the method of rupture at the interface, as rupture can be brought about by any means.

In the context of PCR, in a preferred embodiment, the first sample fluid contains nucleic acid templates. Droplets of the first sample fluid are formed as described above. Those droplets will include the nucleic acid templates. In certain embodiments, the droplets will include only a single nucleic acid template, and thus digital PCR can be conducted. The second sample fluid contains reagents for the PCR reaction. Such reagents generally include Taq polymerase, deoxynucleotides of type A, C, G and T, magnesium chloride, and forward and reverse primers, all suspended within an aqueous buffer. The second fluid also includes detectably labeled probes for detection of the amplified target nucleic acid, the details of which are discussed below. A droplet containing the nucleic acid is then caused to merge with the PCR reagents in the second fluid as described above, producing a droplet that includes Taq polymerase, deoxynucleotides of type A, C, G and T, magnesium chloride, forward and reverse primers, detectably labeled probes, and the target nucleic acid. In another embodiment, the first fluid can contain the template DNA and PCR master mix (defined below), and the second fluid can contain the forward and reverse primers and the probe. The invention is not restricted in any way regarding the constituency of the first and second fluidics for PCR or digital PCR. For example, in some embodiments, the template DNA is contained in the second fluid inside droplets.

Target Amplification

Methods of the invention further involve amplifying the target nucleic acid in each droplet. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification, transcription based amplification system, nucleic acid sequence-based amplification, rolling circle amplification, and hyper-branched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

To effect amplification, primers are annealed to their complementary sequence within the target molecule. Following annealing, the primers are extended with a polymerase so as to form a new pair of complementary strands. The steps of denaturation, primer annealing and polymerase extension can be repeated many times (i.e., denaturation, annealing and extension constitute one cycle; there can be numerous cycles) to obtain a high concentration of an amplified segment of a desired target sequence. The length of the amplified segment of the desired target sequence is determined by relative positions of the primers with respect to each other and by cycling parameters, and therefore, this length is a controllable parameter.

Methods for performing PCR in droplets are shown for example in Link et al. (U.S. patent application numbers 2008/0014589, 2008/0003142, and 2010/0137163), Anderson et al. (U.S. Pat. No. 7,041,481 and which reissued as RE41,780) and European publication number EP2047910 to Raindance Technologies Inc. The content of each of which is incorporated by reference herein in its entirety.

The sample droplet may be pre-mixed with a primer or primers, or the primer or primers may be added to the droplet. In some embodiments, droplets created by segmenting the starting sample are merged with a second set of droplets including one or more primers for the target nucleic acid in order to produce final droplets. The merging of droplets can be accomplished using, for example, one or more droplet merging techniques described for example in Link et al. (U.S. patent application numbers 2008/0014589, 2008/0003142, and 2010/0137163) and European publication number EP2047910 to Raindance Technologies Inc.

In embodiments involving merging of droplets, two droplet formation modules are used. In one embodiment, a first droplet formation module produces the sample droplets consistent with limiting or terminal dilution of target nucleic acid. A second droplet formation or reinjection module inserts droplets that contain reagents for a PCR reaction. Such droplets generally include the "PCR master mix" (known to those in the art as a mixture containing at least Taq polymerase, deoxynucleotides of type A, C, G and T, and magnesium chloride) and forward and reverse primers (known to those in the art collectively as "primers"), all suspended within an aqueous buffer. The second droplet also includes detectably labeled probes for detection of the amplified target nucleic acid, the details of which are discussed below. Different arrangements of reagents between the two droplet types is envisioned. For example, in another embodiment, the template droplets also contain the PCR master mix, but the primers and probes remain in the second droplets. Any arrangement of reagents and template DNA can be used according to the invention.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule ($Td=2(A+T)+4(G+C)$). Another method for determining the melting temperature of primers is the nearest neighbor method Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

In one embodiment, the droplet formation modules are arranged and controlled to produce an interdigitation of sample droplets and PCR reagent droplets flowing through a channel. Such an arrangement is described for example in Link et al. (U.S. patent application numbers 2008/0014589, 2008/0003142, and 2010/0137163) and European publication number EP2047910 to Raindance Technologies Inc.

A sample droplet is then caused to merge with a PCR reagent droplet, producing a droplet that includes the PCR master mix, primers, detectably labeled probes, and the target nucleic acid. Droplets may be merged for example by: producing dielectrophoretic forces on the droplets using electric field gradients and then controlling the forces to cause the droplets to merge; producing droplets of different sizes that thus travel at different velocities, which causes the droplets to merge; and producing droplets having different viscosities that thus travel at different velocities, which causes the droplets to merge with each other. Each of those techniques is further described in Link et al. (U.S. patent application numbers 2008/0014589, 2008/0003142, and 2010/0137163) and European publication number EP2047910 to Raindance Technologies Inc. Further description of producing and controlling dielectrophoretic forces on droplets to cause the droplets to merge is described in Link et al. (U.S. patent application number 2007/0003442) and European Patent Number EP2004316 to Raindance Technologies Inc.

In another embodiment, called simple droplet generation, a single droplet formation module, or a plurality of droplet formation modules are arranged to produce droplets from a mixture already containing the template DNA, the PCR master mix, primers, and detectably labeled probes. In yet another embodiment, called co-flow, upstream from a single droplet formation module two channels intersect allowing two flow streams to converge. One flow stream contains one set of reagents and the template DNA, and the other contains the remaining reagents. In the preferred embodiment for co-flow, the template DNA and the PCR master mix are in one flow stream, and the primers and probes are in the other. However, the invention is not limited in regard to the constituency of either flow stream. For example, in another embodiment, one flow stream contains just the template DNA, and the other contains the PCR master mix, the primers, and the probes. On convergence of the flow streams in a fluidic intersection, the flow streams may or may not mix before the droplet generation nozzle. In either embodiment, some amount of fluid from the first stream, and some amount of fluid from the second stream are encapsulated within a single droplet. Following encapsulation, complete mixing occurs.

Once final droplets have been produced by any of the droplet forming embodiments above, or by any other embodiments, the droplets are thermal cycled, resulting in amplification of the target nucleic acid in each droplet. In certain embodiments, the droplets are collected off-chip as an emulsion in a PCR thermal cycling tube and then thermally cycled in a conventional thermal cycler. Temperature profiles for thermal cycling can be adjusted and optimized as with any conventional DNA amplification by PCR.

In certain embodiments, the droplets are flowed through a channel in a serpentine path between heating and cooling lines to amplify the nucleic acid in the droplet. The width and depth of the channel may be adjusted to set the residence time at each temperature, which can be controlled to anywhere between less than a second and minutes.

In certain embodiments, the three temperature zones are used for the amplification reaction. The three temperature zones are controlled to result in denaturation of double stranded nucleic acid (high temperature zone), annealing of primers (low temperature zones), and amplification of single stranded nucleic acid to produce double stranded nucleic acids (intermediate temperature zones). The temperatures within these zones fall within ranges well known in the art for conducting PCR reactions. See for example, Sambrook et al. (Molecular Cloning, A Laboratory Manual, 3$^{rd}$ edition, Cold Spring Harbor Laboratory Press, Cold Spring Harbor, New York, 2001).

In certain embodiments, the three temperature zones are controlled to have temperatures as follows: 95° C. ($T_H$), 55° C. ($T_L$), 72° C. ($T_M$). The prepared sample droplets flow through the channel at a controlled rate. The sample droplets first pass the initial denaturation zone ($T_H$) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the high temperature zone, of approximately 95° C., where the sample is first separated into single stranded DNA in a process called denaturation. The sample then flows to the low temperature, of approximately 55° C., where the hybridization process takes place, during which the primers anneal to the complementary sequences of the sample. Finally, as the sample flows through the third medium temperature, of approximately 72° C., the polymerase process occurs when the primers are extended along the single strand of DNA with a thermostable enzyme. Methods for controlling the temperature in each zone may include but are not limited to electrical resistance, peltier junction, microwave radiation, and illumination with infrared radiation.

The nucleic acids undergo the same thermal cycling and chemical reaction as the droplets passes through each thermal cycle as they flow through the channel. The total number of cycles in the device is easily altered by an extension of thermal zones or by the creation of a continuous loop structure. The sample undergoes the same thermal cycling and chemical reaction as it passes through N amplification cycles of the complete thermal device.

In other embodiments, the temperature zones are controlled to achieve two individual temperature zones for a PCR reaction. In certain embodiments, the two temperature zones are controlled to have temperatures as follows: 95° C. ($T_H$) and 60° C. ($T_L$). The sample droplet optionally flows through an initial preheat zone before entering thermal cycling. The preheat zone may be important for some chemistry for activation and also to ensure that double stranded nucleic acid in the droplets are fully denatured before the thermal cycling reaction begins. In an exemplary embodiment, the preheat dwell length results in approximately 10 minutes preheat of the droplets at the higher temperature.

The sample droplet continues into the high temperature zone, of approximately 95° C., where the sample is first separated into single stranded DNA in a process called denaturation. The sample then flows through the device to the low temperature zone, of approximately 60° C., where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing.

In another embodiment the droplets are created and/or merged on chip followed by their storage either on the same chip or another chip or off chip in some type of storage vessel such as a PCR tube. The chip or storage vessel containing the droplets is then cycled in its entirety to achieve the desired PCR heating and cooling cycles.

In another embodiment the droplets are collected in a chamber where the density difference between the droplets and the surrounding oil allows for the oil to be rapidly exchanged without removing the droplets. The temperature of the droplets can then be rapidly changed by exchange of the oil in the vessel for oil of a different temperature. This technique is broadly useful with two and three step temperature cycling or any other sequence of temperatures.

The invention is not limited by the method used to thermocycle the droplets. Any method of thermocycling the droplets may be used.

Target Detection

After amplification, droplets are flowed to a detection module for detection of amplification products. For embodiments in which the droplets are thermally cycled off-chip, the droplets require re-injection into either a second fluidic circuit for read-out—that may or may not reside on the same chip as the fluidic circuit or circuits for droplet generation—or in certain embodiments the droplets may be reinjected for read-out back into the original fluidic circuit used for droplet generation. The droplets may be individually analyzed and detected using any methods known in the art, such as detecting the presence or amount of a reporter. Generally, the detection module is in communication with one or more detection apparatuses. The detection apparatuses can be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at a sorting module. Further description of detection modules and methods of detecting amplification products in droplets are shown in Link et al. (U.S. patent application numbers 2008/0014589, 2008/0003142, and 2010/0137163) and European publication number EP2047910 to Raindance Technologies Inc.

In certain embodiments, amplified target are detected using detectably labeled probes. In particular embodiments, the detectably labeled probes are optically labeled probes, such as fluorescently labeled probes. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcoulurarin (Coumaran 151); cyanine dyes; cyanosine; 4',6-diaminidino-2-phenylindole (DAPI); 5'5''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron.™. Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. Preferred fluorescent labels are FAM and VIC™ (from Applied Biosystems). Labels other than fluorescent labels are contemplated by the invention, including other optically-detectable labels.

In certain aspects, the droplets of the invention contain a plurality of detectable probes that hybridize to amplicons produced in the droplets. Members of the plurality of probes can each include the same detectable label, or a different detectable label. The plurality of probes can also include one or more groups of probes at varying concentration. The groups of probes at varying concentrations can include the same detectable label which vary in intensity, due to varying probe concentrations.

In a separate embodiment the detection can occur by the scanning of droplets confined to a monolayer in a storage device that is transparent to the wavelengths or method or detection. Droplets stored in this fashion can be scanned either by the movement of the storage device by the scanner or the movement of the scanner over the storage device.

The invention is not limited to the TaqMan assay, as described above, but rather the invention encompasses the use of all fluorogenic DNA hybridization probes, such as molecular beacons, Solaris probes, scorpion probes, and any other probes that function by sequence specific recognition of target DNA by hybridization and result in increased fluorescence on amplification of the target sequence.

Digital PCR Performance in Droplets

Figure 3A:
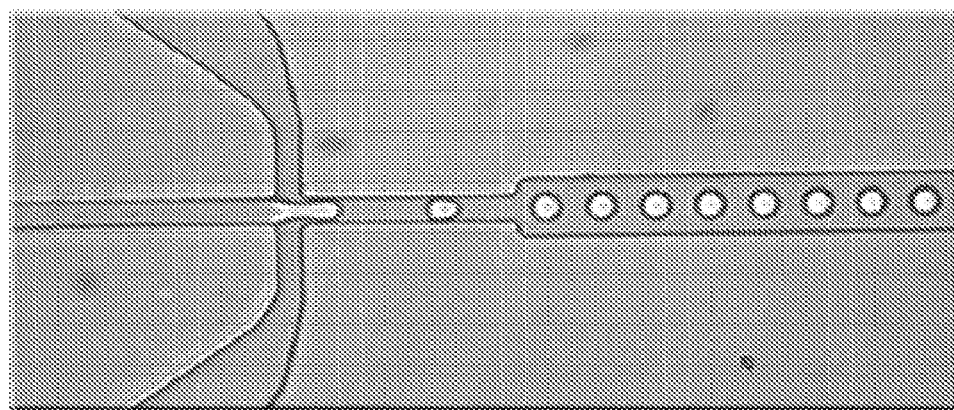
FIGS. 3A-C depict an exemplary microfluidic system for droplet generation and readout.
Figure 3B:
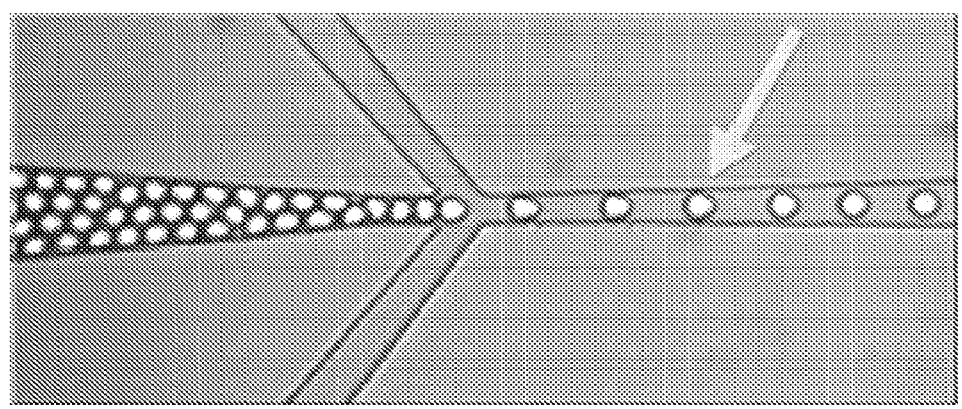
Figure 3C:
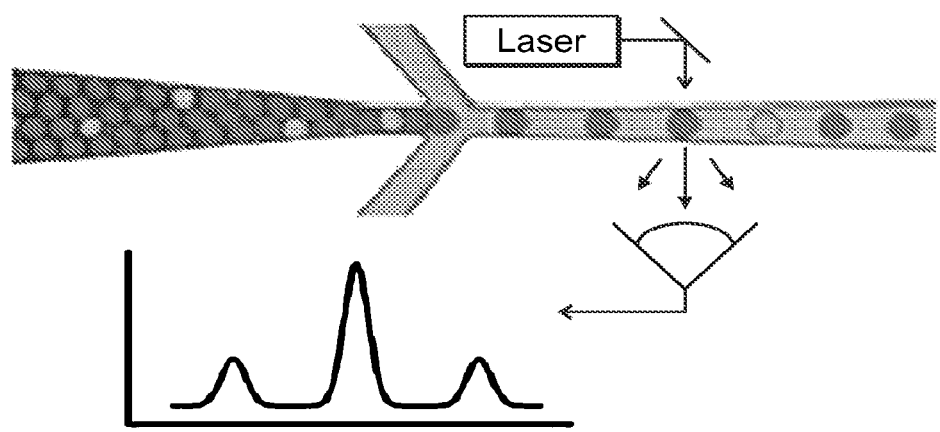

Digital PCR performance in the emulsion format was validated by measuring a serial dilution of a reference gene, branched chain keto acid dehydrogenase E1 (BCKDHA). Mixtures of the PCR master mix, 1× primers and probe for BCKDHA, and varying concentrations of a mixture of human genomic DNA (1:1 NA14091 and NA13705) were compartmentalized into over one million 5.3 pL droplets in a water-in-fluorinated oil emulsion using the droplet generation microfluidic chip. The emulsion was thermally cycled off-chip and afterwards the fluorescence of each droplet was analyzed by fluorescence in the readout chip (see FIG. 3). An exemplary microfluidic system for droplet generation and readout is depicted in FIG. 3. The microfluidic system for droplet generation and readout. As shown in FIG. 3a (droplet generation chip), a continuous aqueous phase containing the PCR master mix, primers, and probes, and template DNA flowed into the fluidic intersection from the left, and the carrier oil entered from the top and bottom. An emerging bolus of aqueous liquid was imaged inside the intersection just prior to snapping off into a discrete 4 μL droplet as the fluidic strain began to exceed the surface tension of the aqueous liquid. The steady train of droplets leaving the intersection toward the right was collected off chip as a stable emulsion for thermal cycling. FIG. 3b depicts the droplet spacing for readout. Flows were arranged as in 3a, except instead of a continous phase, the emulsion from (a) was injected from the left into the intersection after thermal cycling. The oil drained from the emulsion during off-chip handling, hence the emulsion appeared tightly packed in the image before the intersection. The oil introduced in the intersection separated the droplets and the fluorescence of each droplet was measured at the location marked by the arrow. FIG. 3c depicts a cartoon of droplet readout by fluorescence. The relatively infrequent PCR(+) droplets (light gray) flow along with the majority of PCR(−) droplets (dark gray) toward the detector. The droplets were interrogated sequentially by laser induced fluorescence while passing through the detection region.

In a serial dilution the average number of target DNA molecules per droplet—called the "occupancy" from this point forward—should decrease in direct proportion to the DNA concentration. The occupancy was calculated from Poisson statistics using the following equation well known to those experienced in the art:

$$\text{occupancy} = \ln\left(\frac{P+N}{F}\right), \quad (1)$$

where P and N are the numbers of PCR(+) and PCR(−) droplets respectively.

Figure 4A:
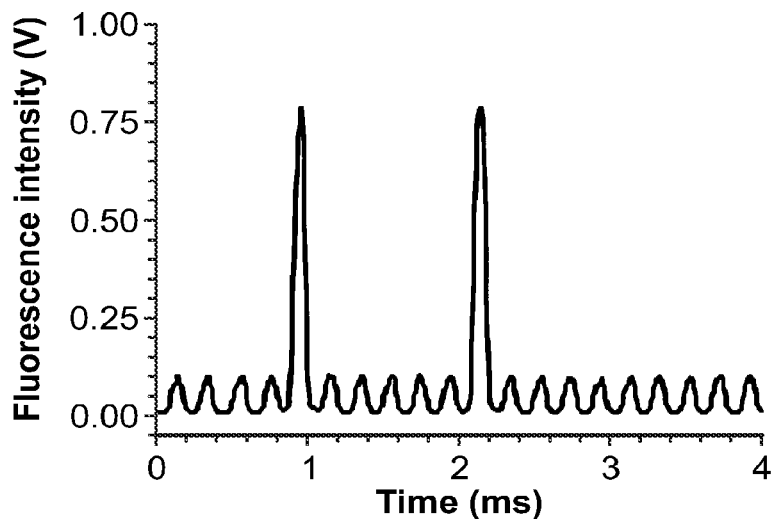
FIGS. 4A-C depicts the serial dilution of template DNA quantified by dPCR.
Figure 4B:
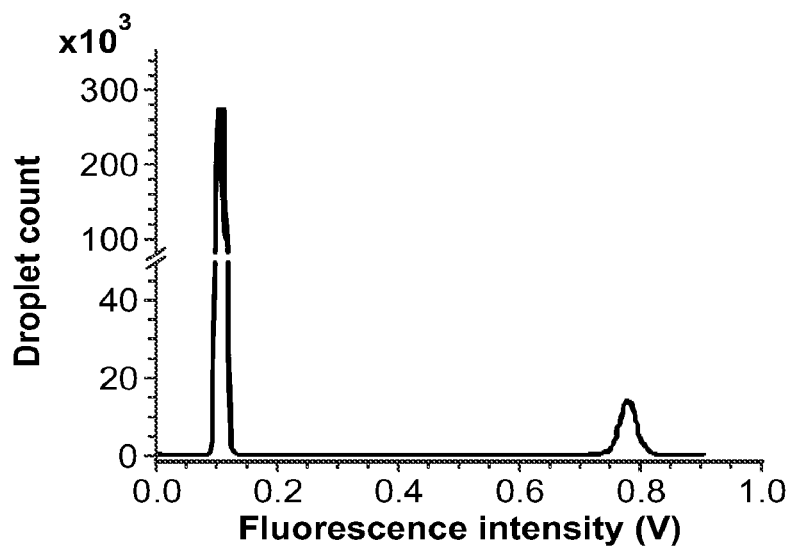
Figure 4C:
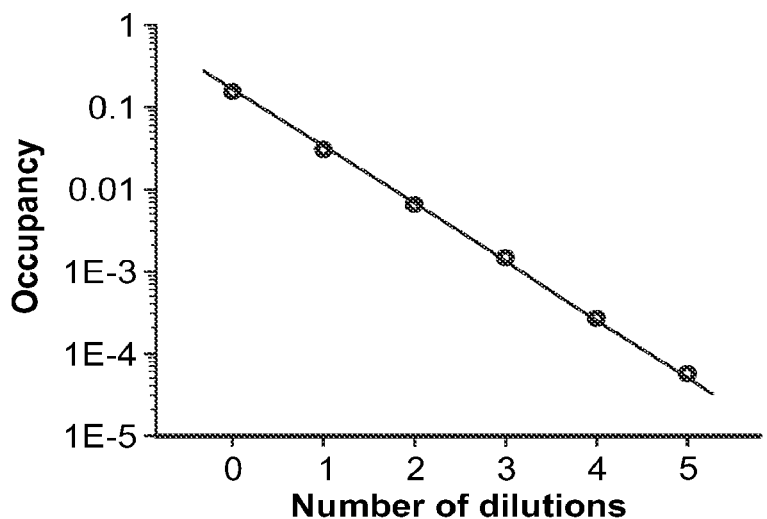

Droplets were analyzed by fluorescence while flowing through the readout chip to count the numbers of PCR(+) and PCR(−) droplets (see FIG. 3c). As each droplet passed the detection zone (marked with an arrow in FIG. 3b), a burst of fluorescence was observed. To account for small run-to-run differences in the fluorescence intensity that can occur due to different chip positioning, etc., each set of data was scaled such that the average fluorescence intensity of the empty droplets was 0.1 V. FIG. 4a shows a very short duration of a typical trace of fluorescence bursts from individual droplets for the sample with the highest DNA concentration in the series. PCR(+) and PCR(−) droplets were easily discriminated by fluorescence intensity. The two large bursts of fluorescence peaking at ~0.8 V arose from the PCR(+) droplets, whereas the smaller bursts due to incomplete fluorescence quenching in the PCR(−) droplets peaked at −0.1 V. A histogram of peak intensities from the complete data set revealed two clear populations centered at 0.10 and 0.78 V (FIG. 4b), demonstrating that the trend evident in the short trace in FIG. 4a was stable over much longer periods of time. Integration over the two populations in FIG. 4b yielded a total of 197,507 PCR(+) and 1,240,126 PCR(−) droplets. Hence the occupancy was 0.15 for this sample by Eqn. 1, corresponding to the expected occupancy of 0.18 based on the measured DNA concentration of 110 ng/μL. The occupancy was measured for each sample in the serial dilution and fit to the dilution equation:

$$\text{occupancy}(n) = \frac{A}{f^{R2}}, \quad (2)$$

where n is the number of dilutions, A is the occupancy at the starting concentration (n=0), and f is the dilution factor. The linear fit was in excellent agreement with the data, with an $R^2$ value of and the fitted dilution factor of 4.8 in close agreement with the expected value of 5.0.

Multiplexing Primers in a Digital PCR Reaction

Droplet based digital PCR technology, as described in Link et al. (U.S. patent application numbers 2008/0014589, 2008/0003142, and 2010/0137163), Anderson et al. (U.S. Pat. No. 7,041,481 and which reissued as RE41,780) and European publication number EP2047910 to Raindance Technologies Inc, (the contents of each of which are incorporated by reference herein in their entireties) utilizes a single primer pair per library droplet. This library droplet is merged with a template droplet which contains all the PCR reagents including genomic DNA except for the primers. After merging of the template and the primer library droplets the new droplet now contains all the reagents necessary to perform PCR. The droplet is then thermal cycled to produce amplicons. In one embodiment, the template DNA is diluted in the template mix such that on average there is less than one haploid genome per droplet.

Having only one haploid genome (i.e., one allele) per droplet gives droplet PCR advantages over standard singleplex or multiplex PCR in tubes or microwells. For example, in traditional PCR, both alleles are present in the reaction mix so if there is a difference in the PCR efficiency between alleles, the allele with the highest efficiency will be over represented. Additionally, there can be variances in the sequence to which the PCR primers hybridize, despite careful primer design. A variance in the primer hybridization sequence can cause that primer to have a lower efficiency for hybridization for the allele that has the variance compared to the allele that has the wild type sequence. This can also cause one allele to be amplified preferentially over the other allele if both alleles are present in the same reaction mix.

These issues are avoided in droplet based PCR because there is only one template molecule per droplet, and thus one allele per droplet. Thus, even if primer variance exists that reduces the PCR efficiency for one allele, there is no competition between alleles because the alleles are separated and thus uniformly amplified.

Optimization of traditional multiplexing of standard PCR primers in tubes or wells is known to be difficult. Multiple PCR amplicons being generated in the same reaction can lead to competition between amplicons that have differing efficiencies due to differences in sequence or length. This results in varying yields between competing amplicons which can result in non uniform amplicon yields. However, because droplet based digital PCR utilizes only one template molecule per droplet, even if there are multiple PCR primer pairs present in the droplet, only one primer pair will be active. Since only one amplicon is being generated per droplet, there is no competition between amplicons, resulting in a more uniform amplicon yield between different amplicons.

A certain amount of DNA is required to generate either a specific quantity of DNA and/or a specific number of PCR positive droplets to achieve sufficient sequencing coverage per base. Because only a percentage of the droplets are PCR positive, approximately 1 in 3 in the standard procedure, it takes more DNA to achieve the equivalent PCR yield per template DNA molecule. The number of PCR positive droplets and thus the amplicon yield can be increased by adding more genomic DNA. For instance, increasing the amount of genomic DNA twofold while maintaining the number of droplets constant will double the amplicon yield.

However there is a limit to the amount of genomic DNA that can be added before there is a significant chance of having both alleles for a gene in the same droplet, thereby eliminating the advantage of droplet PCR for overcoming allele specific PCR and resulting in allelic dropout.

One way to allow the input of more genomic DNA is by generating more droplets to keep the haploid molecules per droplet ratio constant. For instance doubling the amount of DNA and doubling the amount of droplets increases the amplicon yield by 2× while maintaining the same haploid genome per droplet ratio. However, while doubling the number of droplets isn't problematic, increasing the amount of DNA can be challenging to users that have a limited amount of DNA.

The multiplexing of PCR primers in droplets enables the simultaneous increase in the number of PCR droplets while keeping the amount of input DNA the same or lower to generate an equal or greater amplicon yield. This results in an overall increase in the amount of PCR positive droplets and amplicon yield without the consumption of more DNA.

By way of example, if there is an average of 1 haploid genome per every 4 droplets or ¼ of the haploid genome per droplet and one PCR primer pair per droplet, the chances of the correct template being present for the PCR primer in the droplet is 1 out of 4. However, if there are 2 PCR primer pairs per droplet, then there is double the chance that there will be the correct template present in the droplet. This results in 1 out of 2 droplets being PCR positive which doubles the amplicon yield without doubling the input DNA. If the number of droplets containing the 2× multiplexed primers is doubled and the DNA kept constant, then the number of PCR positive droplets drops back to 1 in 4, but the total number of PCR droplets remains the same because the number of droplets have been doubled. If the multiplexing level in each droplet is increased to 4× and the input DNA is the same, the chance of the correct template molecule being present in each droplet doubles. This results in the number of PCR positive droplets being increased to 1 in 2 which doubles the amount of amplicon yield without increasing the amount of input DNA. Thus, by increasing the multiplexing of PCR primers in each droplet and by increasing the number of droplets overall, the amplicon yield can be increased by 4-fold without increasing the amount of input DNA.

Alternatively, if the amplicon yield is already sufficient, by increasing the multiplexing level for the PCR primers in each droplet, the amount of input genomic DNA can be dropped without sacrificing amplicon yield. For example if the multiplexing level of the PCR primers goes from 1× to 2×, the amount of input genomic DNA can be decreased by 2× while still maintaining the same overall amplicon yield.

Even though the number of PCR primer pairs per droplet is greater than one, there is still only one template molecule per droplet and thus there is only one primer pair per droplet that is being utilized at one time. This means that the advantages of droplet PCR for eliminating bias from either allele specific PCR or competition between different amplicons is maintained.

An example demonstration of droplet-based amplification and detection of multiple target sequences in a single droplet is shown here. Multiple copies of 5 sets of primers (primers for TERT, RNaseP, E1a, SMN1 and SMN2) were encapsulated in a single droplet at various concentrations along with the template DNA and the PCR master mix. Probes that specifically bind to TERT, RNaseP, E1a, SMN1 or SMN2 were also encapsulated in the droplets containing the primers. Probes for TERT, RNaseP and E1a were labeled with the VIC dye and probes for SMN1 and SMN2 were labeled with the FAM dye. The sequences for TERT RNaseP, E1a, SMN1 and SMN2 were amplified by PCR. The PCR was conducted with a standard thermal cycling setting. For example:

95° C. for 10 min
31 cycles
  92° C. for 15 s
  60° C. for 60 s

Figure 5B:
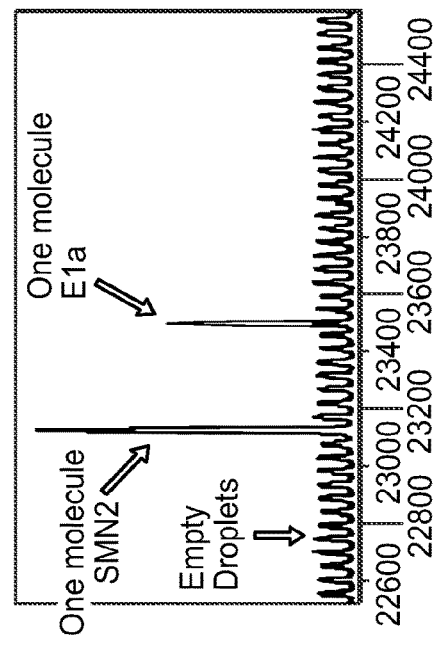
FIG. 5B is a time trace of fluorescence intensity detected from droplets after PCR amplification.
Figure 5C:
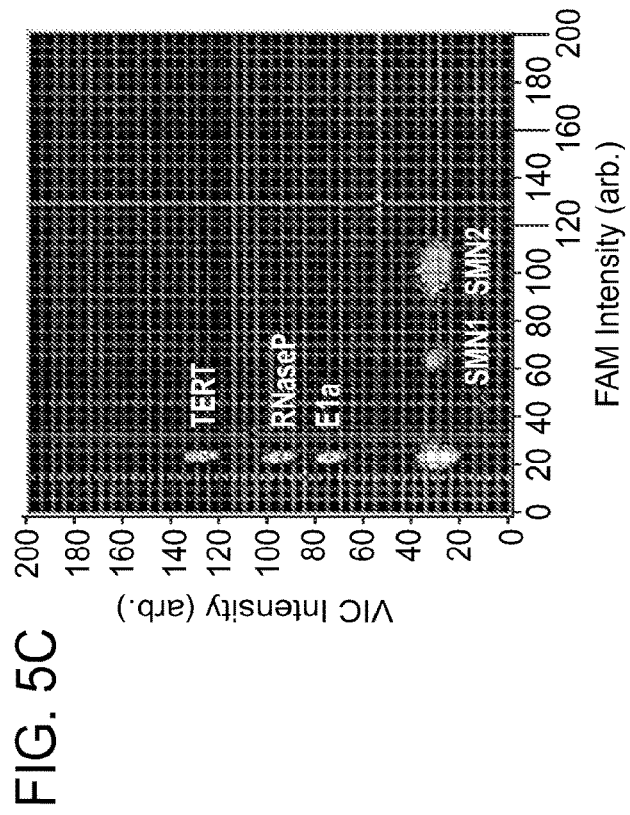
FIG. 5C is a scatter plot showing clusters representing droplets that contain specific amplified sequences (TERT, RNaseP, E1a, SMN1 and SMN2).
Figure 5A:
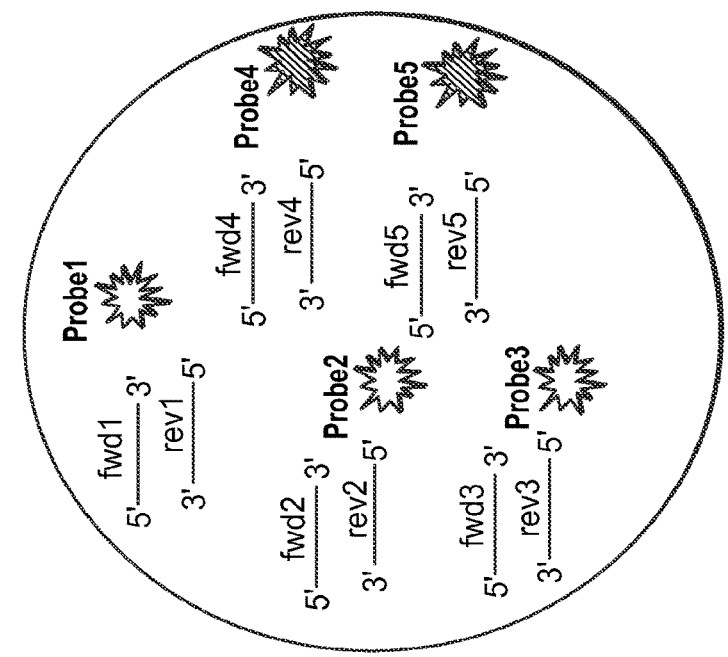
FIG. 5A is a schematic representation of a droplet having 5 sets of primers for PCR amplification of a template sequence and 5 probes, each labeled with a fluorescent dye, that binds specifically to the amplified sequences.

At the end of the PCR, the fluorescence emission from each droplet was determined and plotted on a scattered plot based on its wavelength and intensity. Six clusters, each representing droplets having the corresponding fluorescence wavelength and intensity were shown. The TERT, RNaseP and E1a clusters showed the fluorescence of the VIC dye at three distinct intensities and SMN1 and SMN1 clusters showed the fluorescence of the FAM dye at two distinct intensities (FIG. 5). The number of droplets, each having one or more sequences selected from TERT, RNaseP, E1a, SMN1 and SMN2, can be determined from the scattered plot.

In an another demonstration of droplet-based amplification and detection of multiple target sequences in a single droplet, 5 sets of primers (primers for TERT, RNaseP, E1a, 815A and 815G) were encapsulated in a single droplet at various concentrations along with the template DNA, the PCR master mix, and the probes. The five different probes TERT, RNaseP, E1a, 815A and 815G were also encapsulated in the droplets containing the primers. Probes for TERT and 815A were labeled with the VIC dye and probes for 815G were labeled with the FAM dye. For each of RNaseP and E1a, two probes, one labeled with the VIC dye and the other labeled with the FAM dye, were encapsulated.

The droplets containing both the primers and probes were fused with droplets containing the template. PCR reactions were conducted with the fused droplets to amply the sequences for TERT, RNaseP, E1a, 815A and 815G. The PCR was conducted with a standard thermal cycling setting.

Figure 6B:
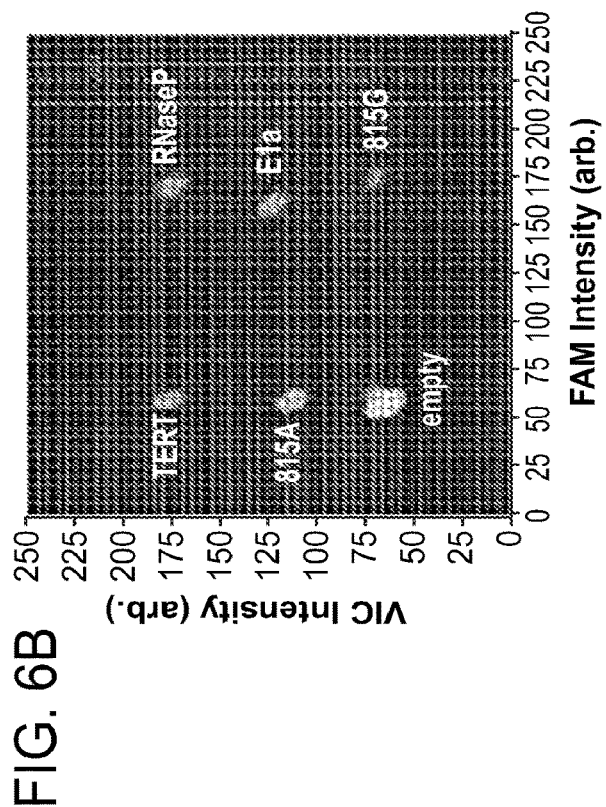
FIG. 6B is a scatter plot showing clusters representing droplets that contain specific amplified sequences (TERT, 815A, RNaseP, E1a, and 815G).
Figure 6C:
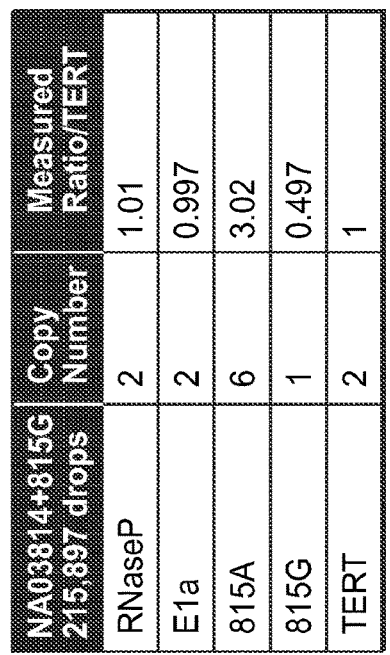
FIG. 6C is a table showing the copy number of specific sequences shown in FIG. 6B.
Figure 6A:
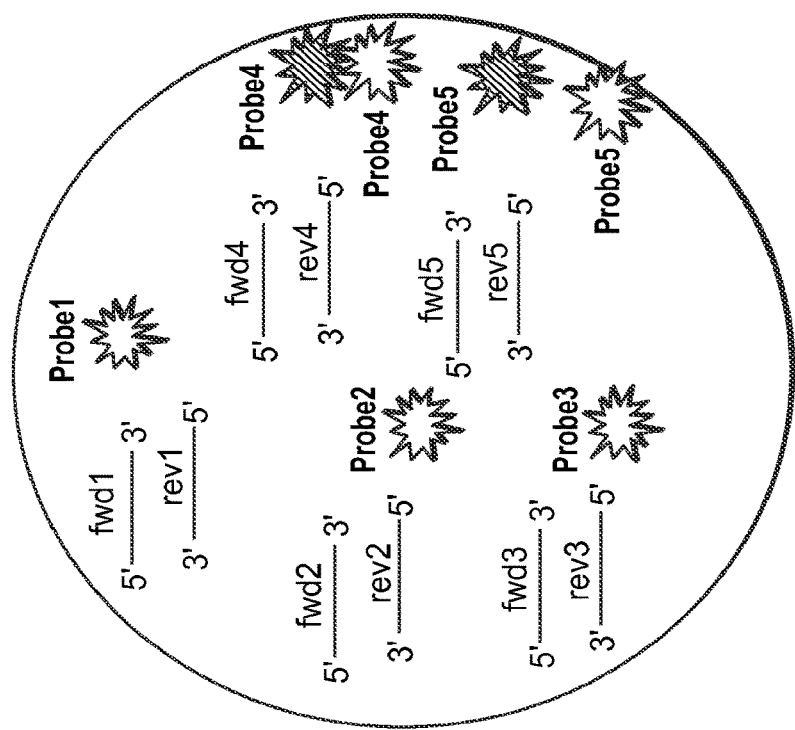
FIG. 6A is a schematic representation of a droplet having 5 sets of primers for PCR amplification of a template sequence and 5 probes, each labeled with a fluorescent dye, that binds specifically to the amplified sequences.

At the end of the PCR, the fluorescence emission from each fused droplet was determined and plotted on a scattered plot based on its wavelength and intensity. Six clusters, each representing droplets having the corresponding fluorescence wavelength and intensity were shown. The TERT and 815A clusters showed the fluorescence of the VIC dye at two distinct intensities; the 815G clusters showed the fluorescence of the FAM dye; and the RNaseP and E1a clusters showed the fluorescence of both the FAM and the VIC dye at distinct intensities (FIG. 6). The number of droplets, each having one or more sequences selected from TERT, RNaseP, E1a, 815A and 815G, can be determined from the scattered plot. The copy number of RNaseP, E1a, 815A and 815G in the template were determined by the ratio between the number of droplets having the RNaseP, E1a, 815A and/or 815G sequences and the number of droplets having the TERT sequence (FIG. 6).

In yet another exemplary demonstration of multiplexed primer pairs in a droplet-based digital PCR reaction, two droplet libraries were generated: droplet library A was generated where each droplet contained only one primer pair; and droplet library B was generated where the primer pairs were multiplexed at 5× level in each droplet. HapMap sample NA18858 was processed in duplicate with droplet libraries A or B using standard procedures. Two µg sample DNA was used for droplet library A and one µg sample DNA was used for the 5× multiplex droplet library B. After PCR amplification, both droplet libraries were broken and purified over a Qiagen MinElute column and then run on an Agilent Bioanalyzer. Samples were sequenced by Illumina on the Illumina GAII with 50 nucleotide reads and the sequencing results were analyzed using the standard sequencing metrics. The results from the 5× multiplexed droplet library B were compared to the singleplex droplet library A using standard metrics shown in the Table below.

The results obtained from the 5× multiplexed droplet library B were equivalent or better than what was obtained from droplet library A. The multiplexing of primers delivers the same sequencing results for base coverage, specificity and uniformity that the singleplexing does with the added advantage of reduced input DNA.

| Sample | Total reads | Mapped reads | Specificity | Mean base coverage | C1 | C20 | C100 | Base coverage (0.2× of mean) |
|---|---|---|---|---|---|---|---|---|
| Library A with sample 1 | 27431697 | 99.4% | 0.813 | 1394 | 99.5% | 99.0% | 98.2% | 92.8% |
| Library A with sample 2 | 15147288 | 99.4% | 0.862 | 819 | 99.1% | 98.2% | 87.6% | 78.0% |
| Library B with sample 1 | 27861378 | 99.5% | 0.847 | 1472 | 99.7% | 99.3% | 97.6% | 89.9% |
| Library B with sample 2 | 25758406 | 99.1% | 0.837 | 1321 | 99.8% | 99.4% | 97.9% | 91.3% |

Total reads: total number of sequencing read found within the provided sample data.
Mapped reads (%): percentage of total reads that mapped to the human genome.
Specificity: percentage of mapped reads that include the target. The target includes all amplicon sequences with primer sequences excluded.
Mean base coverage: average base coverage within the target. The target includes all amplicon sequences with primer sequences excluded.
C1: % of target that has at least 1× base coverage. Note: non-unique sequencing reads are mapped randomly.
C20: % of target that has at least 20× base coverage.
C100: % of target that has at least 100× base coverage.
Base coverage (0.2× of mean): % of target that has at least 20% of mean base coverage.

Monochromatic Gene Copy Number Assay

Figure 7A:
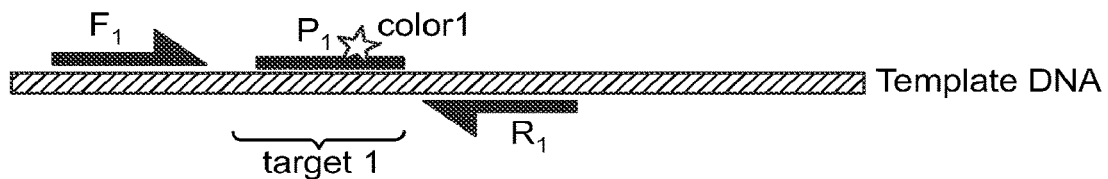
Figure 7B:
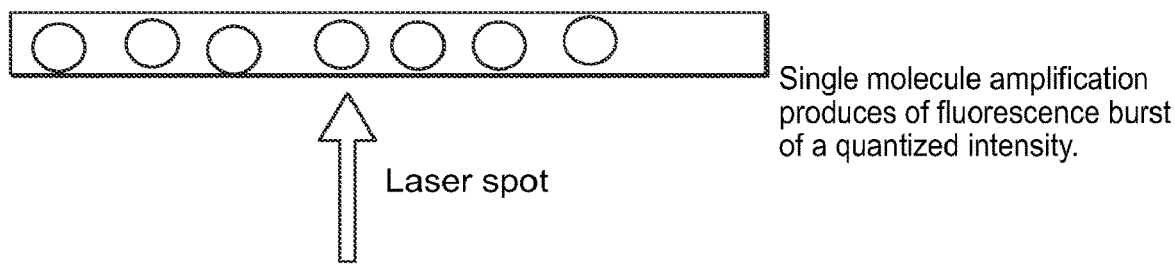
Figure 7C:
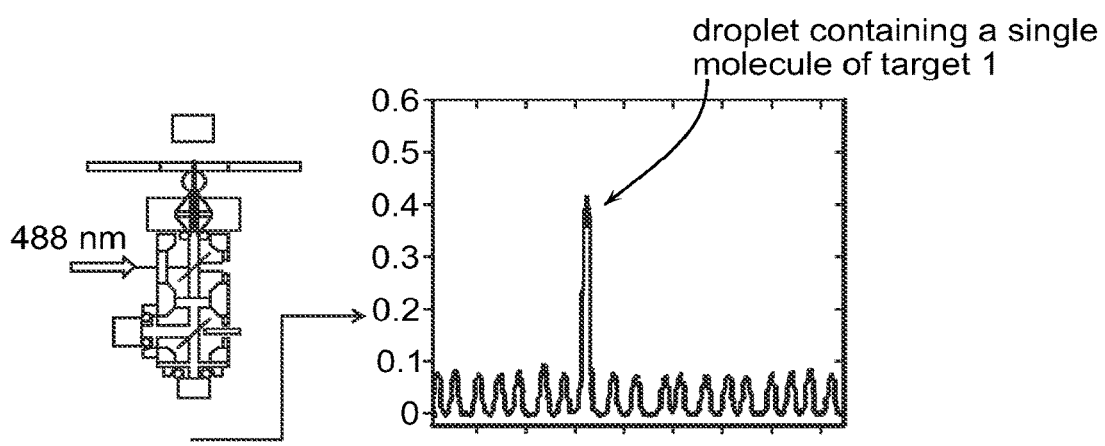

Traditional digital PCR methods involve the use of a single labeled probe specific for an individual target. FIG. 7 is a schematic depicting one-color detection of a target sequence using droplet based digital PCR. As shown in Panel A of FIG. 7, a template DNA is amplified with a forward primer (F1) and a reverse primer (R1). Probe (P1) labeled with a fluorophore of color 1 binds to the target genetic sequence (target 1). Microdroplets are made of diluted solution of template DNA under conditions of limiting or terminal dilution. Droplets containing the target sequence emit fluorescence and are detected by laser (Panels B and C). The number of microcapsules either containing or not containing the target sequence is shown in a histogram (D) and quantified (E).

Figure 8B:
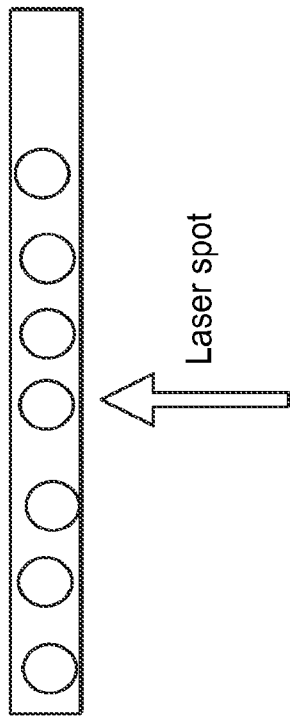
Figure 8C:
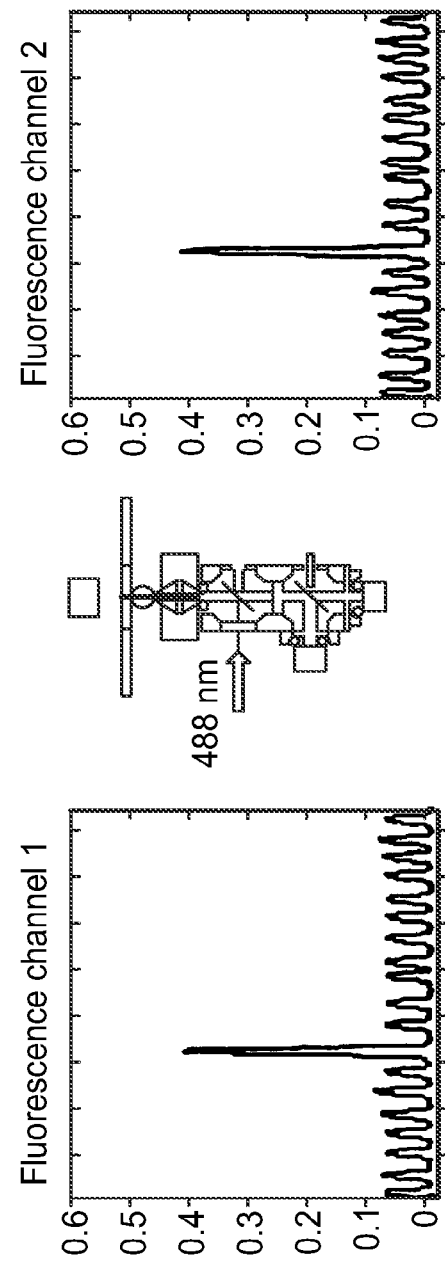
Figure 8D:
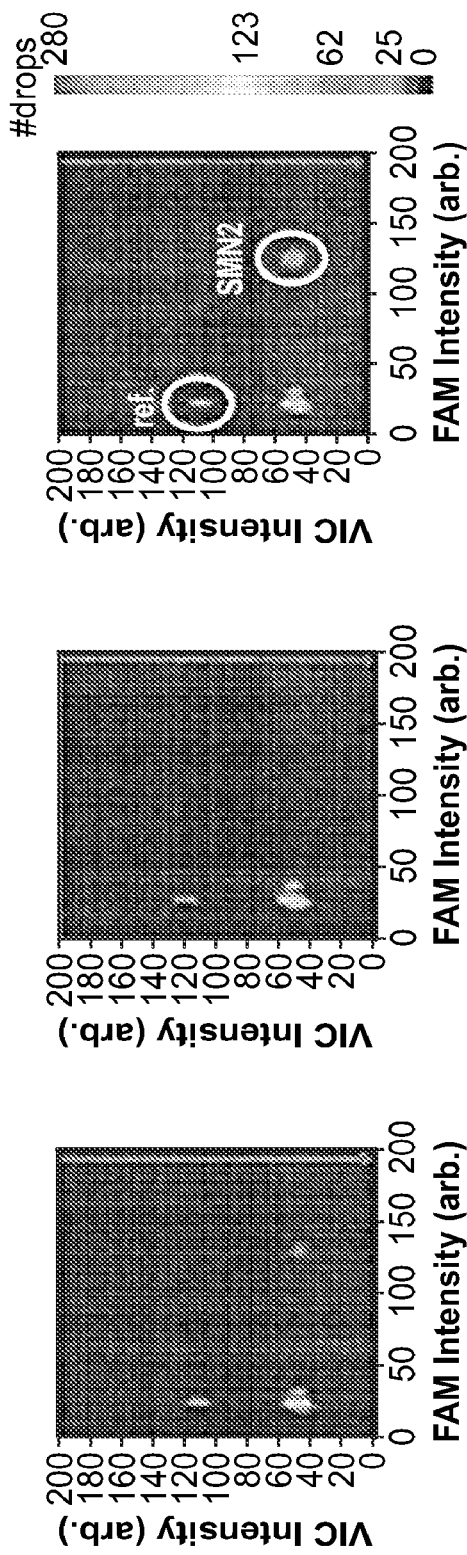

FIG. 8 is a schematic depicting two-color detection of two genetic sequences with a microfluidic device. As shown in Panel A of FIG. 8, a template DNA is amplified with two sets of primers: forward primer (F1) and a reverse primer (R1), and forward primer (F2) and a reverse primer (R2). Probe (P1) labeled with a fluorophore of color 1 binds to the target 1 and probe (P2) labeled with a fluorophore of color 2 binds to the target 2 (Panels B and C). Droplets are made of diluted solution of template DNA under conditions of limiting or terminal dilution. Droplets containing the target sequence 1 or 2 emit fluorescence of color 1 or 2 respectively and are optically detected by laser (Panels B and C). The number of microcapsules containing target 1 or 2 is shown by histogram in Panel D.

Figure 9C:
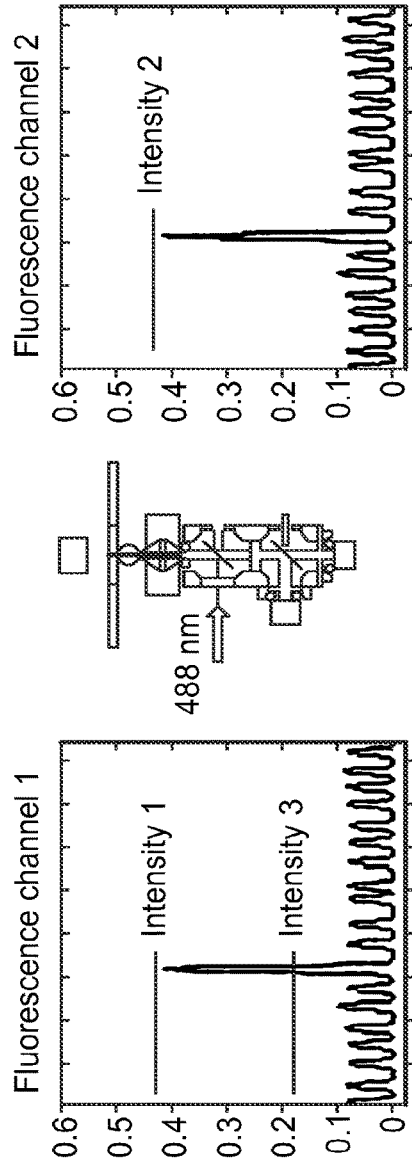
Figure 9D:
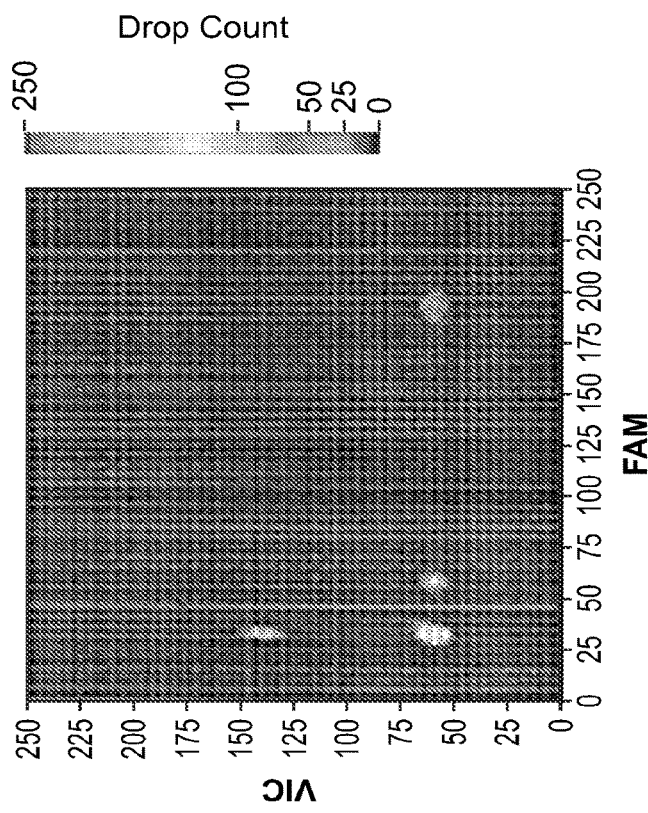

Methods of the invention involve performing accurate quantitation of multiple different DNA targets by dPCR using probes with the same fluorophore. FIG. 9 is a schematic depicting two-color detection of three genetic sequences with a microfluidic device. As shown in Panel A of FIG. 9, a template DNA is amplified with three sets of primers: forward primers (F1, F2 and F3) and reverse primers (R1, R2 and R3). Probes (P1, P2 and P3) are labeled with fluorophores (color 1, color 2 and color 1) and bind to the target genetic sequences (target 1, target 2 and target 3) (Panels B and C). Microdroplets are made of diluted solution of template DNA under conditions of limiting or terminal dilution. Microdroplets containing target sequence 1 or 3 emit fluorescence of color 1 at two different intensities; and microdroplets containing target sequence 2 emit fluorescence of color 2. The number of microdroplets containing target 1, 2 or 3 is shown by histogram in Panel D.

Recent results from the droplet digital PCR (dPCR) shows that multiple independent PCR reactions can be run and separately quantified using the same fluorophore. Specifically, an SMN2 assay yields an unexpected population of droplets with slightly elevated signal in the FAM detection channel.

Figure 10:
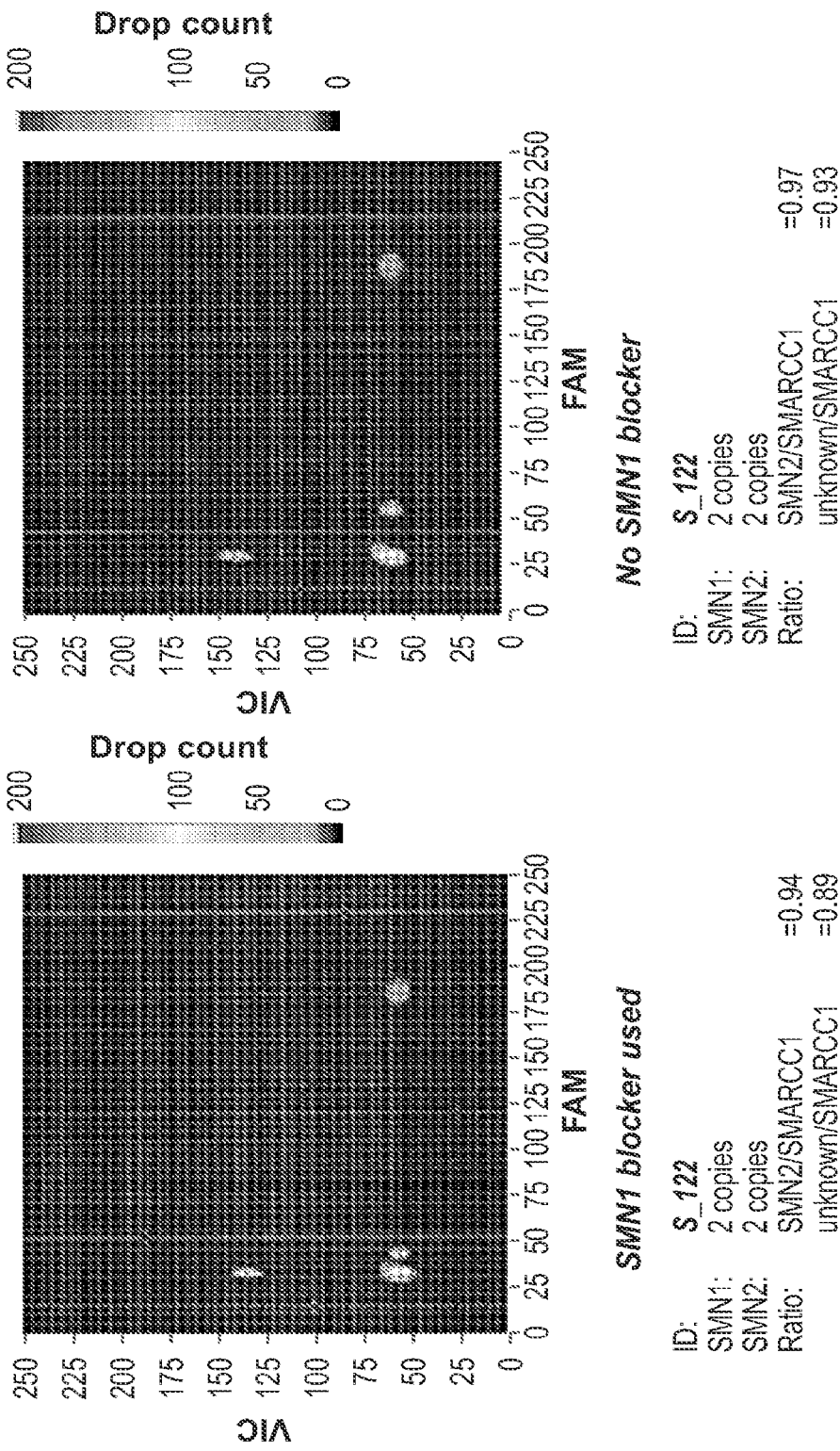
FIG. 10 shows two dot plots depicting clusters of genetic sequences detected through fluorescence intensity. Left panel is a dot plot showing four clusters. Block for SMN1 sequence was present. Top left: microdroplets containing the reference sequence (SMARCC1); bottom left: microdroplets not containing any sequence; bottom middle: microdroplets containing sequence for SMN1; and bottom right: microdroplets containing sequence for SMN2. Right panel is a dot plot showing four clusters. No block for SMN1 sequence was present. Top left: microdroplets containing the reference sequence (SMARCC1); bottom left: microdroplets not containing any sequence; bottom middle: microdroplets containing sequence for SMN1; and bottom right: microdroplets containing sequence for SMN2. The shift of the bottom middle cluster in right panel as compared to left panel confirms that fluorescence intensity provides a very sensitive measurement for the presence of a sequence.

The results are depicted in FIG. 10. The left-side dot plot in FIG. 10 depicts the effect of having the SMN1 blocker present in the reaction. The four clusters depicted in the left-side dot plot are as follows: the top left cluster includes microdroplets containing the reference sequence (SMARCC1); the bottom left cluster includes microdroplets not containing any sequence; the bottom middle cluster includes microdroplets containing sequence for SMN1; and the bottom right cluster includes microdroplets containing sequence for SMN2. The dot plot on the right-side of FIG. 10 depicts four clusters where no SMN1 blocker was present in the reaction: the top left cluster includes microdroplets containing the reference sequence (SMARCC1); the bottom left cluster includes microdroplets not containing any sequence; the bottom middle cluster includes microdroplets containing sequence for SMN1; and the bottom right cluster includes microdroplets containing sequence for SMN2. The shift of the bottom middle cluster in right panel as compared to left panel confirms that fluorescence intensity provides a very sensitive measurement for the presence of a sequence.

Without intending to be bound by any theory, the simplest explanation is that the cluster arises from weak association of the SMN2 probe to the SMN1 gene despite the presence of a blocker to that gene (a nonfluorescent complementary probe to the SMN1 gene).

One definitive confirmation of SMN1 as the source of the unexpected cluster was an observed dependence of the intensity of this feature on the presence of the SMN1 blocker. A clear shift toward higher FAM fluorescent intensities was observed in the absence of the blocker (FIG. 10). In another definitive confirmation the ratio of the SMN1 (putative) population size to the reference size of 0.96 in perfect agreement with expectation (two copies of each) (S_131 sample). Another sample, S_122, with the same number of SMN1 copies yielded a ratio of 0.88 in one run and 0.93 in another, also consistent with the proposed explanation of the unexpected cluster.

Without intending to be bound by any theory, these observations indicate that SMN2 probe binding to SMN1 DNA yields an elevated fluorescent signal. A simple kinetic model explaining this phenomenon assumes that the hybridization of the SMN2 probe to the SMN1 DNA achieves equilibrium at a faster rate than the polymerase fills in the complementary strand. The amount of probe fluorophore that is released in each thermal cycle is therefore proportional to (or even equal to) the number of bound probes. Thus the lower the binding affinity the fewer the number of probe fluorophores that are released. Due to SMN1 sequence mismatch(es) with the SMN2 probe, the affinity of the probe is certainly expected to be lower to SMN1 than SMN2. This model also explains the signal dependence on the sMN1 blocker: the blocker competitively inhibits the SMN2 probe hydrolysis by the polymerase exonuclease activity.

It may also be, however, that the probe hybridization does not reach equilibrium before exonuclease activity. In this case, the association rates would play a more dominant role. Similar logic applies. The binding rate to the matching site is likely to be faster than to the mismatch site, and the blocker would act to decelerate probe binding to the mismatch site. The binding of SMN2 probe to SMN1 DNA might be detectable by conventional bulk qPCR, especially in absence of SMN2, but highly quantitative results like those shown here are very unlikely. Definitely, there is no report of qPCR or any other technique quantifying two different DNA sequence motifs with the same color fluorophore. Sequestration of the individual reactions by single molecule amplification within droplets eliminates any confusion regarding mixed contributions to the signal.

The advantage of quantifying DNA with multiple probes of the same color fluorophore extends beyond the example of two highly homologous sequences shown here. Rather, any plurality of sequences of any degree of similarity or dissimilarity can be quantified so long as the different probes have significantly different binding occupancies to their respective DNA binding sites.

Another advantage of the dPCR approach for multiplexed reactions is that the different reactions do not compete with each other for reagents as they would in a bulk qPCR assay. However, the possibility for unintended cross-reactivity remains. A multiplexes assay can require a more dilute sample. For instance, at 10% occupancy a duplex reaction would have double occupancy 1% of the time. Hence 1 in 10 PCR+ droplets would be doubles, resulting in a final intensity at least as high and possibly higher than the brighter of the two probes. For a simple duplex system the contribution from each probe could be recovered. In this example the total number of PCR+ droplets for probe 1 would be (Probe 1)+(Probe1+Probe2). Higher degrees of multiplexing would require greater dilution. For example, for a 4-plex at 1% occupancy the probability of one probe overlapping any of the other 3 is ~3%, and that error may be too high for some applications. The need for large dilutions strongly favors the large number of dPCR reactions.

In another example of the invention, a single fluorophore (FAM) was used in a gene copy number assay for both the reference and the target DNA. A model system was used with varying concentrations of plasmid DNA to represent a change in the target gene copy number, relative to a reference gene, equivalent to 0-16 copies of the target gene per cell. BCKDHA and SMN2 plasmid DNA served as the reference and target with 1× and 0.5× primers and probes respectively. With a starting ratio of 8:1 SMN2 to BCKDHA, the sample was diluted serially by 2× into a solution of BCKDHA at the same concentration to vary just the amount of SMN2. The resultant samples were emulsified, thermally cycled, and over $10^5$ droplets were analyzed for each sample as described in the previous section. The process was repeated in triplicate.

Figure 11A:
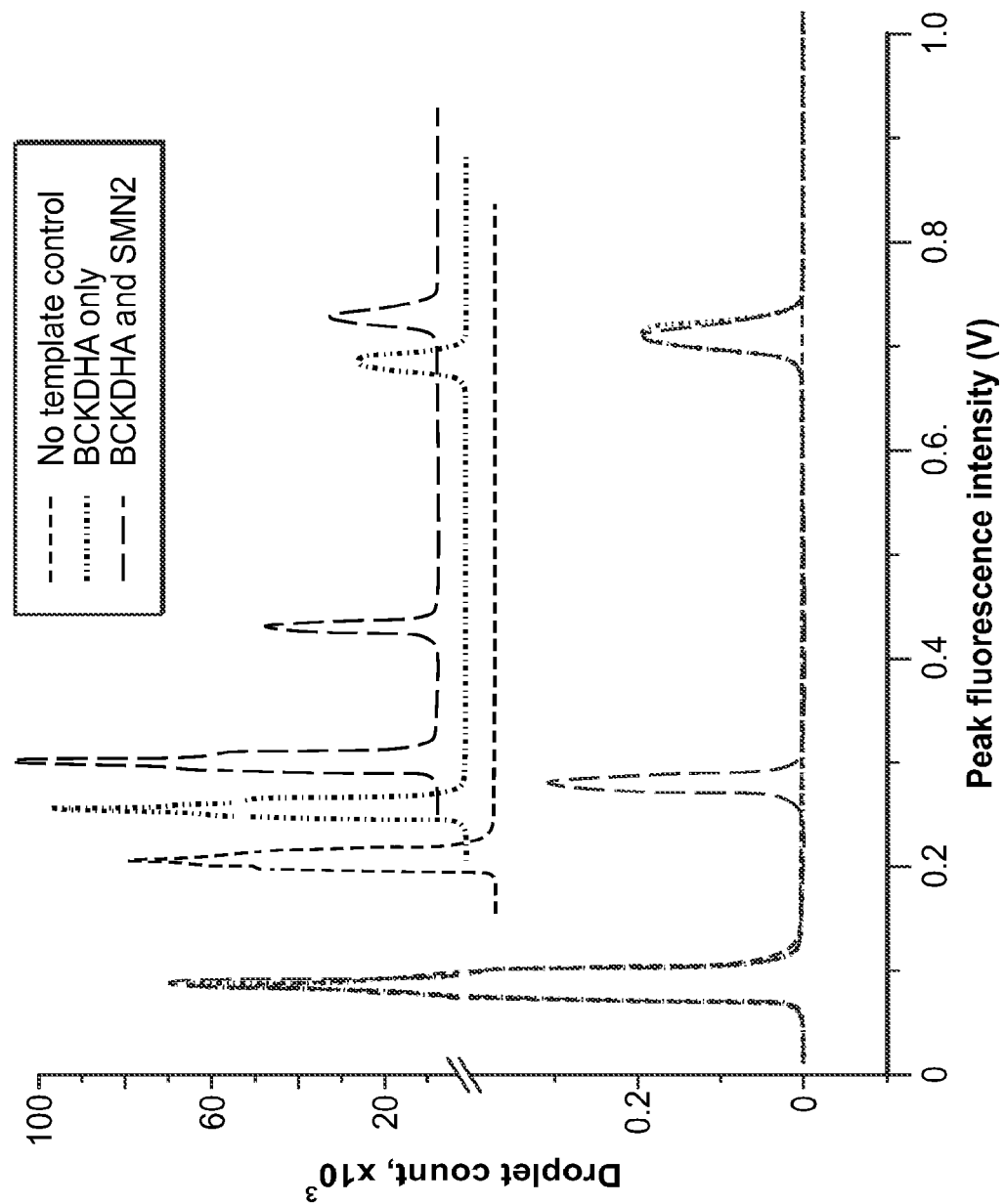
FIGS. 11A-B depict histograms of a duplex gene copy number assay using only one type of fluorophore by digital PCR.
Figure 11B:
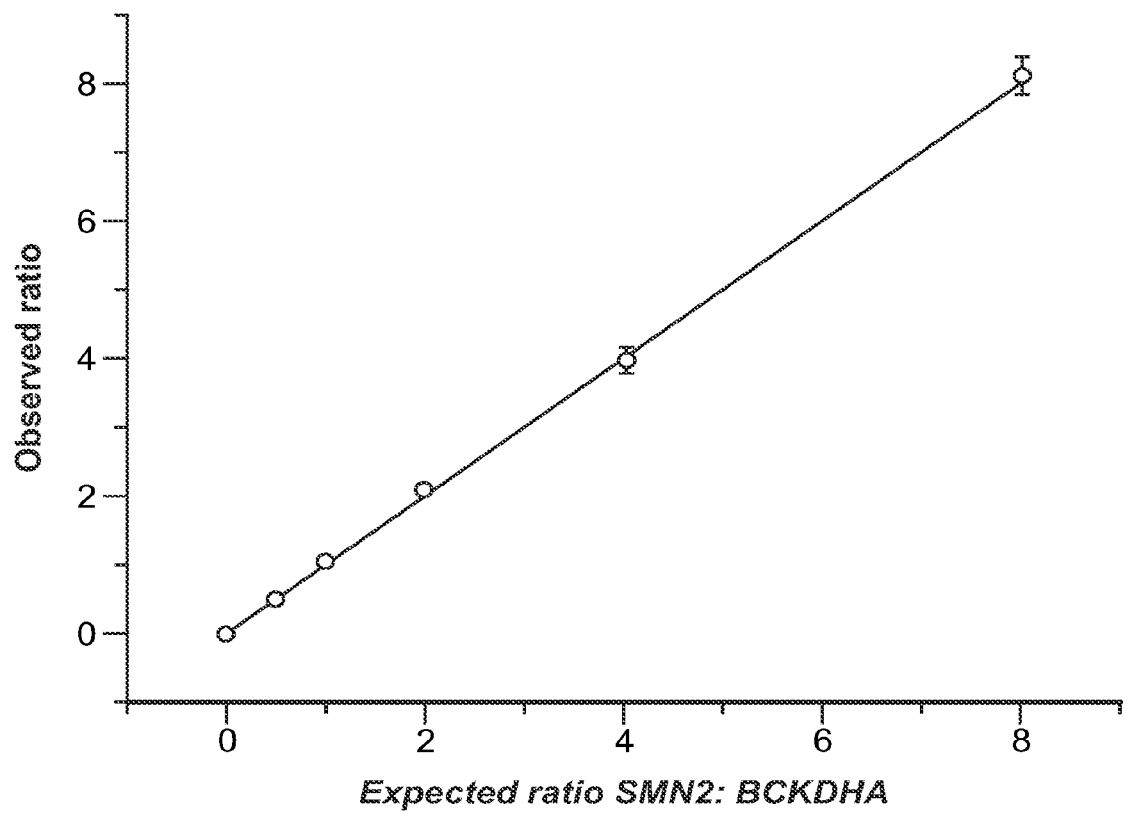

Methods of the invention also include analytical techniques for identification of fluorescence signatures unique to each probe. In this example of the invention, histograms of the droplet fluorescence intensities are shown in FIG. 11a for three different template DNA samples: a no template control (dotted line), BCKDHA only (solid line), and 1:1 BCKDHA to SMN2 (dashed line). For clarity, the histograms are shown both overlapped to highlight the similarity for certain peaks, and offset from each other to reveal all of the features. In the case of 1:1 BCKDHA to SMN2, three populations were readily apparent: a dominant feature appeared at V, and two smaller peaks were evident at 0.27 and 0.71 V. The dominant feature at 0.08 V was assigned to PCR(−) droplets since both small peaks disappeared, but the large one remained, in the no template control. The peak at 0.71 V was assigned to BCKDHA since it was the sole feature arising with the addition of just BCKDHA, and the peak at 0.27 V appeared on subsequent addition of SMN2, completing the assignments. A very small peak appeared at −0.9 V, not visible on the scale of FIG. 11a, that corresponded to droplets occupied by both genes. As another method of the invention, once the different peaks are identified, droplets within each peak were counted corresponding to each possible state (PCR(+) for either BCKDHA or SMN2, or both, or PCR(−)), and the gene copy number was then determined from the ratio of occupancies. Gene copy numbers for each sample in the serial dilution are plotted in FIG. 11b against expected values (observed ratios of SMN2 to BCKDHA to expected ratios of SMN2 to BSKDHA), with an excellent linear fit (y=1.01x) across the full range ($R^2$=0.9997, slope=1.01), demonstrating accurate and precise measurement of the equivalent of 0 to 16 copies of SMN2 per cell.

Detection of Alternatively Spliced Transcripts

The same principle can be used to detect and count alternatively spliced transcripts. TaqMan assays can be designed that are specific for each of the exons in an RNA transcript. After the RNA is turned into cDNA it can be encapsulated into a droplet at 1 copy or less per droplet. The droplet would also contain the multiplexed TaqMan assay for each of the exons. Each of the TaqMan assays would contain a different probe but all the probes would have the same fluorescent dye attached. The droplets would be thermocycled to generate signal for each of the TaqMan assays. If there are multiple splice variants in the sample they each will contain a different number of exons depending on the splicing events. The fluorescent intensity of each droplet would be different depending on the number of exons present. By counting the number of droplets with different intensities it would be possible to identify the presence and abundance of different splice variants in a sample.

Copy Number Variants in a Heterogeneous Sample

It would be possible to determine if a heterogeneous sample contained components with different copy level numbers. If the copy number variants to be assayed were spaced close enough along the chromosome, the DNA from a sample could be fragmented and encapsulated in droplets at a level of one haploid genomic equivalent or less per droplet. The droplet would also contain a TaqMan assay specific for the copy number variant. The intensity of the signal in each droplet would depend on the number of copy number variants are present for the sample. Counting of the number of droplets of different intensities would indicate things like how many cells in a particular sample had what level of copy number variants.

Tuning TaqMan® Probe Fluorescence Intensity

Identifying probes by fluorescence intensity often requires adjusting the brightness of the probes, particularly for higher-plex assays with dense probe patterns. In the previous section the probes for the gene copy number assay yielded very well resolved peaks (FIG. 11a). Clearly room exists to accommodate one or multiple extra probes in the copy number assay within the resolution of the measurement, but a method for adjusting the fluorescence intensity of the new probes is required to avoid interference with the existing assay. One method of the invention involves varying the probe and primer concentrations together as a very simple technique to optimize relative intensities in higher-plex reactions.

FIG. 12 is a schematic for tuning the intensity of a detectable label to a particular target with a microfluidic device. As shown in Panel A of FIG. 12, a template DNA is amplified with two sets of primers: forward primers (F1 and F2) and reverse primers (R1 and R2). Probes (P1 and P2) are labeled with fluorophore of color 1 and bind to target 1 and target 2 respectively. Fluorescence from target 2 is lower in intensity than that from target 1 due to single base mismatch between P2 and target 2. As shown in Panel B, template DNA is amplified with two sets of primers: forward primers (F1 and F2) and reverse primers (R1 and R2) (Panel B). Fluorescence from target 2 is lower in intensity than that from target 1 due to the presence of a competing probe 2 that is not labeled with the fluorophore. As shown in Panel C, template DNA is amplified with two sets of primers: forward primers (F1 and F2) and reverse primers (R1 and R2). Probes (P1 and P2) are labeled with fluorophore of color 1 and bind to target 1 and target 2 respectively. Fluorescence from target 2 is lower in intensity than that from target 1 due to the presence of a competing probe 2 that is labeled with a different fluorophore.

Figure 13:
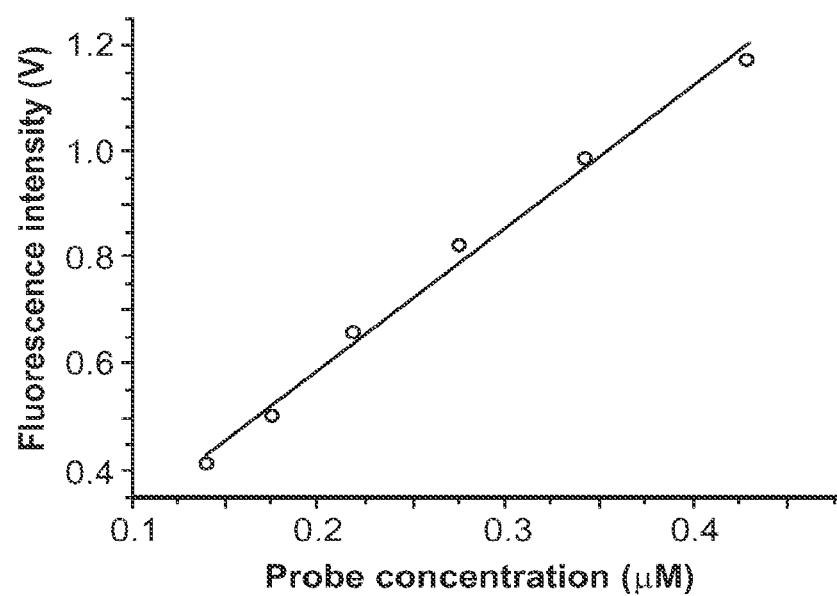
FIG. 13 is a line graph depicting the linear dependence of droplet fluorescence intensity on probe concentration (Line, best linear fit (y=-0.092x+0.082, R.sup.2=0.995).

FIG. 13 shows probe fluorescence intensities throughout a serial dilution of the probes and primers for a different reference gene, ribonuclease P (RNaseP), against a constant amount of genomic DNA from the Coriell cell line NA3814 at an occupancy of 0.02 target DNA molecules per droplet. The probe fluorescent intensities varied in direct proportion to probe concentration over a narrow concentration range spanning ~0.15 to 0.4 µM ($R^2$=0.995)—roughly centered about the typical probe concentration of 0.2 µM—after compensation for dilution errors and other run-to-run differences such as optical realignments using the intensity of the PCR(−) droplets as a reference. In summary, probe intensities can be varied by dilution over a small but adequate range for the purpose of tuning multiplexed assays without affecting the amplification itself.

Although the example above for adjusting probe fluorescence intensities involves varying probe and primer concentrations together by the same factor, the invention is not limited to this method alone for varying probe intensity. Other methods known to those familiar with the art for varying probe intensities are also considered. Such methods include varying just the probe concentration; varying just the primer concentrations; varying just the forward primer concentration; varying just the reverse primer concentration; varying the probe, forward, and reverse primers concentrations in any way; varying the thermal cycling program; varying the PCR master mix; incorporating into the assay some fraction of probes that lack fluorophores; or incorporating into the assay any hybridization-based competitive inhibitors to probe binding, such as blocking oligomer nucleotides, peptide nucleic acids, and locked nucleic acids. The invention incorporates the use of these methods adjusting probe fluorescence intensity, or any other methods for adjusting probe fluorescence intensity, used either by themselves or in any combination.

Higher-Plex Reactions

One method of the invention involves performing higher-plex assays with a single probe color (i.e. fluorophore). As described above, probe fluorescent intensities can be adjusted by a variety of means such that each intensity level uniquely identifies a DNA target. For example, targets T1, T2, T3, and T4 might be uniquely identified by intensity levels I1, I2, I3, and I4. Not intending to be bound by theory, the maximum number of intensity levels possible for unique identification of targets is related to the resolution of the different intensity levels—that is the spread of intensities for each particular probe compared to the separation between the average intensities of the probes—and it is also related to the intensity of the empty droplets that tends to grow with increasing numbers of probes. The number of intensity levels can be 0, or 1, or 2, or 3, or 4, or up to 10, or up to 20, or up to 50, or up to 100. The number of intensity levels can be higher than 100. In the examples show below, as many as three intensity levels are demonstrated.

Another method of the invention involves performing higher-plex assays using multiple different probe colors (i.e. fluorophores). As above for the monochromatic multiplexing assay, for each color probe, multiple targets can be identified based on intensity. Additionally, multiple colors that are spectrally separable can be used simultaneously. For example, a single droplet might contain four different probes for measuring four different targets. Two probes might be of color A with different intensities (say, A1 and A2), and the other two probes of color B with different intensities (say B1 and B2). The corresponding targets are T1, T2, T3, and T4 for A1, A2, B1, and B2 respectively. If a droplet shows an increase in fluoresce in color A, the droplet therefore contained either targets T1 or T2. Then, based on the fluorescence intensity of color A, the target could be identified as T1 or the target could be identified as T2. If, however, a droplet shows an increase in fluorescence in color B, the droplet therefore contained either targets T3 or T4. Then, based on the fluorescence intensity of color B, the target could be identified as T3 or the target could be identified as T4. Not intending to be bound by theory, the maximum number of different colors possible is limited by spectral overlap between fluorescence emission of the different fluorophores. The maximum number of colors can be 1, or 2, or 3, or 4, or up to 10, or up to 20. The maximum number of colors can be higher than 20. In the demonstrations that follow, the largest number of colors is two.

Another method of the invention involves performing higher-plex assays using multiple different probe colors (i.e. fluorophores), however unlike the strategy above where each target is identified by single type of probe with a unique color and intensity, instead in this method a single target may be identified by multiple probes that constitute a unique signature of both colors and intensities. For example, a single droplet might contain four different probes for measuring three different targets (say, T1, T2, and T3). Two probes might be of color A (say, A1, and A2), and two probes might be of color B (say, B1 and B2). T1 is measured by probe A1, T2 is measured by probe B1, but T3 is measured by both probes A2 and B2. Thus, when a droplet contains T1 only increased fluorescence appears in color A. When a droplet contains T2 only increased fluorescence appears in color B. However when a droplet contains T3, increased fluorescence appears in both colors A and B.

Generally, without wishing to be constrained by theory, the above three methods for higher-plex dPCR are simplest to implement under conditions of terminal dilution, that is when the probability of multiple different target molecules co-occupying the same droplet is very low compared to the probability of any single target occupying a droplet. With multiple occupancy arises the complexity of simultaneous assays competing within the same reaction droplet, and also complexity of assigning the resulting fluorescence intensity that involves a combination of fluorescence from two different reaction products that may or may not be equal to the sum of the two fluorescence intensities of the individual reaction products. However, methods of the invention can accommodate these complications arising from multiple occupancy.

Methods of the invention for higher-plex reactions also include methods for primer and probe pairing. In the simplest case targets are unlikely to reside on the same DNA fragments, such as when targets are from different cells; or when targets are from different chromosomes within a single cell type; or when targets are distant from each other within a single chromosome such that they become physically separated during DNA fragmentation; or when targets are very close to each other within a chromosome, but nevertheless become separated by targeted cleavage of the DNA, such as by restriction enzyme digestion; or for any other reason. In such cases each probe can be paired with a single set of primers (forward and reverse). However, in other cases the target regions might frequently reside on the same DNA fragments, for example when targets reside within the same codon, or for any other reason. In such cases, a single set of primers might serve for multiple probes (for an example, see Pekin et al.).

Figure 22:
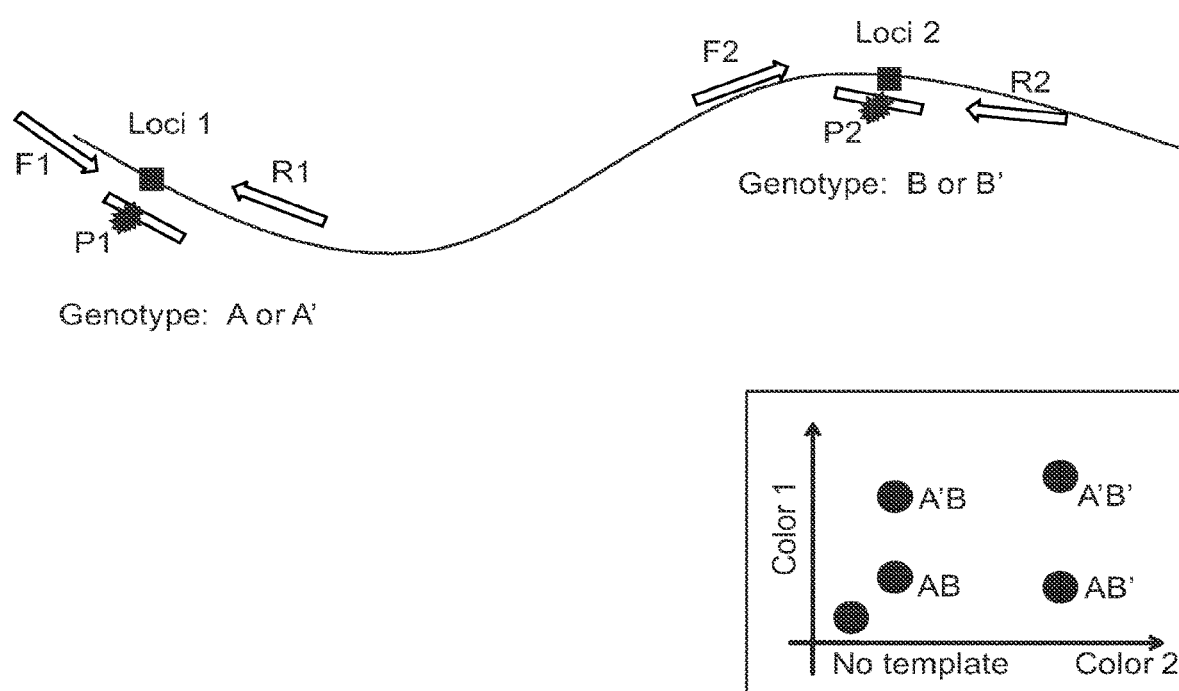
FIG. 22 is a schematic showing haplotype detection in droplets.

Higher multiplex reactions can be performed to distinguish the haplotypes of two SNPs. For example, assume that at position one there can be genotypes A or A' and at position two there can be genotypes of B or B'. In a diploid genome four unique haplotypes are possible (A,B; A,B'; A',B; and A',B'). If for example A' and B' represent drug resistant mutations for infection, it is often the case that A'B and AB' are less sever and treated differently than A'B' which represents a significant drug resistance that must be treated with extreme care. Digital PCR with intensity discrimination is ideally suited for identifying low prevalence of A'B' in a background of mixtures of the other three haplotypes. Haplotyping information is also important for construction of haplotypes in HLA. One way that the present example can be constructed is by assay design such that color one is used for A and is of high or low intensity indicative of allele A or A' respectively and color two is used for B and is of high or low intensity respectively indicative of B or B'. Populations of [color1,color2] corresponding to [Low, Low] would be a measure of an allele of AB and [high, low] allele A'B and an allele of [A'B'] will be readily distinguishable as [high, high] even in a background that is predominately a mixture of A'B and AB'. See FIG. 22. In some cases it will be advantageous to start by encapsulating into the droplets long single molecules of nucleic acid that contain both A and B SNP location and in other cases it will be desirable to start by encapsulating single cells, bacteria or other organism within the droplets prior to releasing the nucleic acid from the organism. In still other embodiments the multiplex intensity detection of multiple simultaneous targets can be used as surrogate markers for multiple types of binding interactions or labeling of target materials. This technique is also not limited to single molecule detection and can be used for haplotype detection in single cells (e.g., bacteria, somatic cells, etc.). In single cell analysis, a sorting step may be applied prior to haplotyping.

5-Plex Assay for Spinal Muscular Atrophy

An aspect of the invention was reduced to practice in an example demonstration of the quantitation of several genetic markers for spinal muscular atrophy (SMA). SMA was selected for one of the example demonstrations due to both its important clinical significance as well as its complicated genetics. It is the second-most prevalent fatal neurodegenerative disease and affects ~1 in 10,000 live births. SMA is most often caused by homozygous absence of exon 7 within the survival of motor neuron 1 gene (SMN1, reviewed by Wirth et al.), however the severity of the condition is modulated by the number of gene copies of SMN2 with prognosis ranging from lethal to asymptomatic over 1-5 copy numbers (reviewed by Elsheikh et al.). Hence accurate quantitation of SMN2 copy number is important for clinical prognosis and genetic counseling. Aside from large deletions of SMN1, a number of single point mutations or short deletions/duplications within the same gene also account for ~4% of cases of SMA. In a significant step toward a comprehensive SMA assay, the multiplexed dPCR assay demonstrated here contains both copy number assays (for SMN1 & 2) and an assay for one of the prevalent SNPs (c.815A>G).

One embodiment of the invention is a 5-plex assay for SMA diagnostics. The 5-plex assay quantifies common genetic variants impacting SMA including two copy number assays for the SMN1 and SMN2 genes with BCKDHA as a reference, and a SNP assay for the c.815A>G mutation. Two differently colored fluorophores, FAM and VIC, were used to uniquely identify each of the assays. The probes for SMN1 and SMN2 contained only FAM, and for c.815A only VIC. However, mixtures of VIC and FAM-labeled probes were used for BCKDHA and c.815G. The use of VIC and FAM fluorophores in this example does not limit the invention, rather the assay can be used with any spectrally separable fluorophores compatible with the TaqMan assay, or any other fluorogenic hybridization-based probe chemistries. For validating the assay, a model chromosome was synthesized containing a single target region for each of the different primer/probe pairs. EcoRV restriction sites flanked each target, allowing separation of the fragments.

Figure 14A:
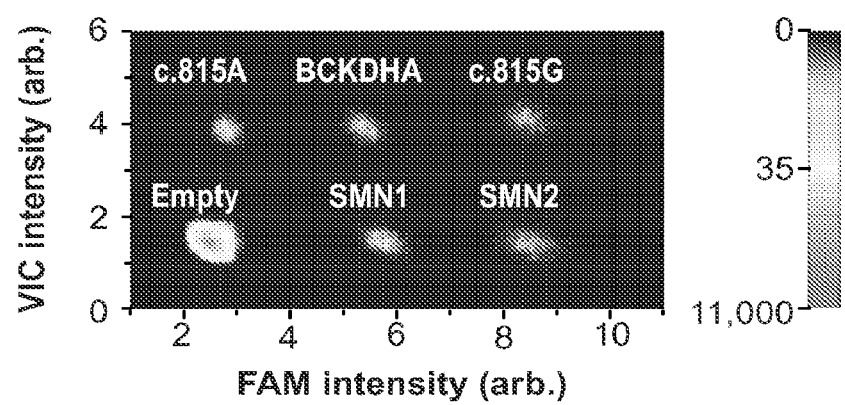
FIGS. 14A-B depicts a 5-plex dPCR assay for spinal muscular atrophy with only two fluorophores.

As another method of the invention, histogram-based data presentation and analysis is incorporated into the invention for identifying and characterizing statistically similar populations of droplets that arise from one probe signature (color and intensity), and for discriminating one population of droplets from the others. FIG. 14a shows a 2-dimensional histogram of droplet fluorescence intensities as a contoured heat map, with hotter colors representing higher occurrences. Standard techniques were used to compensate for spectral overlap of the FAM and VIC signals. Samples were run at 0.006 occupancy per target. Six populations were clearly evident, five for the assay and one for PCR(−) droplets. As one method of the invention, the populations were assigned by selective exclusion of assay components. For example, excluding the SMN2 primers and probe eliminated the population at the bottom right in the histogram, but otherwise the distribution remained unchanged. Assignments are labeled in FIG. 14a. As we have found to be generally true for this method of multiplexing, the assay worked immediately with well resolved or at least distinguishable populations for each target. As another method of the invention, the relative positions of the different populations in the histogram were then adjusted into a regularly spaced rectangular array by tuning the probe concentration as described in the previous section. Usually no more than two iterations are required for optimization.

Figure 14B:
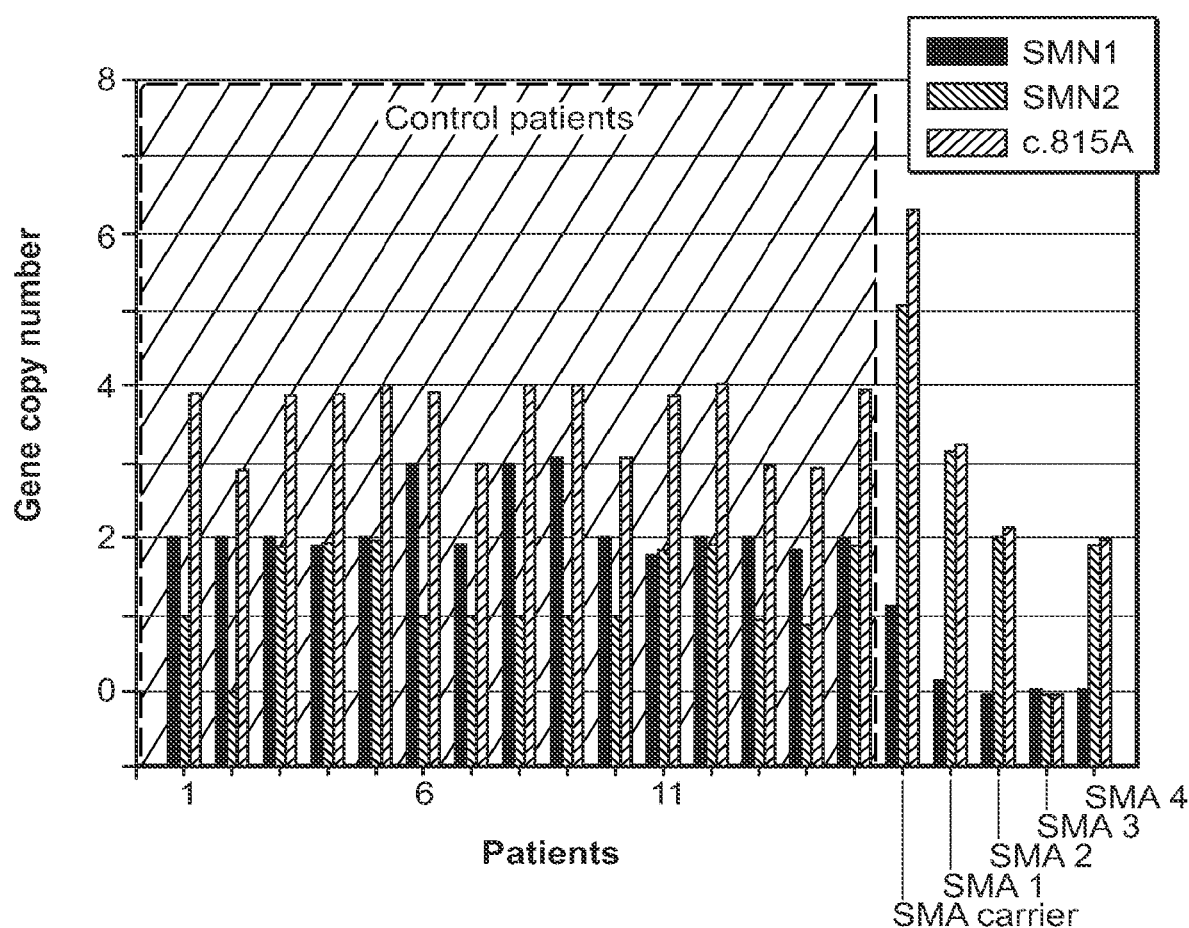

In another method of the invention, the different populations were sufficiently well resolved to allow droplets within each population to be counted by integration across rectangular boundaries. The boundaries were positioned at mid-sections between neighboring peaks. The methods of the invention are not constrained to rectangular boundaries, or to specific boundary locations between peaks. Rather, any closed or unclosed boundary condition can suffice. Boundary conditions do not need to be "binary" either, in the sense that weighted integrations can also be performed across the boundaries to arrive at droplet counts. The peak position of each cluster varied by no more than 2% from run to run after normalization to the intensity of the empty droplets to account for variations in detection efficiency (data not shown). Hence, once identified, the same boundaries for integration could be reused between samples. The methods of the invention are not limited to fixed boundary positions. Dynamic population identification and boundary selection in between samples or studies is anticipated. Twenty different patient samples from the Coriell cell repositories were analyzed with this assay: 4 afflicted with SMA, 1 SMA carrier, and 15 negative controls. Assay results are shown in FIG. 14b. Gene copy number was calculated as before, as the ratio of occupancies derived from the number of target droplets vs. reference droplets. Like the copy number measurement in FIG. 11, each assay yielded ratios very close to the expected integer values, but when all of the patient data was plotted as actual ratio vs. expected integer ratio a small systematic deviation from the ideal slope of 1 was observed. Measured slopes were 0.92, 0.92, and 0.99 for SMN1, SMN2, and c.815A respectively. For clarity, the data in FIG. 14b was scaled to the ideal slope of 1.

The measured genotypes of the different patients were consistent with their disease conditions (unafflicted, carrier, or afflicted). The patients afflicted with SMA each had zero copies of SMN1 (numbers SMA 1-4 in FIG. 14b), the carrier had just one copy, and the negative controls all had two or three copies (numbers 1-15). Three unrelated individuals (numbers 6, 8, and 9) had three copies of SMN1, occurring at a rate of 20% which is similar to a previous report for healthy individuals. Variability in SMN1 copy number is not surprising since it lies within an unstable region of chromosome 5q13. A larger variety of SMN2 copy numbers was observed. One to two copies were most common in the control group, although one individual had zero copies, a distribution consistent with expectations for normal individuals. The SMA carrier and afflicted patients had elevated copy numbers of SMN2 on average: 5 for the carrier, two afflicted with 3 copies, and the others with 2 copies. The afflicted patients were all diagnosed as SMA Type I, the most severe form, based on clinical observations according to the Coriell repository. The strong genotype/phenotype correlation between SMN2 copy number and disease severity suggests that the two individuals with three copies of SMN2 might have an improved Type II prognosis, especially for the patient SMA 1 who had survived to three years at the time of sampling, much beyond the typical maximum life expectancy for SMA Type I of 2 years. However there remains reluctance to predict disease outcome based on SMN2 copies alone since other less well characterized or unknown modifying genes may impact prognosis and because not all SMN2 copies may be complete genes. Furthermore some Type I patients have begun surviving longer in newer clinical settings. Hence, with little clinical information regarding the patients available to us, we can conclude that our SMN2 assay results were consistent with broad expectations for disease severity.

The SNP assay revealed that all patients carried the normal c.815A genotype and no instances of c.815G were observed. The mutation is relatively rare and hence was not expected to appear in a small patient panel. Of interest, however, was the presence of an apparent extra gene fragment in two unrelated individuals that was uncovered with the SNP assay. The c.815A>G assay does not discriminate between SMN1 and SMN2 due to their high sequence similarity, and hence the total copies of c.815A and G should equal the sum of the copies of SMN1 and SMN2. This was true for all patients except for healthy patients number 1 and 2, both of whom had one extra copy of c.815A. c.815 lies on exon 6, and the SNP that discriminates between the SMN1 and SMN2 genes lies on exon 7, hence the extra genes may be fragments of SMN1 lacking exon 7. This seems reasonable because the deletion of exon 7 is the common mutation causing 95% of cases of SMA (reviewed by Wirth et al.) and it is carried by 1/40 to 1/60 adults. Thus these patients might have been typical carriers of SMA but for the acquisition of at least one compensating healthy copy of SMN1 on the same chromosome.

9-Plex Assay for Spinal Muscular Atrophy

Figure 15:
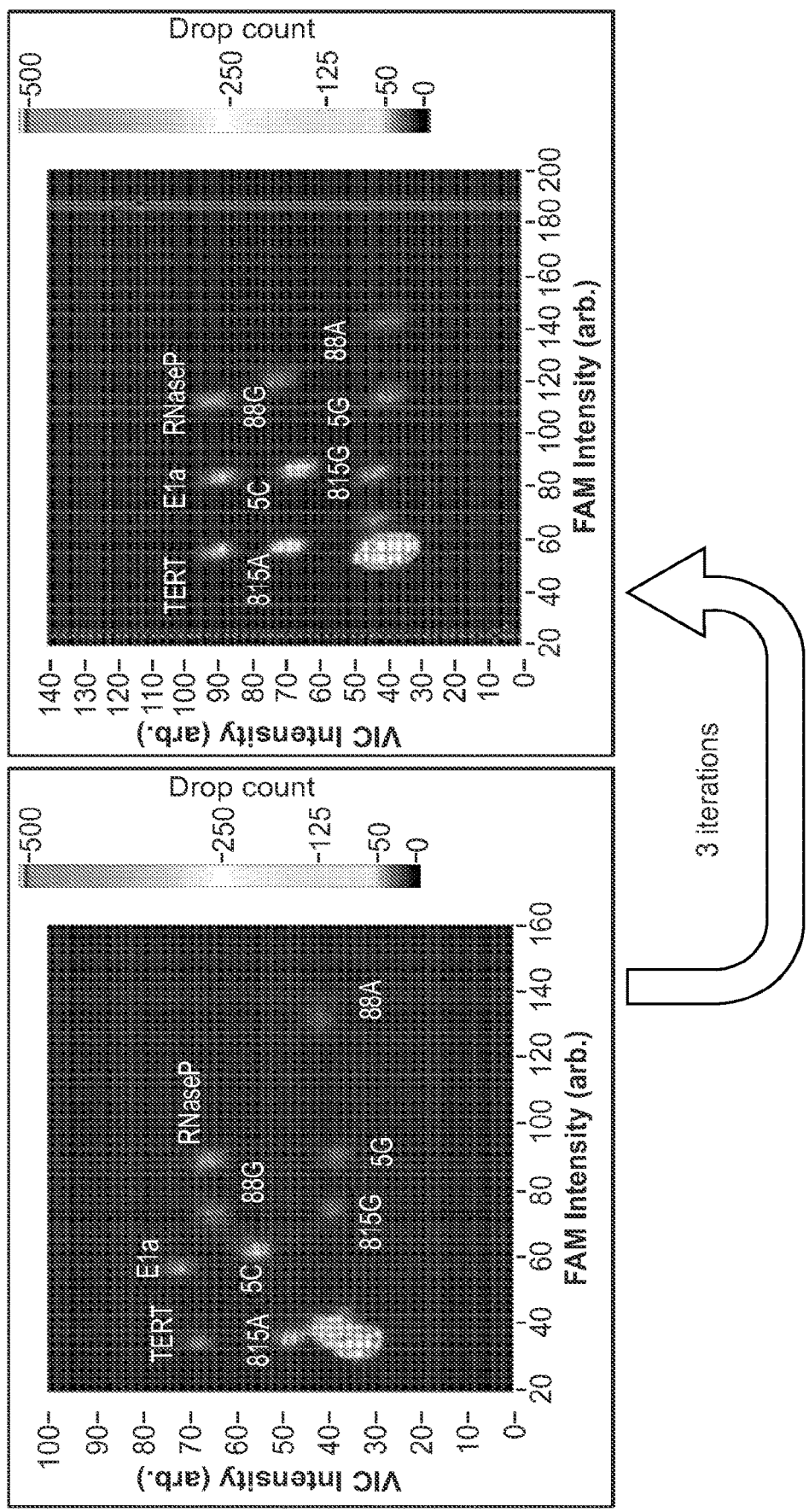
FIG. 15 depicts a 9-plex dPCR assay for spinal muscular atrophy with only two fluorophores, showing the process of optimizing droplet intensities.

A 9-plex assay for certain SMA related targets was also demonstrated with just two colors (probes containing FAM and VIC fluorophores). Aside from the optimized primer and probe concentrations, assay conditions and experimental procedures were identical to the 5-plex assay above. FIG. 15a shows the various droplet populations in 2-D histograms before optimization of probe concentrations. The identity of the different targets is shown on the figure itself. As one method of the invention, the identification of the populations was made as before, by selective exclusion and/or addition of one or more assays. Most of the populations were already well resolved, with the exception of the probe for the c.815A genotype that was in close proximity with the cluster corresponding to empty droplets. After three iterations of optimization of probe concentrations, all of the target populations were well resolved from each other, and well resolved from the empty droplets (FIG. 15b). Three methods of the invention were highlighted in this demonstration: (1) nine DNA targets were uniquely identified in a two-dimensional histogram, far beyond the capabilities of conventional qPCR; (2) target DNA molecules were distinguished on the basis of some combination of both color and intensity arising from one or multiple probes against the same target; and (3) the relative positions of the target molecules within the histogram were adjusted by varying the probe concentrations to optimize the pattern of colors and intensities for increased resolution amongst the various droplet populations.

As one method of the invention, different droplet populations were identified by selective addition or exclusion of assays in the examples above. However the invention is not limited to this method alone. Rather, any method for population assignments known to those in the art are considered. Methods of the invention include any method that can cause an identifiable displacement, appearance, or disappearance of one or more populations within the histograms including changing the probe and primer concentrations together, either by the same factor or by different factors; changing the probe concentration alone; changing the primer concentrations alone; changing the thermal cycling conditions; and changing the master mix composition. Another method of the invention takes advantage of prior knowledge of the position of an assay within a histogram to assist assignment.

Multiplexing Capacity

The level of multiplexing demonstrated in the preceding SMA example was 9×, significantly exceeding the maximum practicable number with qPCR. Without wishing to be constrained by theory, the two main limitations are the resolution between assays and the increasing fluorescence intensity of empty droplets with higher loading of probes. A method of the invention involves optimizing the pattern of colors and intensities of the different probes for maximum multiplexing while still achieving adequate specificity for each individual reaction. Although rectangular arrays of droplet populations were demonstrated for the 5- and 9-plex reactions, another desirable pattern is the tight-packed hexagonal array. However the invention is not constrained to any particular array strategy.

Adding extra colors would increase the capability even further, however with some diminishing returns because the fluorescence of the empty droplets would continue to rise. The capacity could be yet further increased with better probes yielding larger differential signals, such as hybrid 5'-nuclease/molecular beacon probes that reduce background by contact quenching yet exhibit the bright signals typical of free unquenched fluorophores. With such improvements multiplexing capacity exceeding 50× can be envisioned.

Combined Multiplexing with Optical Labeling

Using droplet-based microfluidics, multiple targets can also be measured simultaneously by a different method. According to the alternative method, primers and probes can be loaded individually into droplets along with an optical label to uniquely identify the assay. Typically the optical label is a fluorophore, or a combination of different fluorophores, that are spectrally distinct from the probe fluorophore. Various different types of droplets, each containing different assays that are uniquely identified by different optical labels, can be mixed into a "library" of droplets. Then, according to methods of the invention above, library droplets are merged one-to-one with droplets containing template DNA. After thermal cycling, some droplets that contain template DNA will exhibit brighter fluorescence at the emission wavelengths of the probes. The specific target DNA molecules giving rise to these PCR(+) signals are subsequently identified by the optical probes. In one study, the six common mutations in KRAS codon 12 were screened in parallel in a single experiment by one-to-one fusion of droplets containing genomic DNA with any one of seven different types of droplets (a seven-member library), each containing a TaqMan® probe specific for a different KRAS mutation, or wild-type KRAS, and an optical code.

In one method of the invention, optical labeling can be combined with the various methods for multiplexing dPCR already incorporated into this invention. For example, a single optical label might code for the entire 5-plex SMA assay, above, instead of just a single assay as in the KRAS example above. In this manner, other optical labels might code for different screening assays for newborn infants. According to other methods of the invention, above, a single DNA sample from an infant could then be analyzed with all of the assays simultaneously by merging droplets containing the DNA one-to-one with library droplets containing the optically encoded assays.

Figure 16:
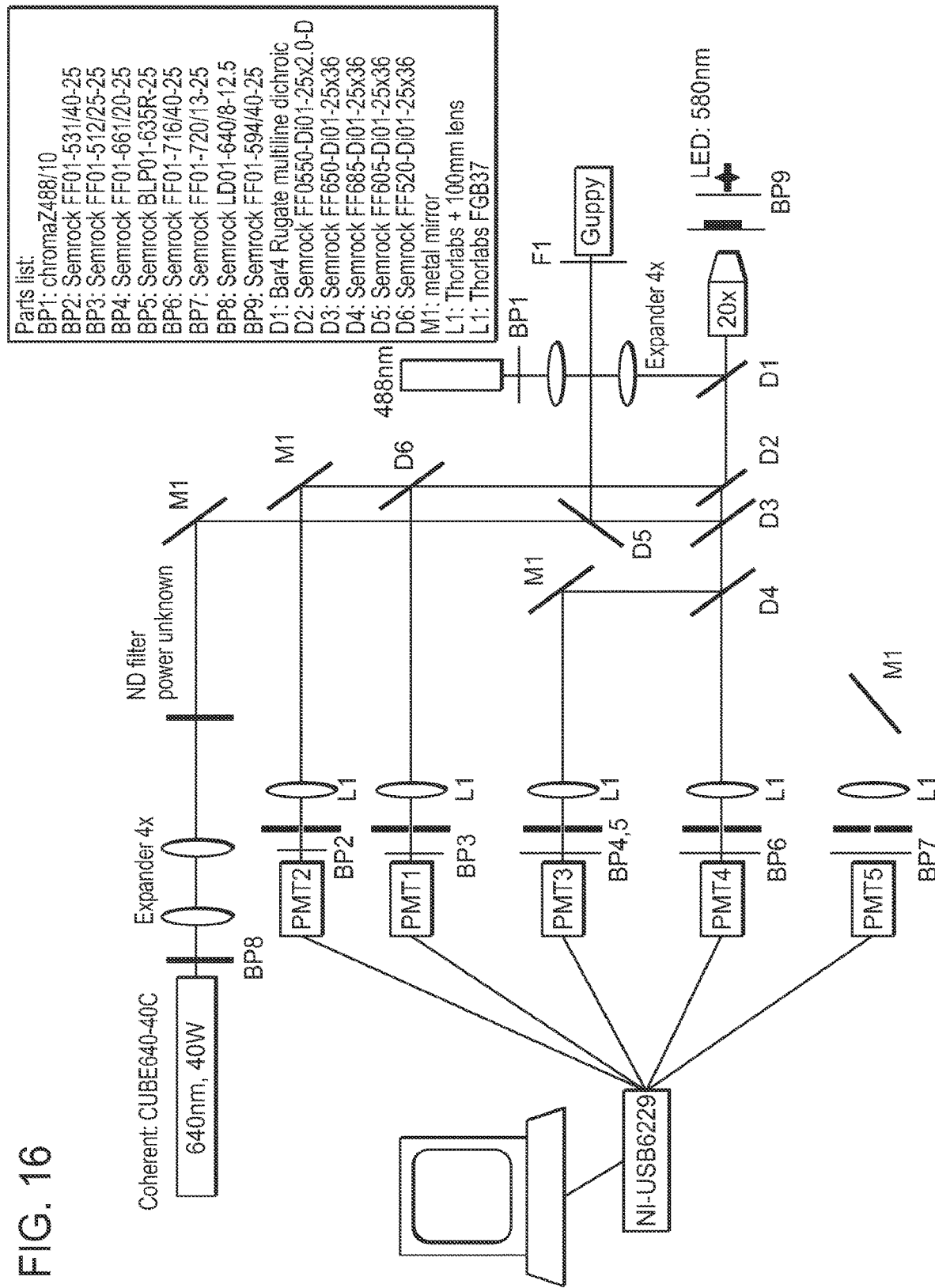
FIG. 16 depicts an optical schematic for combining optical labels with multiplexing.

As an example of combining multiplexing with optical labels, a so called 3×3×3 combination multiplex reaction with optical labeling was demonstrated (3×3 optical labeling with two fluorophores, each encoding a triplex assay, for a total of 27-plex). Two fluorophores were employed for optical labeling, Alexa633 and CF680 (excited by a 640 nm laser), with three intensity levels each producing nine total optical labels. As before with the 5- and 9-plex assays for SMA, TaqMan assays were used with FAM and VIC fluorophores (excited by a 488 nm laser). The fluorescence from the FAM and VIC fluorophores were recorded simultaneously with the fluorescence from the optical labels, requiring modifications to the optical layout of the instrumentation described for the SMA assay (the optical schematic for two-laser excitation and 4-color detection is shown in entirety in FIG. 16). Also, co-flow microfluidics were used in this example (the use of co-flow based microfluidics for this application is one of the methods of the invention described above). In this case, the template DNA was introduced into the chip in one flow, and the PCR master mix, the primers and probes for one triplex assay, and the unique composition of fluorophores for the optical label were introduced into the chip in another flow simultaneously. The two flow streams converged in a fluidic intersection upstream from the droplet forming module, and thus each droplet formed contained the contents of both flow streams. Methods to implement co-flow microfluidics are well known to those in the art. The droplets were collected, and then the procedure was repeated with the next triplex assay and optical label. The procedure was repeated a total of nine times, once for each pair of assays and optical labels. All of the droplets were collected into a single PCR tube and thermally cycled off chip. The mixture of thermally cycled droplets was reinjected into the same read-out chip as used for the SMA assay, above, and the fluorescence intensities of the assays from all four fluorophores was recorded.

Figure 17:
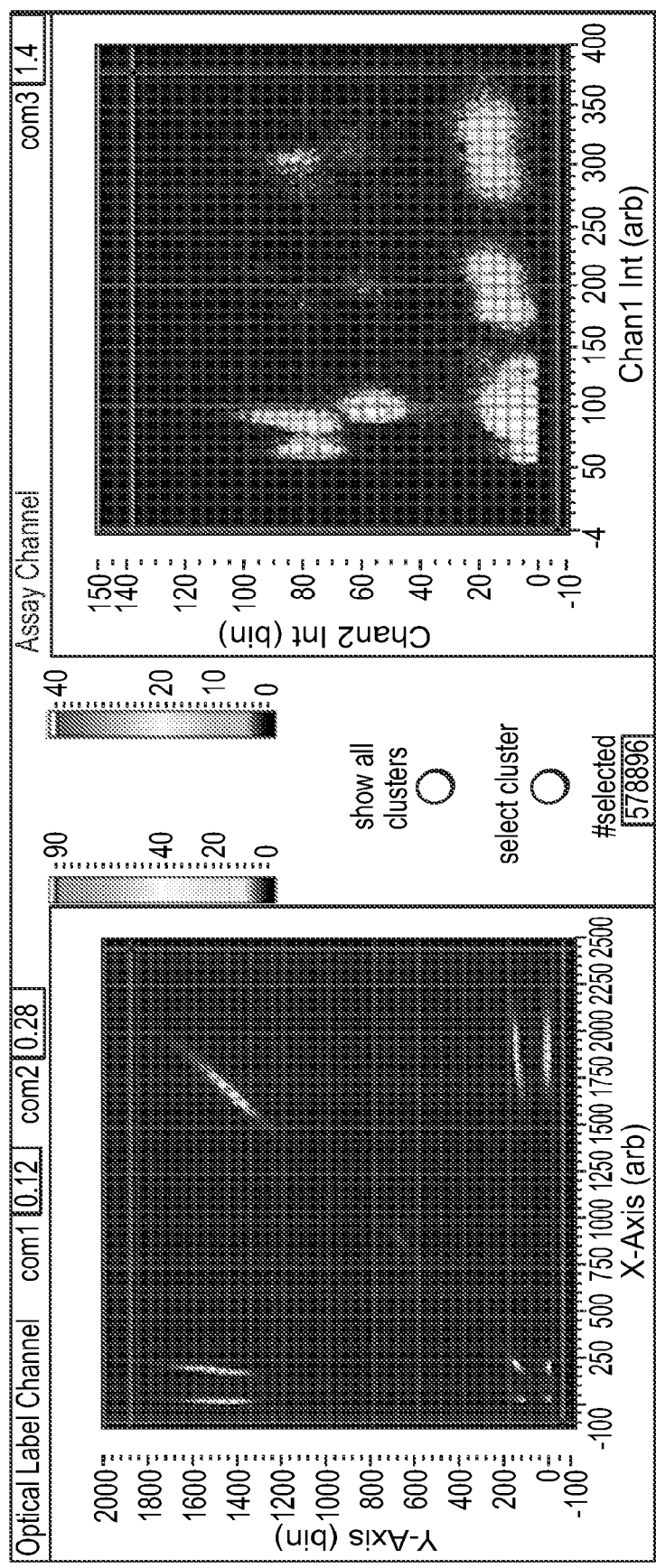
FIG. 17 depicts a dPCR assay combining multiplexing with optical labels using co-flow microfluidics. The contributions from all droplets are shown, that is, from three different triplex assays. (Both panels) 2-D histograms shown as heat maps with hotter colors representing higher droplet counts. (Left panel) histogram of optical labels, i.e. fluorescence intensities of droplets measured at wavelengths for the two fluorophores comprising the optical labels. (Right panel) assay histogram, i.e. fluorescence intensities of droplets measured at wavelengths suitable for FAM detection (x-axis), and VIC detection (y-axis). Both histograms were compensated for spectral overlap by standard techniques.

FIG. 17 shows the cumulative results from all droplets in the 3×3×3 assay using co-flow microfluidics. The figure shows two 2-D histograms of droplet fluorescence intensities, the histogram on the left from all of the optical labels, and the histogram on the right from the assays. Standard methods were used to compensate for spectral overlap. The histograms are shown as a heat maps, with hotter colors designating larger numbers of droplets. Nine different clusters of droplets were clearly evident in the histogram of the optical labels, corresponding to each of the nine different optical labels: there is a small group of four clusters at the bottom left corner of the histogram, corresponding to optical labels with the lowest fluorescent intensities; and there are five clusters appearing as linear streaks at the higher intensities. The droplet clusters were less distinct in the histogram for the assay, but this was as expected because the droplets shown contained all of the triplex assays. The individual assays became clearly distinct once a single type of assay was selected by using the optical labels, as follows.

Methods of the invention involve selecting individual populations of droplets all containing the same optical labels, or groups of optical labels. In some methods of the invention, boundaries of fluorescence intensity were used to specify populations. In the example shown here, a rectangular boundary was used specifying the minimum and maximum fluorescence intensities for each fluorophore. However the methods of the invention are not restricted to rectangular boundaries. Any boundary, closed or unclosed, can be employed. Furthermore, according to methods of the invention, selections of droplet populations can be made by any method, and is not restricted to threshold-based methods such as boundary selection.

Figure 18A:
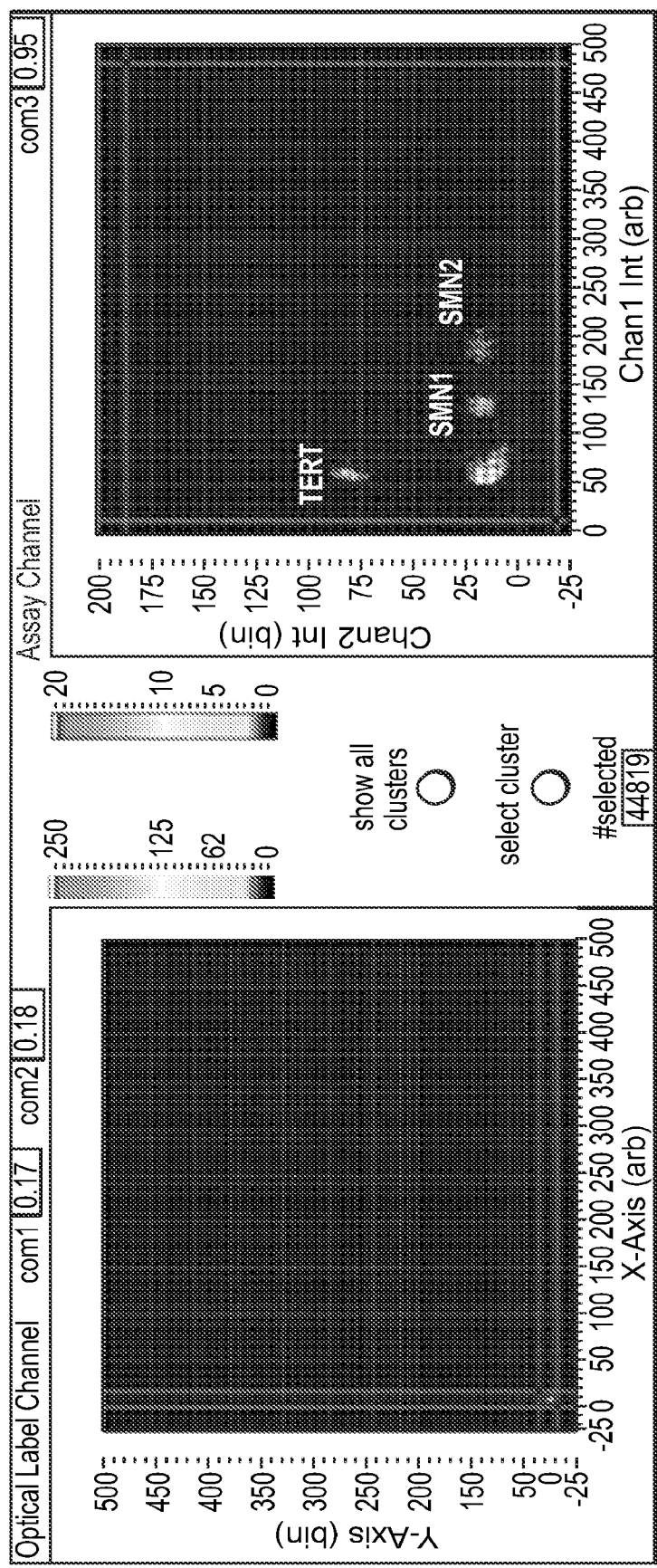
FIGS. 18A-C show single assay selections using optical labels. Selections were taken from all of the droplets from FIG. 17. Each of the three different selections in panels A-C were for optical labels encoding the same assay (TERT, SMN1, and SMN2). Histograms are as described in FIG. 17. (Left histograms, optical labels) Superimposed lines demark the bounding box for selecting a single optical label. (Right histograms, assay) Only droplets containing the selected optical label are displayed.
Figure 18B:
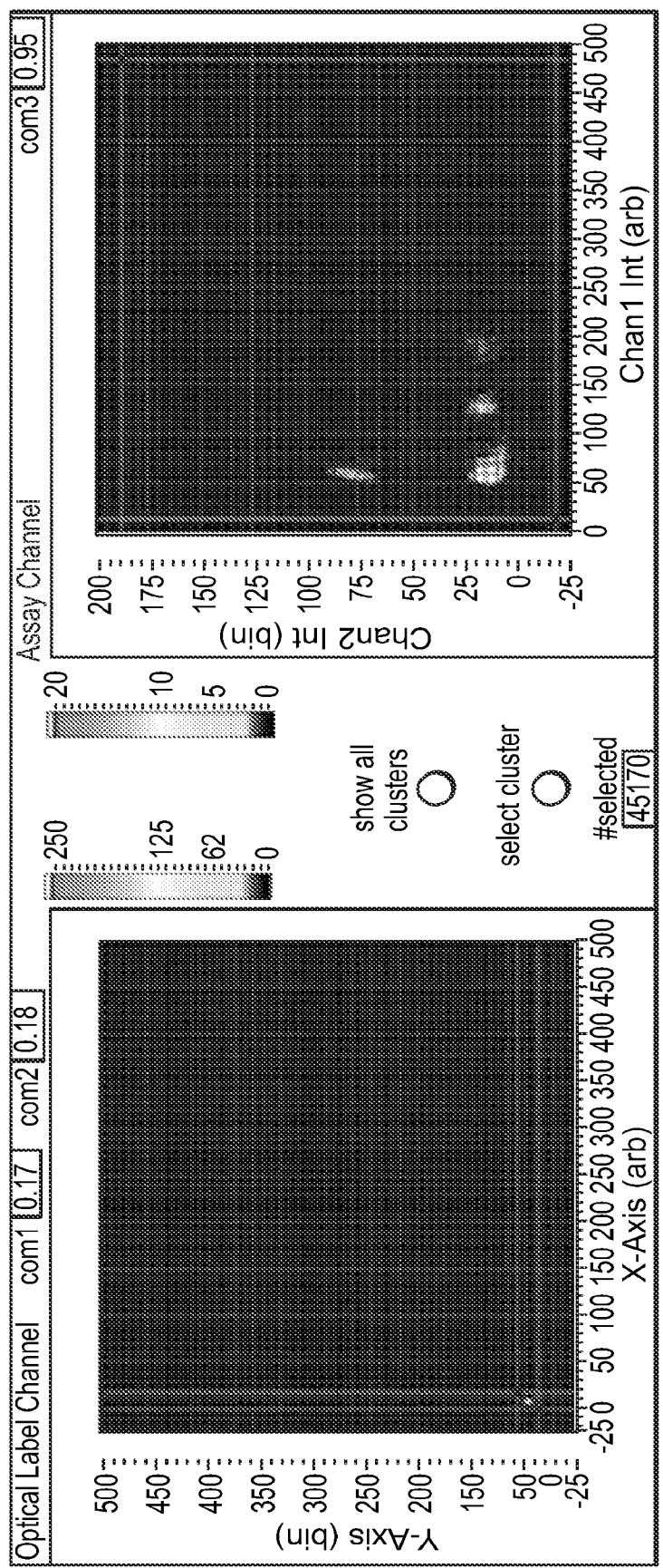
Figure 18C:
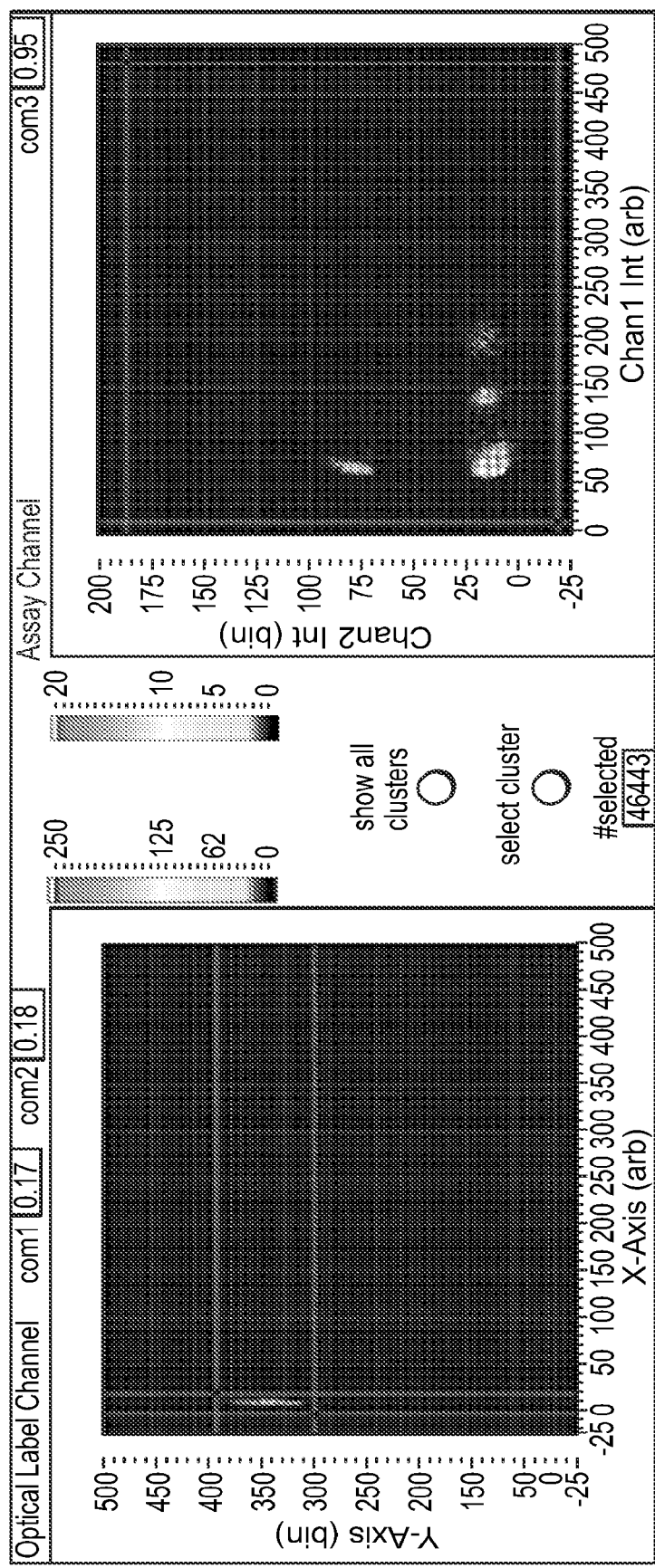

FIG. 18A shows the droplet fluorescence intensities for the assay (right histogram) when only one optical label was selected (left histogram). The lines overlaid on the histogram of the optical labels identify the rectangular boundary used to select just the optical label with the lowest fluorescence for both fluorophores. Both histograms showed only the droplets that were selected. After selection, four distinct clusters of droplets appeared in the assay histogram, three for the different assays (in this case, assays for SMN1, SMN2, and TERT, where TERT is another common reference gene) and one for the empty droplets. The copy numbers for SMN1 and SMN2 were measured by the same methods of the invention as described above for the SMA assay, with values of 1.8 and 0.94 close to the expected values of 2 and 1, respectively. The same assay was encoded with two other optical labels, and their selections are shown in FIGS. 18B and C. Similar results were achieved, with an overall measurement of 1.9±0.1 and 0.9±0.1 copies of SMN1 and SMN2 respectively, showing the measurement to be accurate within experimental uncertainty.

Figure 19A:
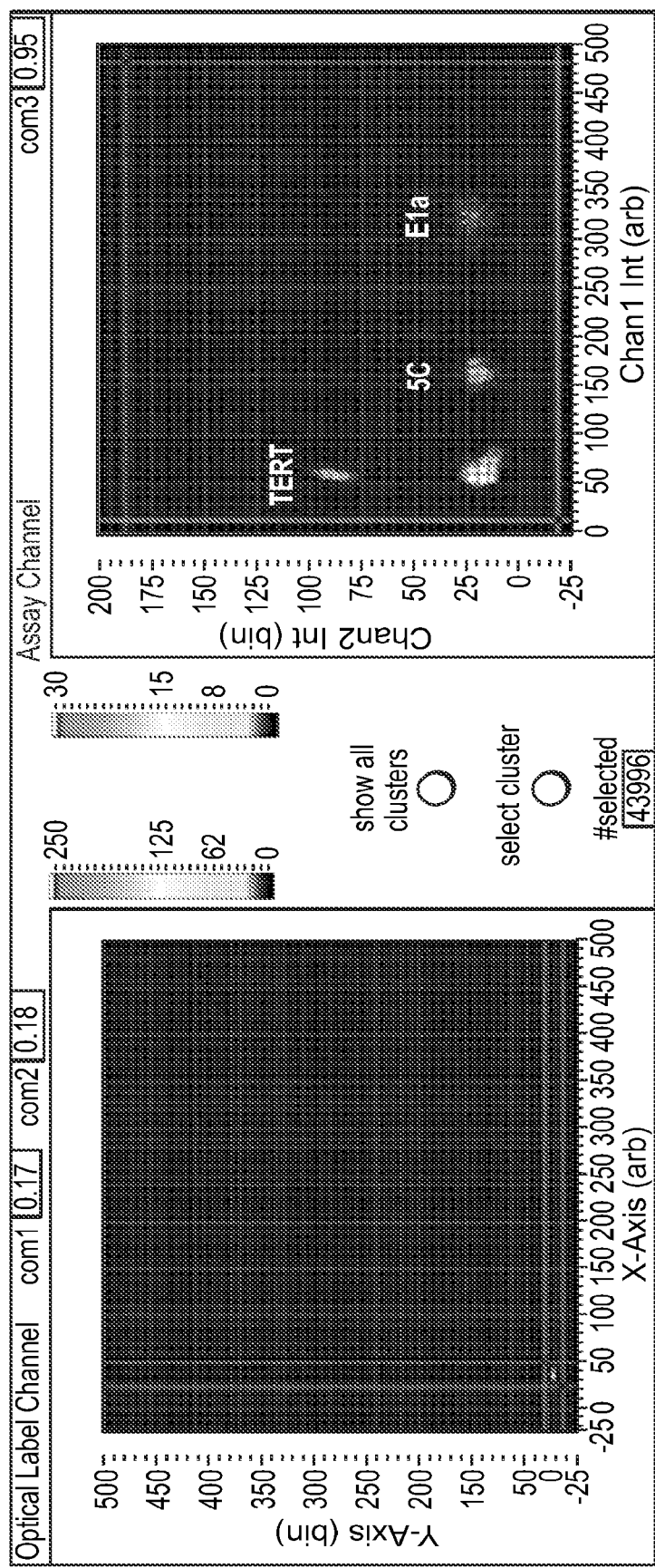
FIGS. 19A-C shows single assay selections using optical labels. Selections were taken from all of the droplets from FIG. 17. Each of the three different selections in panels A-C was for optical labels encoding the same assay (TERT, c.5C from SMN1, and BCKDHA). Histograms are as described in FIG. 17. (Left histograms, optical labels) Superimposed lines demark the bounding box for selecting a single optical label. (Right histograms, assay) Only droplets containing the selected optical label are displayed.
Figure 19B:
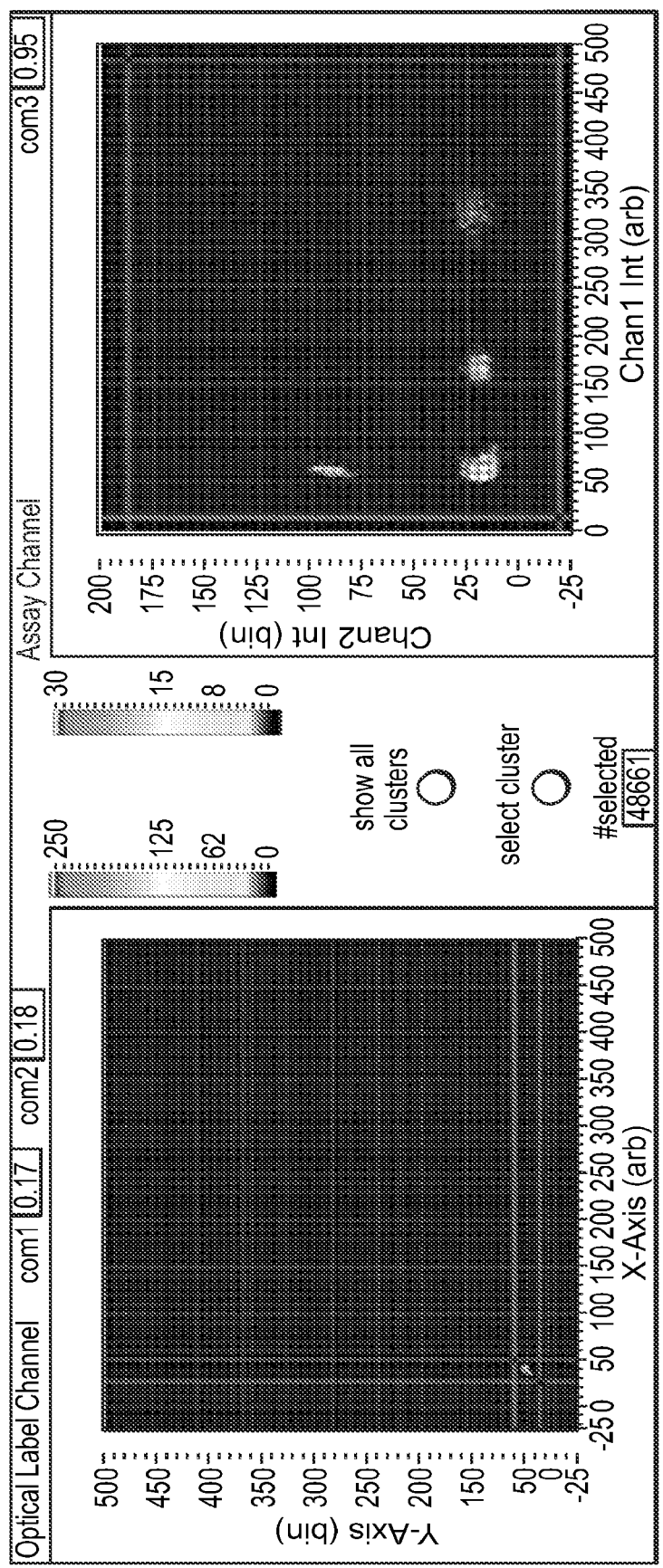
Figure 19C:
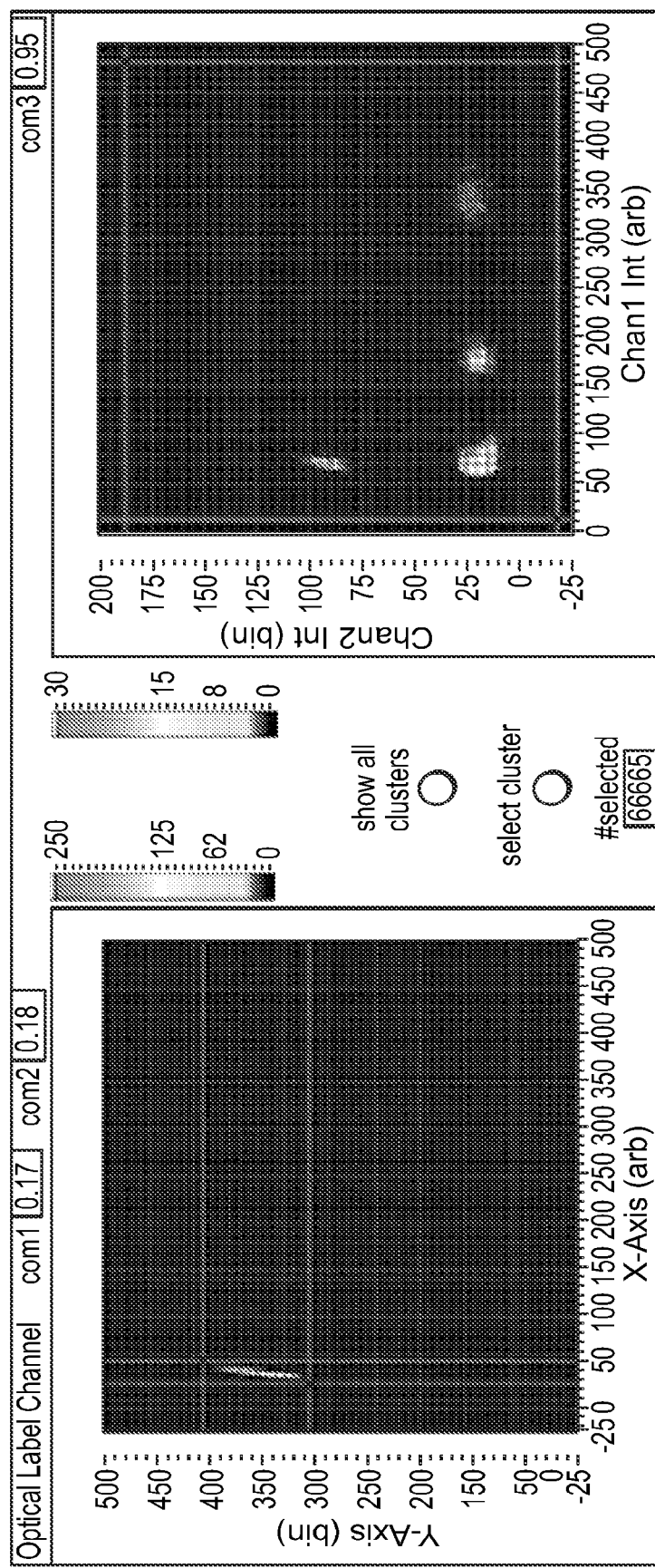
Figure 20A:
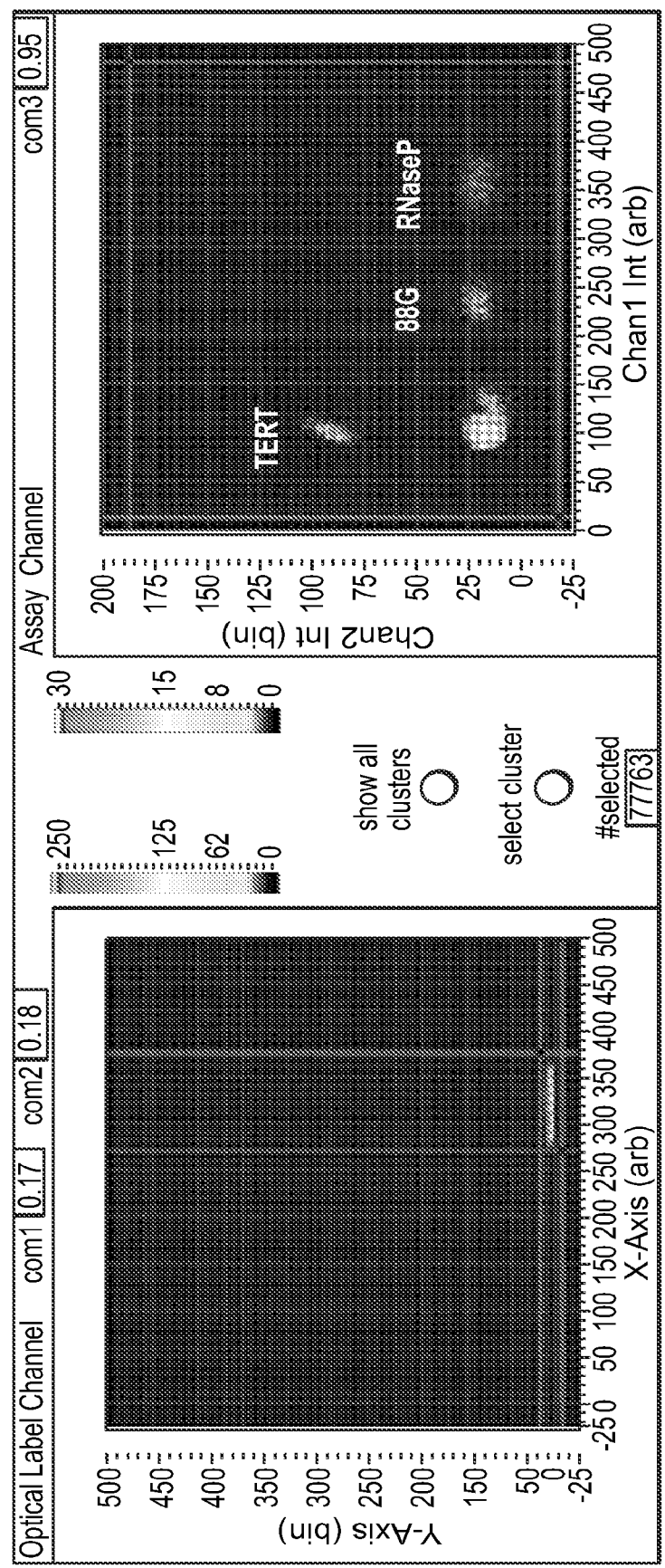
FIGS. 20A-C show single assay selections using optical labels. Selections were taken from all of the droplets from FIG. 17. Each of the three different selections in panels A-C was for optical labels encoding the same assay (TERT, c.88G from SMN1, and RNaseP). Histograms are as described in FIG. 17. (Left histograms, optical labels) Superimposed lines demark the bounding box for selecting a single optical label. (Right histograms, assay) Only droplets containing the selected optical label are displayed.
Figure 20B:
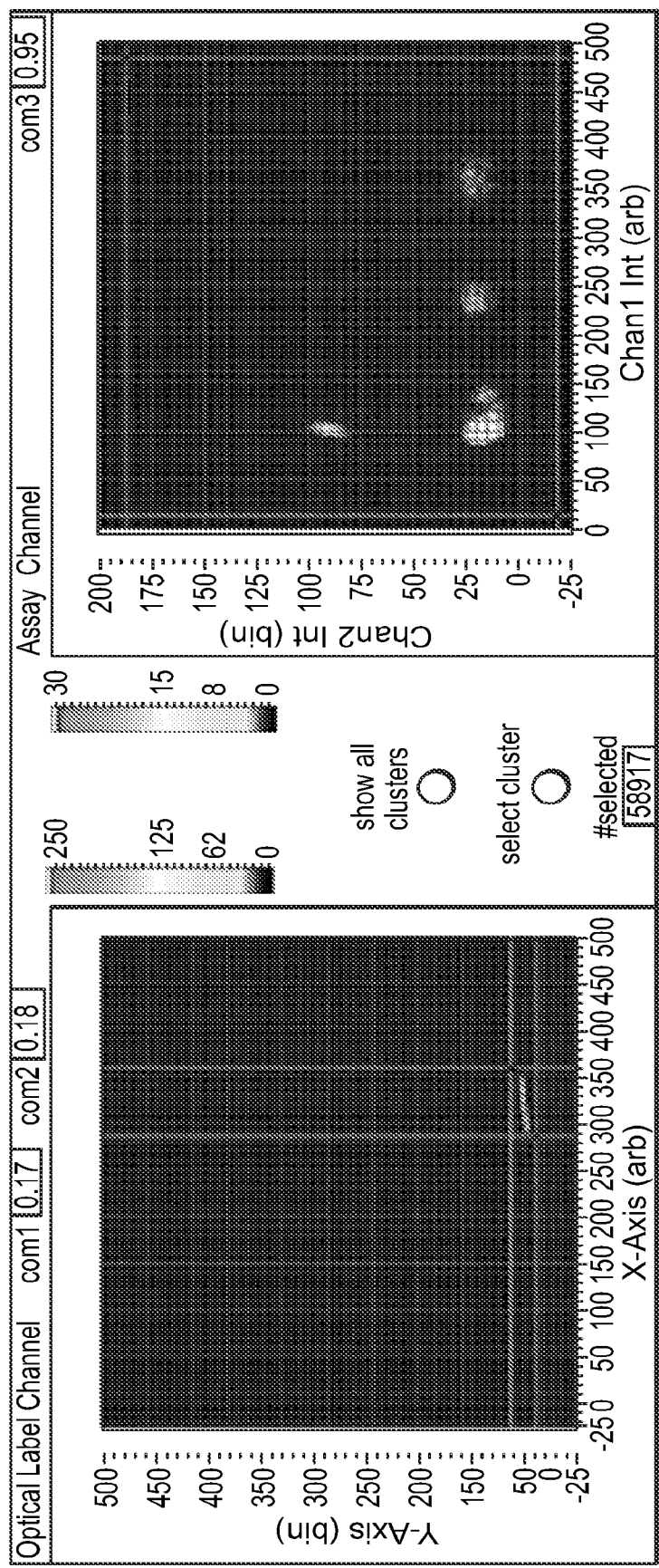
Figure 20C:
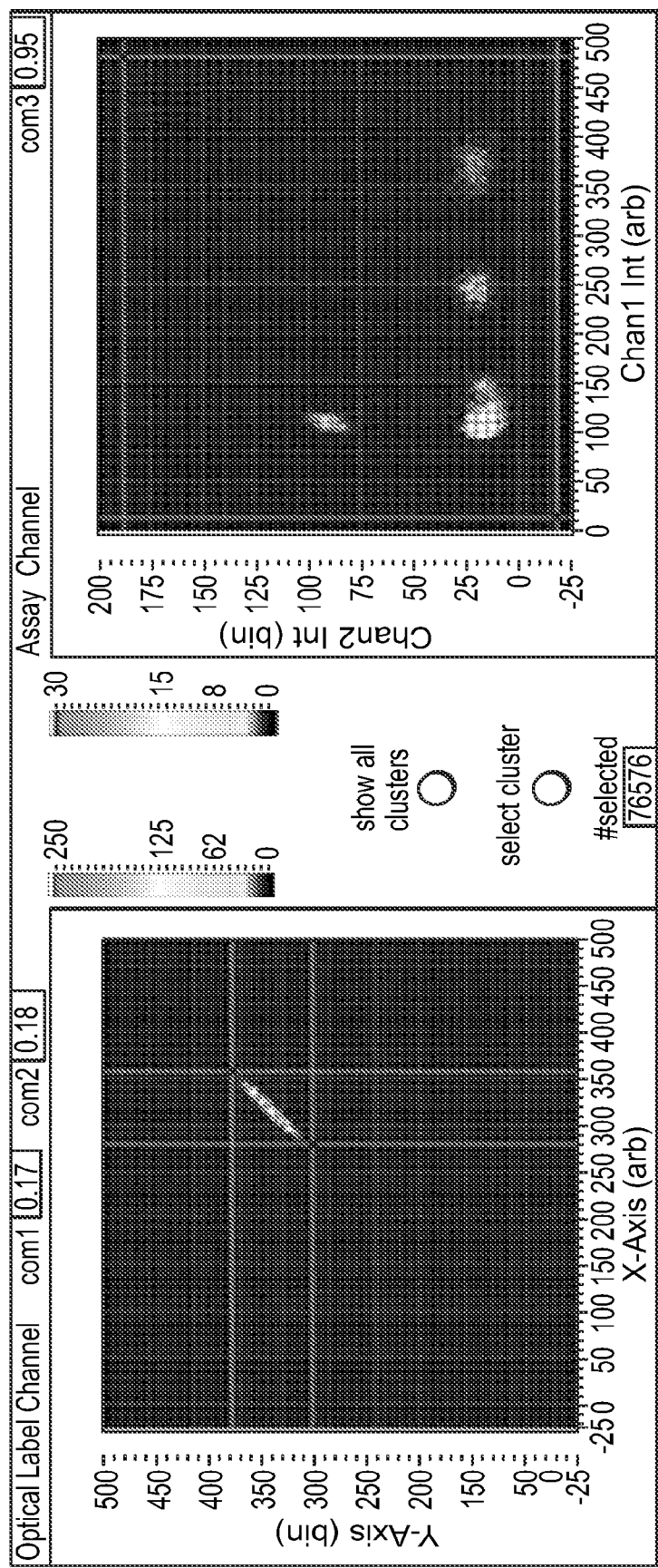
Figure 21A:
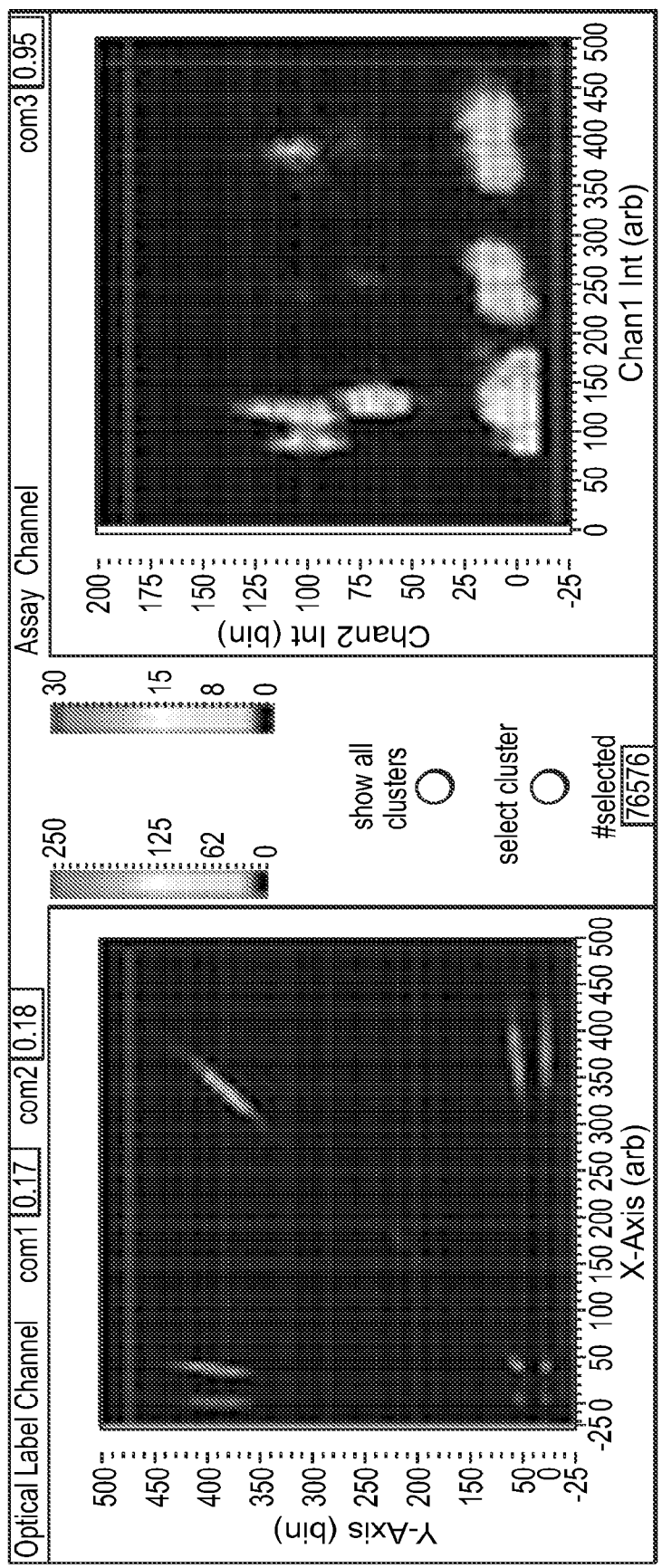
FIGS. 21A-J depict a dPCR assay combining multiplexing with optical labels using droplet merging.
Figure 21B:
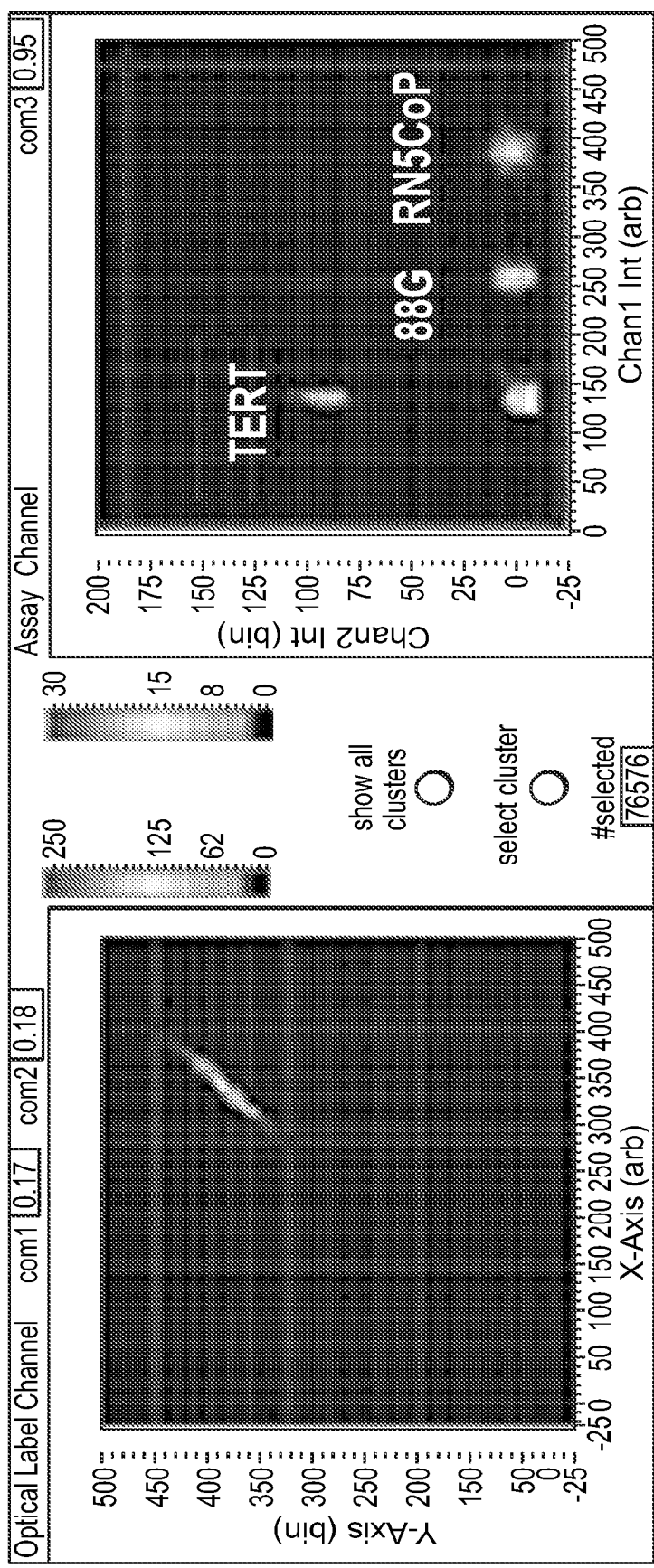
Figure 21C:
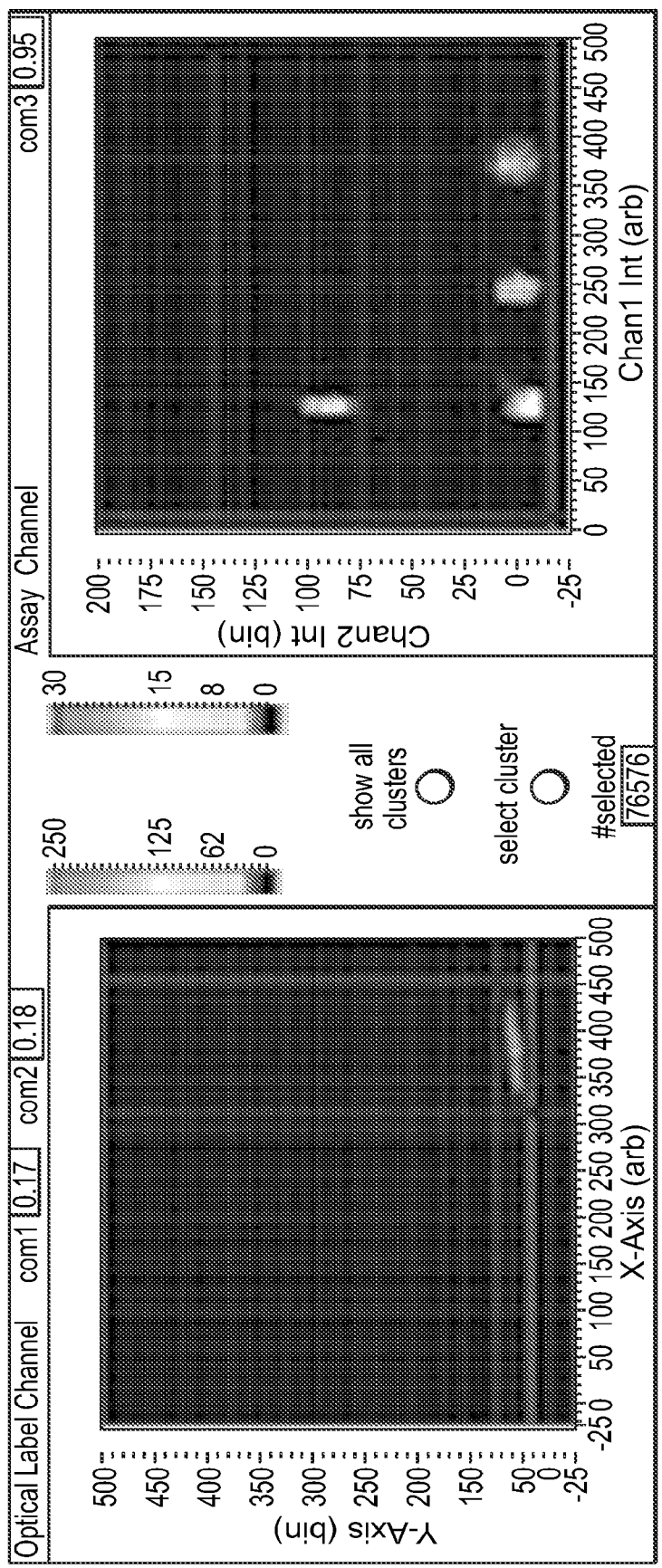
Figure 21D:
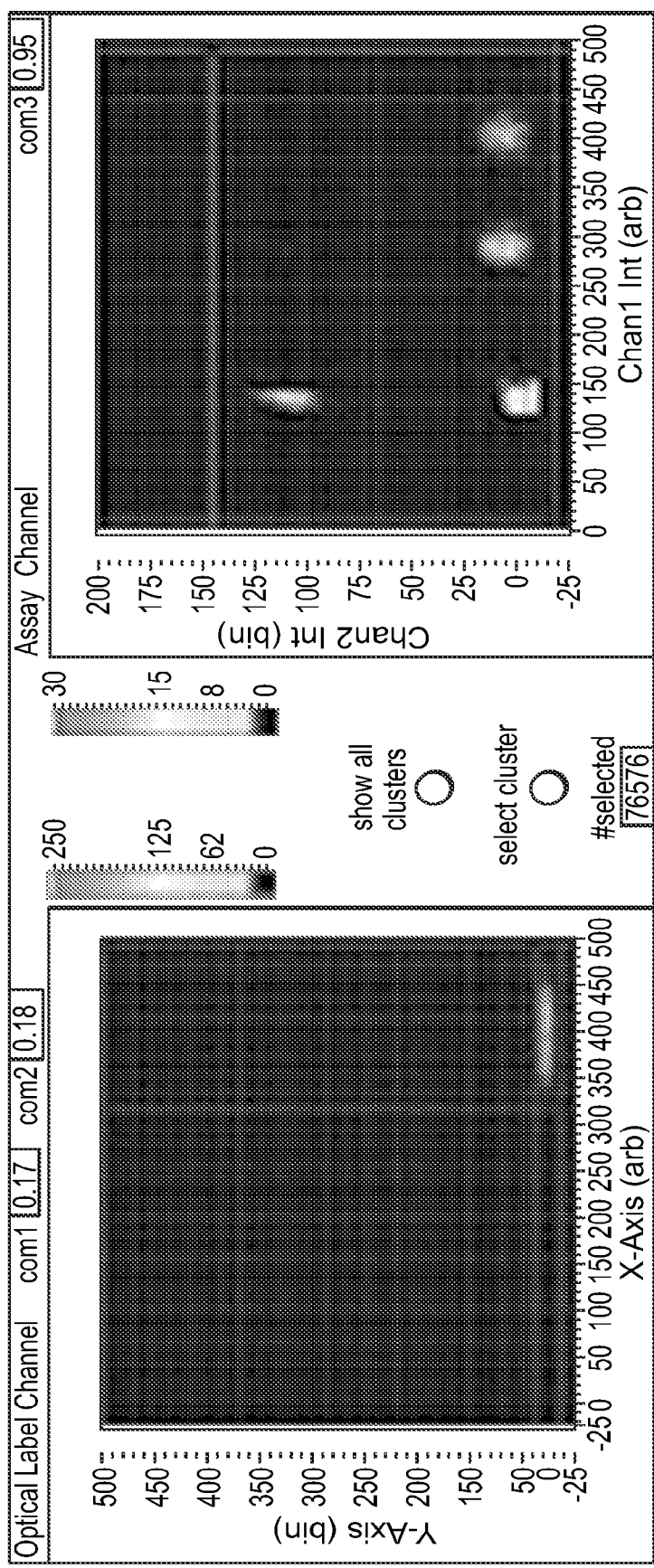
Figure 21E:
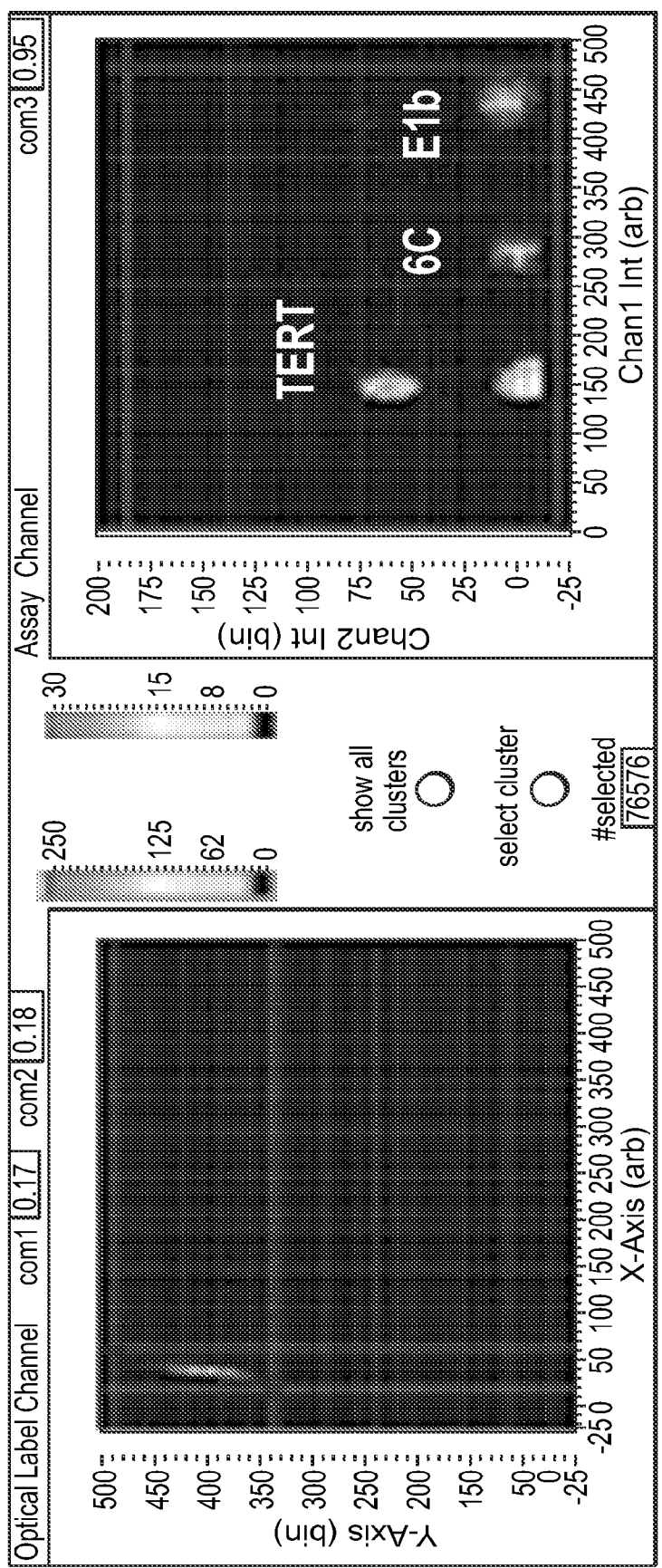
Figure 21F:
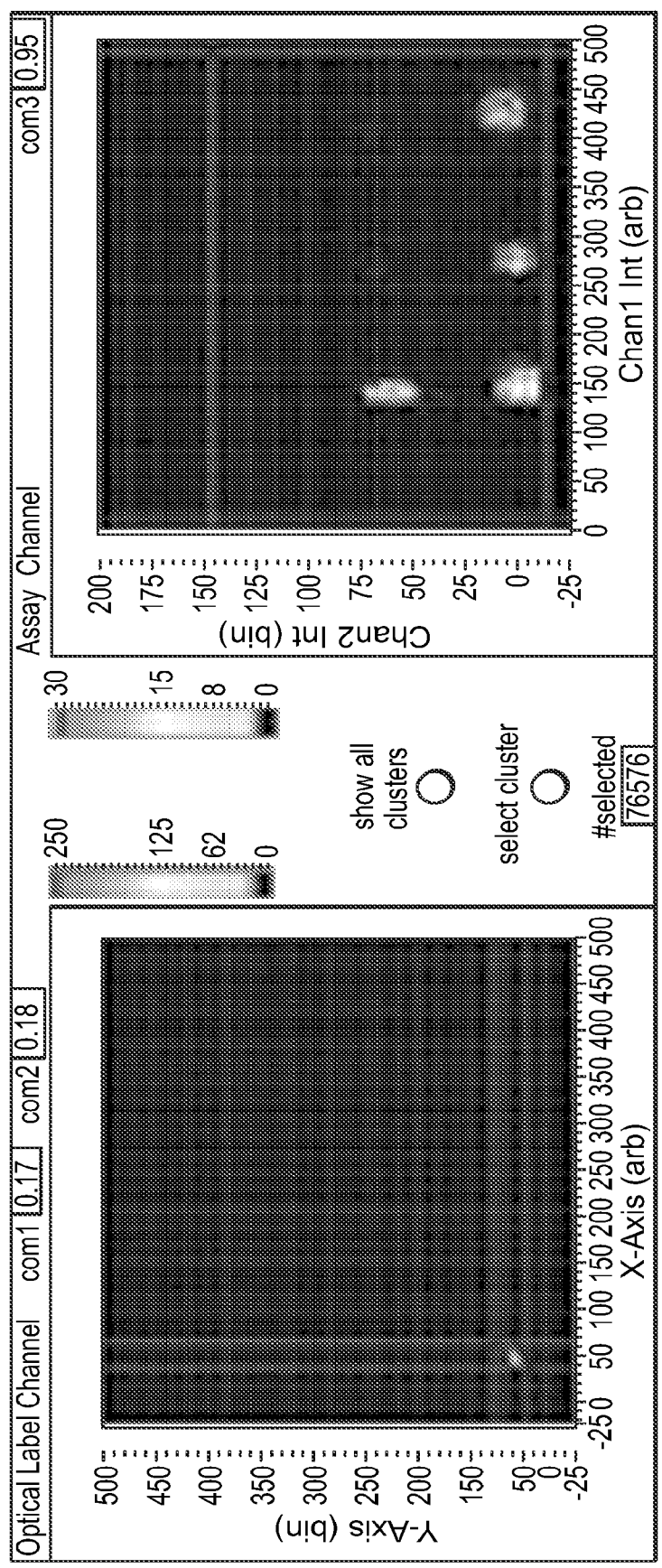
Figure 21G:
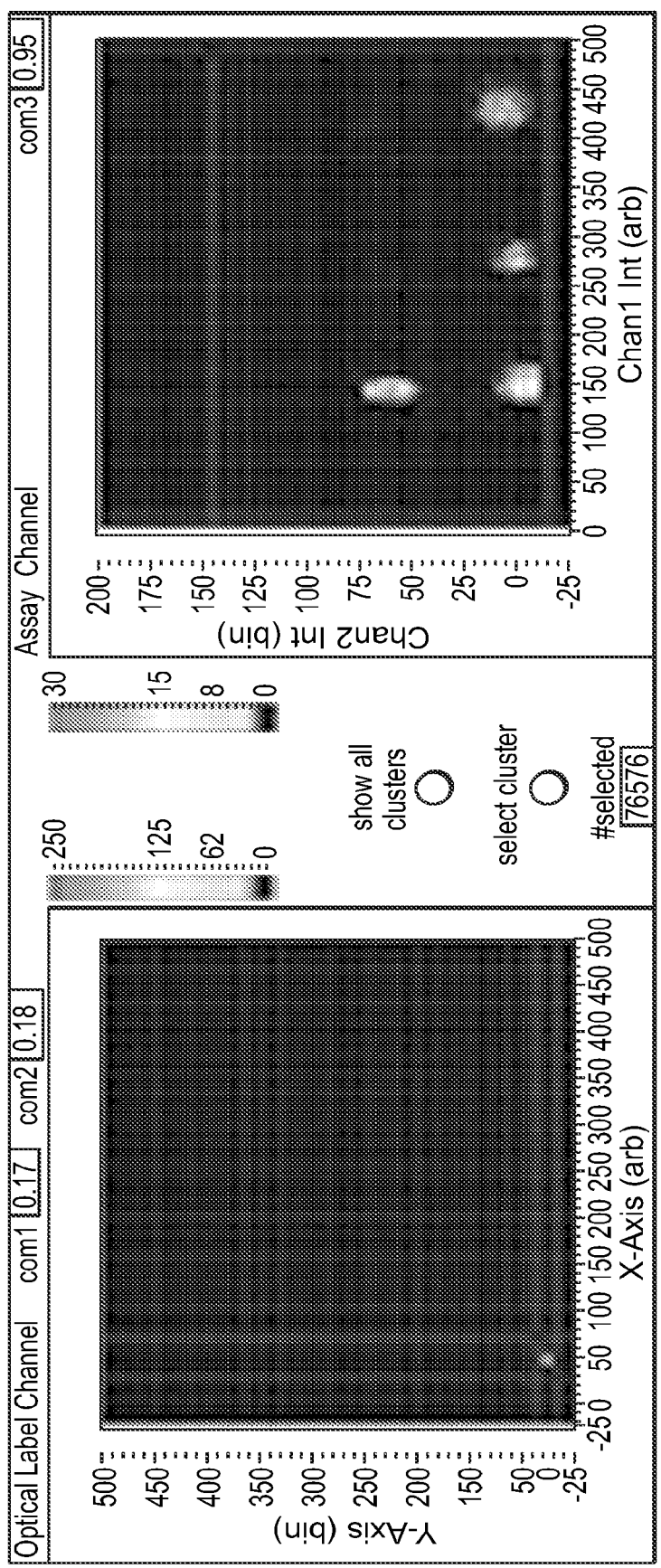
Figure 21H:
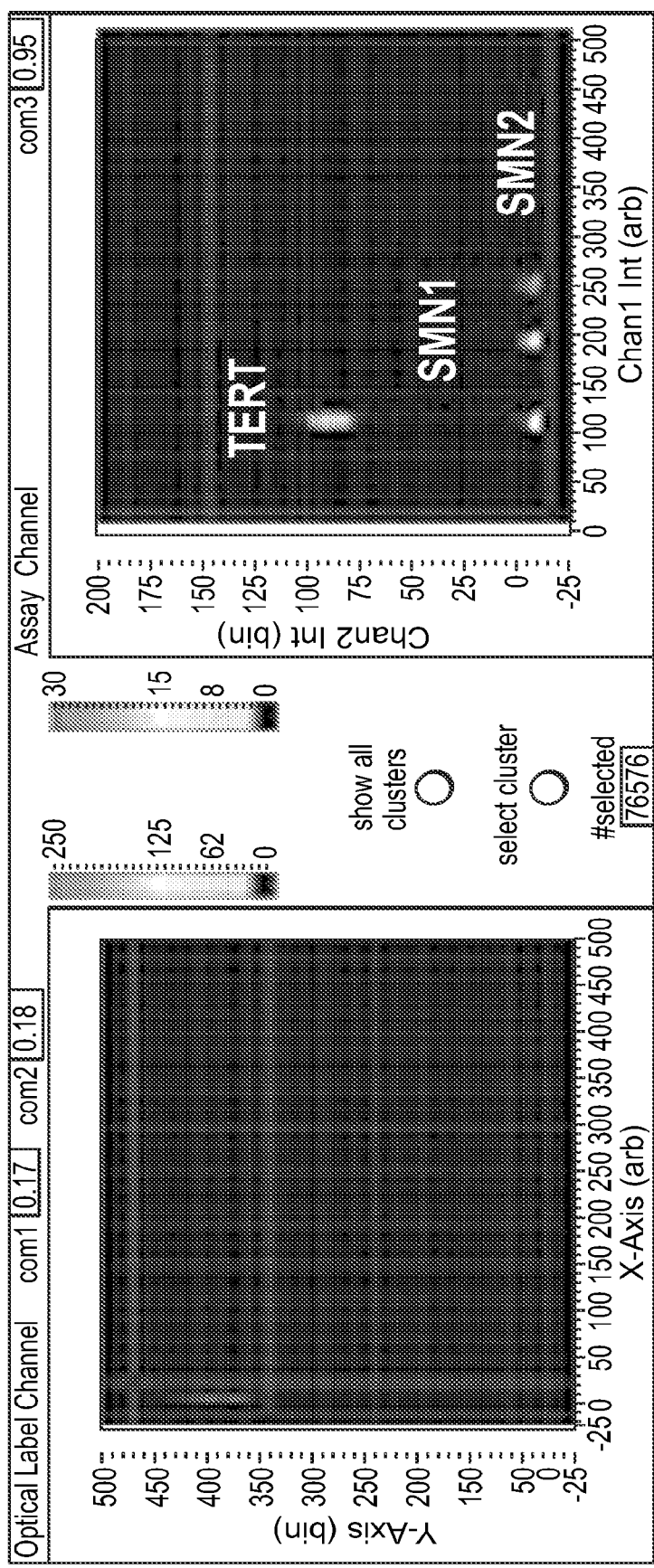
Figure 21I:
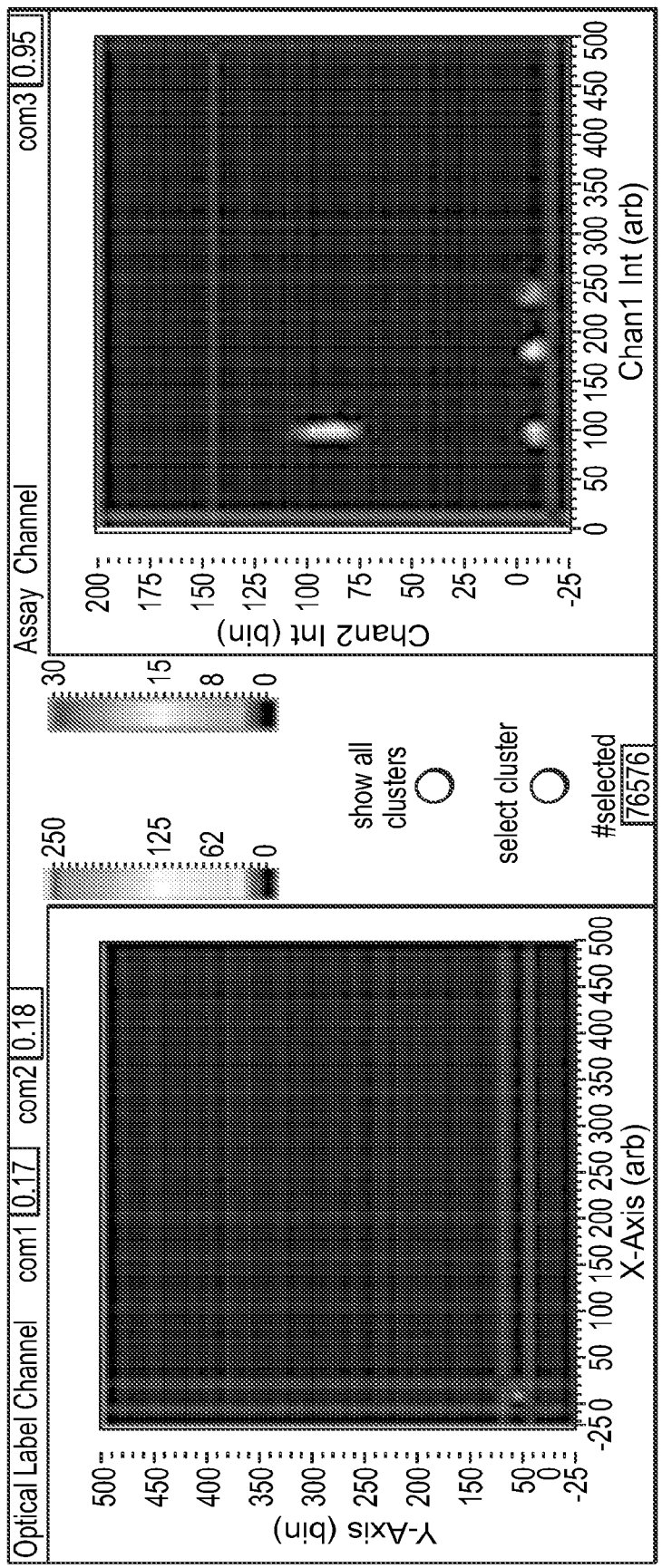
Figure 21J:
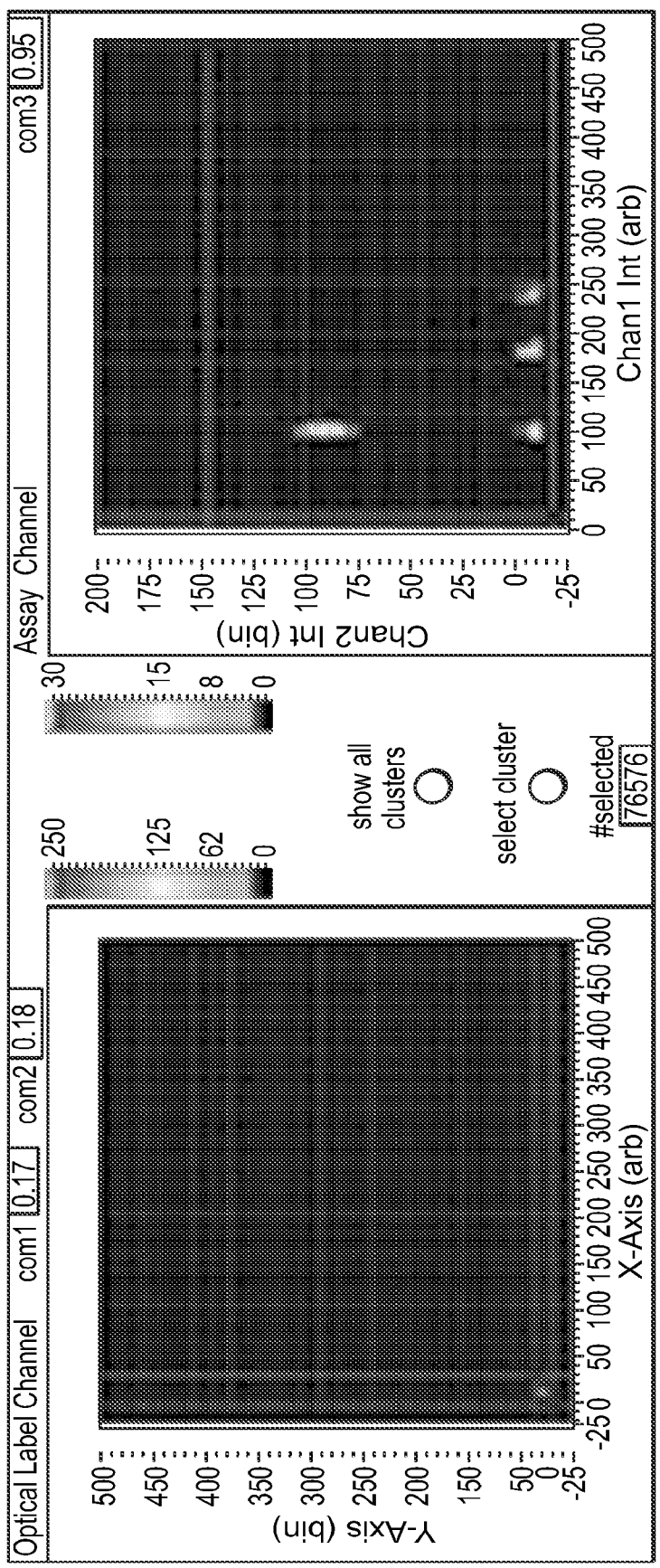

FIGS. 19A, B, and C show optical label selections for a different assay (TERT, c.5C in the SMN1 gene, and BCKDHA (labeled E1a in the figure)). In each case four distinct clusters also appeared, and by the same methods of the invention above, accurate measurements of gene copy number were made for c.5C and BCKDHA, referenced to TERT, of 2.9±0.1 and 2.0±0.2 compared to 3 and 2, respectively. FIGS. 20A, B, and C show optical label selections for a third assay (TERT, c.88G in the SMN1 gene, and RNaseP, where RNaseP is a common reference gene). Accurate gene copy numbers of 2.1±0.1 were measured for both c.88G and RNaseP, referenced to TERT, compared to the expected value of 2.

In summary, the demonstration here shows use of nine different optical labels to enable independent measurement of three triplex assays in a single experiment. Although some of the optical labels encoded for redundant assays in this example (there were only three different assays despite having nine optical labels), the invention is not constrained to any particular formatting of assays and optical labels. Embodiments of the invention include formats where all of the assays are the same across all of the optical labels; where none of the assays are the same across all of the optical labels; where some of the assays are the same across all of the optical labels; where some of the assays have greater plexity than others across all of the optical labels; where all of the assays have the same plexity across all of the optical labels; and any other arrangements of assays across all of the optical labels are considered.

Although two different fluorophores were used to create the optical labels in this example, the invention is not constrained to any particular number of fluorophores comprising the optical labels. Embodiments of the invention include optical labels comprised of 1 fluorophore, or 2 fluorophores, or 3 fluorophores, or 4 fluorophores, or up to 10 fluorophores, or up to 20 fluorophores. Optical labels can also comprise more than 20 fluorophores.

Although solely triplex assays were used in the example demonstration here, the invention is not constrained to use of triplex assays with optical labels. Embodiments of the invention include plexities of the following amounts when used with optical labels: single plex, duplex, triplex, 4-plex, up to 10-plex, up to 20-plex, up to 50-plex, and up to 100-plex. Embodiments of the invention also include plexities exceeding 100 when used with optical labels.

Another method of the invention involves the use of droplet merging, instead of co-flow, for combining multiplexing with optical labels. A demonstration using droplet merging was performed with the same 3×3×3 assay as in the preceding example with co-flow. The assays (probes and primers) combined with their unique optical labels were first encapsulated into droplets along with the PCR master mix. Subsequently, according to methods of the invention described above, a library containing a mixture of droplets from all nine optically labeled assays was merged one-to-one with droplets containing template DNA from the same patient as in the preceding example. As another method of the invention, the droplet merge was performed using a lambda-injector style merge module, as described in U.S. Provisional Application, Ser. No. 61/441,985, incorporated by reference herein. Aside from the differences between co-flow and merge, the assays and experimental procedures were identical to those above for the co-flow experiment. FIG. 21 shows 2-D histograms of droplet fluorescence intensity for the optical labels and the assays that are similar to those in FIGS. 17-20. As in the case for co-flow, upon selection of droplets containing individual optical labels, the expected distinct clusters of droplets corresponding to each assay were clearly evident. Furthermore for each assay the measured gene copy number matched or very nearly matched the expected values within experimental uncertainty (See Table 1).

TABLE 1

Gene copy number measurements from the 3 × 3 × 3 assay.

| Gene or genotype | Measured copy number | Expected copy number |
| --- | --- | --- |
| SMN1 | 1.98 ± 0.09 | 2 |
| SMN2 | 0.99 ± 0.04 | 1 |

TABLE 1-continued

Gene copy number measurements from the 3 × 3 × 3 assay.

| Gene or genotype | Measured copy number | Expected copy number |
|---|---|---|
| c.5C in SMN1 | 3.01 ± 0.06 | 3 |
| c.88G in SMN1 | 2.15 ± 0.08 | 2 |
| BCKDHA | 2.00 ± 0.05 | 2 |
| RNaseP | 2.11 ± 0.16 | 2 |

Although methods of the invention include using either microfluidics with co-flow or droplet merging, the invention is not limited in this regard. Any fluidic method capable of generating optically labeled droplets that also contain fluorogenic DNA hybridization probes are considered. For example, other embodiments well known in the art are mixing optical labels and assays in the macrofluidic environment before injection into a droplet generating chip; and mixing optical labels and assays thoroughly upstream from the droplet forming module in dedicated mixing modules, such as with a serpentine mixer.

Data Analysis

One method of the invention involves histogram-based data presentation and analysis for identifying and characterizing populations of statistically similar droplets that arise from unique probe signatures (color and intensity), and for discriminating one population of droplets from the others. Another method of the invention involves histogram-based data presentation and analysis for identifying and selecting populations of droplets based on unique signatures from optical labels. Examples of one and two-dimensional histograms have been provided for these methods, but the invention is not limited in this regard. As described above, it is anticipated that greater numbers of colors will be used for both multiplexing and for optical labels. Hence, embodiments of the invention include histograms of dimensionality greater than two, such as 3, or 4, or up to 10, or up to 20. Histograms of dimensionality greater than 20 are also incorporated into the invention.

Another method of the invention involves the selection of droplets within histograms, either for counting, or for assay selection as in the use of optical labels, or for any other purpose. Methods of the invention include selections by boundaries, either closed or unclosed, of any possible shape and dimension. Methods of the invention also include selections of droplets that exhibit fluorescence from single types of fluorophores, or from multiple types of fluorophores, such as arising from multiple probes against a common DNA target.

Polymerase Error Correction

For applications requiring very high sensitivity, such as searching for rare mutations amidst an abundance of wild-type DNA, false positive results can arise from errors from the DNA polymerase itself. For example, during one of the early thermal cycles the polymerase might synthesize the mutant strand of DNA from a wild-type template. This type of error is most likely to occur when the difference between the mutant and the wild-type is very small, such as single nucleotide polymorphism (SNP). In this method of the invention, each droplet contains only a single target nucleic acid, if any at all. In the preferred embodiment, this is accomplished under the conditions of terminal dilution. Droplets that contain amplification products that are a wild-type of the target are detected based on emission from the fluorophore that is released from the probe that hybridizes to the wild-type of the target. Droplets that contain the variant of the target are detected based on emission from the fluorophore that is released from the probe that hybridizes to the variant of the target. Since each droplet starts with only a single nucleic acid molecule, the resultant amplification products in each droplet are either homogeneous for the target or homogenous for the variant of the target.

However, certain droplets will contain a heterogeneous mixture of both target and target variant due to polymerase errors during the PCR reaction. Error rates in PCR vary according to the precise nucleic acid sequence, the thermostable enzyme used, and the in vitro conditions of DNA synthesis. For example, the error frequency (mutations per nucleotide per cycle) during PCR catalyzed by the thermostable *Thermus aquaticus* (Taq) DNA polymerase vary more than 10-fold, from $\sim 2 \times 10'$ to $<1 \times 10^{-5}$. Eckert et al. (Genome Res. 1:17-24, 1991), the content of which is incorporated by reference herein in its entirety. Polymerase-mediated errors at a frequency of 1 mutation per 10,000 nucleotides per cycle are an important consideration for any PCR application that begins with a small amount of starting material (e.g., less than a total of nucleotides of target DNA) or that focuses on individual DNA molecules in the final PCR population.

The proportion of DNA molecules that contain sequence changes is a function of the error rate per nucleotide per cycle, the number of amplification cycles and the starting population size. The population of altered DNA molecules arises during PCR from two sources: (1) new errors at each PCR cycle; and (2) amplification of DNA molecules containing errors from previous cycles. The formula $f=np/2$ describes the average mutation frequency (f) for PCR amplification as a function of the polymerase error rate per nucleotide per cycle (p) and the number of cycles (n), assuming that p is constant at each cycle. Due to the exponential nature of PCR, the occurrence of an early error can increase the final error frequency above the average described by $f=np/2$, because the variant DNA molecule will be amplified with each cycle, resulting in populations with a larger than average number of variants.

A polymerase error that converts a wild-type of the target to a variant of the target during an early round of amplification results in a heterogeneous population of target and target variant in a droplet, and may lead to a droplet being incorrectly identified as containing a variant of the target, i.e., a false positive. Such false positives greatly impact the validity and precision of digital PCR results.

Methods of the invention are able to detect which droplets contain a heterogeneous population of molecules and are able to exclude those droplets from analysis. As droplets containing amplified product flow in a channel through the detector module, the module is able to detect the fluorescent emission in each droplet. Droplets that produce only a single signal are classified as droplets that contain a homogeneous population of target. Since probes that hybridize to the wild-type of the target have a different fluorophore attached than probes that hybridize to a variant of the wild-type of the target, methods of the invention can classify each droplet as containing either a homogeneous population of amplicons of the target or a homogeneous population of amplicons of the variant of the target.

Droplets that produce two signals are classified as droplets that contain a heterogeneous population of molecules. Since each droplet started with at most a single target nucleic acid, a droplet that includes amplification products that are both amplicons of the target and amplicons of a variant of the target are droplets in which the variant of the target was produced by a polymerase error during the PCR reaction, most likely a polymerase error during an early cycle of the PCR reaction. Such droplets are detected and excluded from analysis.

Analysis

Analyze is then performed on only the droplets that contain a homogeneous population of molecules. The analysis may be based on counting, i.e., determining a number of droplets that contain only wild-type target, and determining a number of droplets that contain only a variant of the target. Such methods are well known in the art. See, e.g., Lapidus et al. (U.S. Pat. Nos. 5,670,325 and 5,928,870) and Shuber et al. (U.S. Pat. Nos. 6,203,993 and 6,214,558), the content of each of which is incorporated by reference herein in its entirety.

Generally, the presence of droplets containing only variant is indicative of a disease, such as cancer. In certain embodiments, the variant is an allelic variant, such as an insertion, deletion, substitution, translocation, or single nucleotide polymorphism (SNP).

Biomarkers that are associated with cancer are known in the art. Biomarkers associated with development of breast cancer are shown in Erlander et al. (U.S. Pat. No. 7,504,214), Dai et al. (U.S. Pat. Nos. 7,514,209 and 7,171,311), Baker et al. (U.S. Pat. Nos. 7,056,674 and 7,081,340), Erlander et al. (US 2009/0092973). The contents of the patent application and each of these patents are incorporated by reference herein in their entirety. Biomarkers associated with development of cervical cancer are shown in Patel (U.S. Pat. No. 7,300,765), Pardee et al. (U.S. Pat. No. 7,153,700), Kim (U.S. Pat. No. 6,905,844), Roberts et al. (U.S. Pat. No. 6,316,208), Schlegel (US 2008/0113340), Kwok et al. (US 2008/0044828), Fisher et al. (US 2005/0260566), Sastry et al. (US 2005/0048467), Lai (US 2008/0311570) and Van Der Zee et al. (US 2009/0023137). Biomarkers associated with development of vaginal cancer are shown in Giordano (U.S. Pat. No. 5,840,506), Kruk (US 2008/0009005), Hellman et al. (Br J Cancer. 100(8):1303-1314, 2009). Biomarkers associated with development of brain cancers (e.g., glioma, cerebellum, medulloblastoma, astrocytoma, ependymoma, glioblastoma) are shown in D'Andrea (US 2009/0081237), Murphy et al. (US 2006/0269558), Gibson et al. (US 2006/0281089), and Zetter et al. (US 2006/0160762). Biomarkers associated with development of renal cancer are shown in Patel (U.S. Pat. No. 7,300,765), Soyupak et al. (U.S. Pat. No. 7,482,129), Sahin et al. (U.S. Pat. No. 7,527,933), Price et al. (U.S. Pat. No. 7,229,770), Raitano (U.S. Pat. No. 7,507,541), and Becker et al. (US 2007/0292869). Biomarkers associated with development of hepatic cancers (e.g., hepatocellular carcinoma) are shown in Home et al. (U.S. Pat. No. 6,974,667), Yuan et al. (U.S. Pat. No. 6,897,018), Hanausek-Walaszek et al. (U.S. Pat. No. 5,310,653), and Liew et al. (US 2005/0152908). Biomarkers associated with development of gastric, gastrointestinal, and/or esophageal cancers are shown in Chang et al. (U.S. Pat. No. 7,507,532), Bae et al. (U.S. Pat. No. 7,368,255), Muramatsu et al. (U.S. Pat. No. 7,090,983), Sahin et al. (U.S. Pat. No. 7,527,933), Chow et al. (US 2008/0138806), Waldman et al. (US 2005/0100895), Goldenring (US 2008/0057514), An et al. (US 2007/0259368), Guilford et al. (US 2007/0184439), Wirtz et al. (US 2004/0018525), Filella et al. (Acta Oncol. 33(7):747-751, 1994), Waldman et al. (U.S. Pat. No. 6,767,704), and Lipkin et al. (Cancer Research, 48:235-245, 1988). Biomarkers associated with development of ovarian cancer are shown in Podust et al. (U.S. Pat. No. 7,510,842), Wang (U.S. Pat. No. 7,348,142), O'Brien et al. (U.S. Pat. Nos. 7,291,462, 6,942,978, 6,316,213, 6,294,344, and 6,268,165), Ganetta (U.S. Pat. No. 7,078,180), Malinowski et al. (US 2009/0087849), Beyer et al. (US 2009/0081685), Fischer et al. (US 2009/0075307), Mansfield et al. (US 2009/0004687), Livingston et al. (US 2008/0286199), Farias-Eisner et al. (US 2008/0038754), Ahmed et al. (US 2007/0053896), Giordano (US and Tchagang et al. (Mol Cancer Ther, 7:27-37, 2008). Biomarkers associated with development of head-and-neck and thyroid cancers are shown in Sidransky et al. (U.S. Pat. No. 7,378,233), Skolnick et al. (U.S. Pat. No. 5,989,815), Budiman et al. (US 2009/0075265), Hasina et al. (Cancer Research, 63:555-559, 2003), Kebebew et al. (US 2008/0280302), and Ralhan (Mol Cell Proteomics, 7(6):1162-1173, 2008). The contents of each of the articles, patents, and patent applications are incorporated by reference herein in their entirety. Biomarkers associated with development of colorectal cancers are shown in Raitano et al. (U.S. Pat. No. 7,507,541), Reinhard et al. (U.S. Pat. No. 7,501,244), Waldman et al. (U.S. Pat. No. 7,479,376); Schleyer et al. (U.S. Pat. No. 7,198,899); Reed (U.S. Pat. No. 7,163,801), Robbins et al. (U.S. Pat. No. 7,022,472), Mack et al. (U.S. Pat. No. 6,682,890), Tabiti et al. (U.S. Pat. No. 5,888,746) Budiman et al. (US 2009/0098542), Karl (US 2009/0075311), Arjol et al. (US 2008/0286801), Lee et al. (US 2008/0206756), Mori et al. (US 2008/0081333), Wang et al. (US 2008/0058432), Belacel et al. (US 2008/0050723), Stedronsky et al. (US 2008/0020940), An et al. (US 2006/0234254), Eveleigh et al. (US 2004/0146921), and Yeatman et al. (US 2006/0195269). Biomarkers associated with development of prostate cancer are shown in Sidransky (U.S. Pat. No. 7,524,633), Platica (U.S. Pat. No. 7,510,707), Salceda et al. (U.S. Pat. Nos. 7,432,064 and 7,364,862), Siegler et al. (U.S. Pat. No. 7,361,474), Wang (U.S. Pat. No. 7,348,142), Ali et al. (U.S. Pat. No. 7,326,529), Price et al. (U.S. Pat. No. 7,229,770), O'Brien et al. (U.S. Pat. No. 7,291,462), Golub et al. (U.S. Pat. No. 6,949,342), Ogden et al. (U.S. Pat. No. 6,841,350), An et al. (U.S. Pat. No. 6,171,796), Bergan et al. (US 2009/0124569), Bhowmick (US 2009/0017463), Srivastava et al. (US 2008/0269157), Chinnaiyan et al. (US 2008/0222741), Thaxton et al. (US 2008/0181850), Dahary et al. (US 2008/0014590), Diamandis et al. (US 2006/0269971), Rubin et al. (US 2006/0234259), Einstein et al. (US 2006/0115821), Paris et al. (US 2006/0110759), Condon-Cardo (US 2004/0053247), and Ritchie et al. (US 2009/0127454). Biomarkers associated with development of pancreatic cancer are shown in Sahin et al. (U.S. Pat. No. 7,527,933), Rataino et al. (U.S. Pat. No. 7,507,541), Schleyer et al. (U.S. Pat. No. 7,476,506), Domon et al. (U.S. Pat. No. 7,473,531), McCaffey et al. (U.S. Pat. No. 7,358,231), Price et al. (U.S. Pat. No. 7,229,770), Chan et al. (US 2005/0095611), Mitchl et al. (US 2006/0258841), and Faca et al. (PLoS Med 5(6):e123, 2008). Biomarkers associated with development of lung cancer are shown in Sahin et al. (U.S. Pat. No. 7,527,933), Hutteman (U.S. Pat. No. 7,473,530), Bae et al. (U.S. Pat. No. 7,368,255), Wang (U.S. Pat. No. 7,348,142), Nacht et al. (U.S. Pat. No. 7,332,590), Gure et al. (U.S. Pat. No. 7,314,721), Patel (U.S. Pat. No. 7,300,765), Price et al. (U.S. Pat. No. 7,229,770), O'Brien et al. (U.S. Pat. Nos. 7,291,462 and 6,316,213), Muramatsu et al. (U.S. Pat. No. 7,090,983), Carson et al. (U.S. Pat. No. 6,576,420), Giordano (U.S. Pat. No. 5,840,506), Guo (US 2009/0062144), Tsao et al. (US 2008/0176236), Nakamura et al. (US 2008/0050378), Raponi et al. (US 2006/0252057), Yip et al. (US 2006/0223127), Pollock et al. (US 2006/0046257), Moon et al. (US 2003/0224509), and Budiman et al. (US 2009/0098543). Biomarkers associated with development of skin cancer (e.g., basal cell carcinoma, squamous cell carcinoma, and melanoma) are shown in Roberts et al. (U.S. Pat. No. 6,316,208), Polsky (U.S. Pat. No. 7,442,507), Price et al. (U.S. Pat. No. 7,229,770), Genetta (U.S. Pat. No. 7,078,180), Carson et al. (U.S. Pat. No. 6,576,420), Moses et al. (US 2008/0286811), Moses et al. (US 2008/0268473), Dooley et al. (US 2003/0232356), Chang et al. (US 2008/0274908), Alani et al. (US 2008/0118462), Wang (US 2007/0154889), and Zetter et al. (US 2008/0064047). Biomarkers associated with development of multiple myeloma are shown in Coignet (U.S. Pat. No. 7,449,303), Shaughnessy et al. (U.S. Pat. No. 7,308,364), Seshi (U.S. Pat. No. 7,049,072), and Shaughnessy et al. (US 2008/0293578, US 2008/0234139, and US 2008/0234138). Biomarkers associated with development of leukemia are shown in Ando et al. (U.S. Pat. No. 7,479,371), Coignet (U.S. Pat. Nos. 7,479,370 and 7,449,303), Davi et al. (U.S. Pat. No. 7,416,851), Chiorazzi (U.S. Pat. No. 7,316,906), Seshi (U.S. Pat. No. 7,049,072), Van Baren et al. (U.S. Pat. No. 6,130,052), Taniguchi (U.S. Pat. No. 5,643,729), Insel et al. (US 2009/0131353), and Van Bockstaele et al. (Blood Rev. 23(1):25-47, 2009). Biomarkers associated with development of lymphoma are shown in Ando et al. (U.S. Pat. No. 7,479,371), Levy et al. (U.S. Pat. No. 7,332,280), and Arnold (U.S. Pat. No. 5,858,655). Biomarkers associated with development of bladder cancer are shown in Price et al. (U.S. Pat. No. 7,229,770), Orntoft (U.S. Pat. No. 6,936,417), Haak-Frendscho et al. (U.S. Pat. No. 6,008,003), Feinstein et al. (U.S. Pat. No. 6,998,232), Elting et al. (US 2008/0311604), and Wewer et al. (2009/0029372). The content of each of the above references is incorporated by reference herein in its entirety.

In certain embodiments, methods of the invention may be used to monitor a patient for recurrence of a cancer. Since the patient has already been treated for the cancer, the genetic profile and particular mutation(s) associated with that patient's cancer are already known. Probes may be designed that specifically hybridize to the region of the nucleic acid that contains the mutation(s) that is indicative of the cancer for which the patient was previously treated. A patient's sample (e.g., pus, sputum, semen, urine, blood, saliva, stool, or cerebrospinal fluid) may then be analyzed as described above to determine whether the mutant allele(s) is detected in the sample, the presence of which being indicative of recurrence of the cancer.

Droplet Sorting

Methods of the invention may further include sorting the droplets based upon whether the droplets contain a homogeneous population of molecules or a heterogeneous population of molecules. A sorting module may be a junction of a channel where the flow of droplets can change direction to enter one or more other channels, e.g., a branch channel, depending on a signal received in connection with a droplet interrogation in the detection module. Typically, a sorting module is monitored and/or under the control of the detection module, and therefore a sorting module may correspond to the detection module. The sorting region is in communication with and is influenced by one or more sorting apparatuses.

A sorting apparatus includes techniques or control systems, e.g., dielectric, electric, electro-osmotic, (micro-) valve, etc. A control system can employ a variety of sorting techniques to change or direct the flow of molecules, cells, small molecules or particles into a predetermined branch channel. A branch channel is a channel that is in communication with a sorting region and a main channel. The main channel can communicate with two or more branch channels at the sorting module or branch point, forming, for example, a T-shape or a Y-shape. Other shapes and channel geometries may be used as desired. Typically, a branch channel receives droplets of interest as detected by the detection module and sorted at the sorting module. A branch channel can have an outlet module and/or terminate with a well or reservoir to allow collection or disposal (collection module or waste module, respectively) of the molecules, cells, small molecules or particles. Alternatively, a branch channel may be in communication with other channels to permit additional sorting.

A characteristic of a fluidic droplet may be sensed and/or determined in some fashion, for example, as described herein (e.g., fluorescence of the fluidic droplet may be determined), and, in response, an electric field may be applied or removed from the fluidic droplet to direct the fluidic droplet to a particular region (e.g. a channel). In certain embodiments, a fluidic droplet is sorted or steered by inducing a dipole in the uncharged fluidic droplet (which may be initially charged or uncharged), and sorting or steering the droplet using an applied electric field. The electric field may be an AC field, a DC field, etc. For example, a channel containing fluidic droplets and carrier fluid, divides into first and second channels at a branch point. Generally, the fluidic droplet is uncharged. After the branch point, a first electrode is positioned near the first channel, and a second electrode is positioned near the second channel. A third electrode is positioned near the branch point of the first and second channels. A dipole is then induced in the fluidic droplet using a combination of the electrodes. The combination of electrodes used determines which channel will receive the flowing droplet. Thus, by applying the proper electric field, the droplets can be directed to either the first or second channel as desired. Further description of droplet sorting is shown for example in Link et al. (U.S. patent application numbers 2008/0014589, 2008/0003142, and 2010/0137163) and European publication number EP2047910 to Raindance Technologies Inc.

Based upon the detected signal at the detection module, droplets containing a heterogeneous population of molecules are sorted away from droplets that contain a homogeneous population of molecules. Droplets may be further sorted to separate droplets that contain a homogeneous population of amplicons of the target from droplets that contain a homogeneous population of amplicons of the variant of the target.

Release of Target from Droplet

Methods of the invention may further involve releasing amplified target molecules from the droplets for further analysis. Methods of releasing amplified target molecules from the droplets are shown in for example in Link et al. (U.S. patent application numbers 2008/0014589, 2008/0003142, and 2010/0137163) and European publication number EP2047910 to RainDance Technologies Inc.

In certain embodiments, sample droplets are allowed to cream to the top of the carrier fluid. By way of non-limiting example, the carrier fluid can include a perfluorocarbon oil that can have one or more stabilizing surfactants. The droplet rises to the top or separates from the carrier fluid by virtue of the density of the carrier fluid being greater than that of the aqueous phase that makes up the droplet. For example, the perfluorocarbon oil used in one embodiment of the methods of the invention is 1.8, compared to the density of the aqueous phase of the droplet, which is 1.0.

The creamed liquids are then placed onto a second carrier fluid which contains a de-stabilizing surfactant, such as a perfluorinated alcohol (e.g. 1H,1H,2H,2H-Perfluoro-1-octanol). The second carrier fluid can also be a perfluorocarbon oil. Upon mixing, the aqueous droplets begins to coalesce, and coalescence is completed by brief centrifugation at low speed (e.g., 1 minute at 2000 rpm in a microcentrifuge). The coalesced aqueous phase can now be removed and the further analyzed.

The released amplified material can also be subjected to further amplification by the use tailed primers and secondary PCR primers. In this embodiment the primers in the droplet contain an additional sequence or tail added onto the 5' end of the sequence specific portion of the primer. The sequences for the tailed regions are the same for each primer pair and are incorporated onto the 5' portion of the amplicons during PCR cycling. Once the amplicons are removed from the droplets, another set of PCR primers that can hybridize to the tail regions of the amplicons can be used to amplify the products through additional rounds of PCR. The secondary primers can exactly match the tailed region in length and sequence or can themselves contain additional sequence at the 5' ends of the tail portion of the primer. During the secondary PCR cycling these additional regions also become incorporated into the amplicons. These additional sequences can include, but are not limited to adaptor regions utilized by sequencing platforms for library preparation and sequencing, sequences used as a barcoding function for the identification of samples multiplexed into the same reaction. molecules for the separation of amplicons from the rest of the reaction materials such as biotin, digoxin, peptides, or antibodies and molecules such as fluorescent markers that can be used to identify the fragments.

In certain embodiments, the amplified target molecules are sequenced. In a particular embodiment, the sequencing is single-molecule sequencing-by-synthesis. Single-molecule sequencing is shown for example in Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Briefly, a single-stranded nucleic acid (e.g., DNA or cDNA) is hybridized to oligonucleotides attached to a surface of a flow cell. The single-stranded nucleic acids may be captured by methods known in the art, such as those shown in Lapidus (U.S. Pat. No. 7,666,593). The oligonucleotides may be covalently attached to the surface or various attachments other than covalent linking as known to those of ordinary skill in the art may be employed. Moreover, the attachment may be indirect, e.g., via the polymerases of the invention directly or indirectly attached to the surface. The surface may be planar or otherwise, and/or may be porous or non-porous, or any other type of surface known to those of ordinary skill to be suitable for attachment. The nucleic acid is then sequenced by imaging the polymerase-mediated addition of fluorescently-labeled nucleotides incorporated into the growing strand surface oligonucleotide, at single molecule resolution.

Experimental Detail

What follows is experimental detail for the various experiments details above.

Primers and Probes

All TaqMan® primers and probes used here are listed in Table 2. Unless otherwise noted by reference in the table, the primers and probes were designed with the "Custom TaqMan® Assay Design Tool" from Applied Biosystems Inc. (ABI) and procured through ABI (Carlsbad, CA). Probes were labeled with 6-carboxyfluorescein (FAM, $\lambda_{ex}$ 494 nm \ $\lambda_{em}$ 494 nm) or VIC™ (from ABI, $\lambda_{ex}$ 538 nm \ $\lambda_{em}$ 554 nm).

TABLE 2

| Target | Assay | Primers (5' to 3') | Probe (5' to 3') | 5-plex assay conditions | Ref. |
| --- | --- | --- | --- | --- | --- |
| SMN1 | Copy number | (f) AATGCTTTTTAA-CATCCATATAAAGCT (SEQ ID NO: 1) (r) CCTTAATTTAAG-GAATGTGAGCACC (SEQ ID NO: 3) | FAM-CAGGGTTTC*AGACAAA (SEQ ID NO: 2)-MGBNFQ | 0.37 x | et ai., 2003 |
| SMN2 | Copy number | (f) AATGCTTTTTAA-CATCCATATAAGCT (SEQ ID NO: 4) (r) CCTTAATTTAAG-GAATGTGAGCACC (SEQ ID NO: 6) | FAM-TGATTTTGTCTA*AAA-CCC (SEQ ID NO: 5)-MGBNFQ | 0.76 x | Anhuf et ai., 2003 |
| BCKDHA | Copy number | (f) CAACCTACTCTT-CTCAGACGTGTA (SEQ ID NO: 7) (r) TCGAAGTGATCC-AGTGGGTAGTG (SEQ ID NO: 9) | (FAM/VIC)-CAGGAGATGCCCG-CCCAGCTC (SEQ ID NO: 8)-TAMRA | FAM: 0.18 x VIC: 0.56 x | DiMatteo et ai., 2008 |

TABLE 2-continued

| Target | Assay | Primers (5' to 3') | Probe (5' to 3') | 5-plex assay conditions | Ref. |
|---|---|---|---|---|---|
| c815A > G | SNP | (f) TGCTGATGCTTT-GGGAAGTATGTTA (SEQ ID NO: 10)<br>(r) TGTCAGGAAAAG-ATGCTGAGTGATT (SEQ ID NO: 12) | (A) (FAM/VIC)-CATGAGTGGG-CTA*TCATAC (SEQ ID NO: 11)-MGBNFQ<br>(G) FAM-ATGAGTGGCTG*TC-ATAC (SEQ ID NO: 13)-MGBNFQ: VIC-CATGA-GTGGCTG*TCATAC (SEQ ID NO: 14)-MGBNFQ | 0.9 ×<br><br>FAM: 0.9 ×<br>VIC: 0.45 × | |
| RNaseP | Copy number | Unknown | unknown | n/a | Standard product 4403326, ABI |

5-exonuclease genotyping assay design. Assay conditions in column 5 are specific to the multiplexed SMA assay. References: D. Anhuf, T. Eggermann, S. Rudnik-Schoneborn and K. Zerres, Hum Mutat., 2003, 22, 74-78; D. DiMatteo, S. Callahan and E. B. Kmiec, Exp Cell Res., 2008, 15, 878-886.

Target DNA

For some genetic targets, BCKDHA and SMN2, plasmid DNA was synthesized (GeneArt, Regensburg, Germany) containing the sequence spanning between the primers (see Table 2) and cloned into the GeneArt standard vector (2.5 kb). The target fragment was released from the cloning vector by restriction digestion with SfiI to avoid any DNA supercoiling that might affect the assay. For simplicity, these gene fragments are called "plasmid DNA" throughout the text. A string of different gene fragments was also synthesized (GeneArt) and cloned into the GeneArt standard vector for demonstration of multiplexed reactions, called an "artificial chromosome" in the text. In this case, the fragments were separated from each other by restriction digestion at flanking EcoRV sites. Human DNA was obtained in already purified form from cell lines (See Table 3; Coriell, Camden, NJ) and fragmented before use with a K7025-05 nebulizer following manufacturer's instructions (Invitrogen, Carlsbad, CA). DNA concentration was quantified by measuring absorbance at 260 nm on a Nanodrop 2000 spectrophotometer (Thermo Scientific, Wilmington, DE).

TABLE 3

Map of patient numbers used in the text to Coriell cell lines.

| Patient number | Coriell cell line | Patient number, cont'd. | Coriell cell line, cont'd. |
|---|---|---|---|
| 1 | NA14638 | 11 | NA13714 |
| 2 | NA14637 | 12 | NA13712 |
| 3 | NA14097 | 13 | NA13709 |
| 4 | NA14096 | 14 | NA13707 |
| 5 | NA14094 | 15 | NA13705 |
| 6 | NA14093 | SMA carrier | NA03814 |
| 7 | NA14092 | SMA 1 | NA03813 |
| 8 | NA14091 | SMA 2 | NA00232 |
| 9 | NA14090 | SMA 3 | NA09677 |
| 10 | NA13715 | SMA 4 | NA10684 |

Microfluidics

Microfluidic chips were manufactured by conventional soft lithography. Molding masters were fabricated by spin coating SU-8 negative photoresist (MicroChem Corp., Newton, MA) onto 6 inch silicon wafers and transferring the fluidic features from photomasks (CAD/Art Services, Bandon, OR) by contact lithography with an OAI Hybralign Series 200 aligner (OAI, San Jose, CA). Chips contained channels with two depths: deep channels with low hydrodynamic resistance (100±10 um) for transporting fluid from external ports to the functional regions of the chip, and shallow channels (20±1 um) for droplet manipulation and detection. SU-8 photoresists 2100 and 2025 were used for deep and shallow channels respectively. Polydimethylsiloxane (PDMS) (Sylgard® 184, Dow Corning, Midland, MI) chips were molded from the negative masters within mold housings of custom design. Glass cover slides were permanently bonded to the fluidic side of the chips by surface activation in an AutoGlow™ oxygen plasma system (Glow Research, Phoenix, AZ) followed by immediate contact bonding. To create hydrophobic surfaces, the microfluidic channels were exposed for ~2 min to 1H,1H,2H,2H-perfluorodecyltrichlorosilane (Alfa Aesar, Ward Hill, MA) dissolved in FC-3283 (3M Specialty Materials, St. Paul, MN) prepared as a mixture of 18 g silane in 100 uL solvent.

Two different microfluidic devices were used, one for droplet generation and the other for fluorescence readout after thermal cycling. The droplet generation chip created an emulsion of uniformly sized aqueous droplets of template DNA and PCR master mix that were suspended in an inert fluorinated oil with an emulsion stabilizing surfactant, called "carrier oil" from this point forward (REB carrier oil; RainDance Technologies, Lexington, MA). Droplets were generated in a cross-shaped microfluidic intersection, or "nozzle". As shown in FIG. 3a, under typical operation the aqueous phase flowed into the nozzle from the right (160 uL/hr), joining flows of the carrier oil from the top and bottom (750 uL/hr of total oil), and producing 4 pL droplets at a rate of 11 kHz. The channel widths at the intersection measured 15 um for the aqueous inlet, 12.5 for the oil inlets, and 15 um widening to 40 um at the outlet. Flow was driven by custom OEM pumps (IDEX Corporation, Northbrook, IL).

Approximately 25 uL of the PCR reaction mixture was collected as an emulsion from the droplet generation chip and thermally cycled in a DNA Engine (Bio-Rad, Hercules, CA). The reaction mixture contained 1× TaqMan® universal PCR master mix (Applied Biosystems, Carlsbad, CA), 0.2 mM dNTP (Takara Bio, Madison, WI), and various amounts of primer pairs and probes as described in the results. 1× assay concentration is defined as 0.2 µM probes with 0.9 µM primers. In all cases, when varied from the 1× concentration, the primers and probes were varied by the same amount. The cycler program included a 10 min hot start at 95° C., and 45 cycles of 15 sat 95° C. and 60 s at 60° C.

The droplets became concentrated during off-chip handling because the carrier oil is more dense than the aqueous phase and drained down from the emulsion. Hence the droplets were reinjected into the readout chip as a tightly packed emulsion that required dilution prior to readout to properly distinguish one droplet from another. A "spacer" nozzle similar to the droplet generation nozzle above was used to inject uniform plugs of extra carrier oil between droplets immediately before readout. As shown in FIG. 3b, the droplet entrance into the nozzle tapered down into a constriction about the size of an individual droplet forcing the droplets to enter the nozzle in single file and consequently at a stable rate. Opposed flow of the carrier oil from the top and bottom channels separated the droplets uniformly. The channel leaving the spacer nozzle increased in width along the direction of flow, and the droplets were interrogated by laser induced fluorescence at the location along the channel where the width was smaller than or equal to the droplet diameter (marked with an arrow in FIG. 3b). The nozzle dimensions were 15 um for the droplet entrance and exit, and 20 um for the oil lines.

Instrumentation

Fluorescence readout was performed by conventional epifluorescence microscopy with a custom microscope. A 20 mW, 488 nm laser source (Cyan; Picarro, Sunnyvale, CA) was expanded 2× and focused by the objective lens (20×/ 0.45 NA; Nikon, Japan) onto the microfluidic channel. Two band pass filters discriminated the fluorescence collected through the objective lens: 512/25 nm and 529/28 nm for FAM and VIC fluorophores respectively (Semrock, Rochester, NY). Fluorescence was detected by two H5784-20 photomultipliers (Hamamatsu, Japan) and was typically recorded at a 200 kHz sampling rate with a USB-6259 data acquisition card (National Instruments, Austin, TX). The data traces were smoothed by a seven-point, second-order Savitzky-Golay algorithm before subsequent analysis. Concurrent with the fluorescence read out, the droplets were imaged through the same objective lens with backside illumination from an 850 nm LED (TSHG6200; Vishay Semiconductors, Shelton, CT), a short pass filter to separate the optical paths for fluorescence detection and imaging, and a Guppy CCD camera (Allied Vision Technologies, Newburyport, MA). Droplets were imaged with short illumination pulses (5-20 us) to avoid image streaking.

Data Analysis

Data was analyzed with custom LabView software (National Instruments, Austin, TX) that interpreted droplet events as contiguous bursts of fluorescence intensity above a threshold value. The signal-to-noise ratio was generally quite high and the signal levels were consistent from day to day, hence a fixed threshold value of 50 mV was used predominantly, otherwise the threshold was set by eye. The peak fluorescence intensity was recorded for each droplet event for both VIC and FAM fluorophores. Some coalescence of droplets did occur during thermal cycling, typically as isolated events between two intact droplets forming "doublets." Doublets and the rare larger coalesced events were easily filtered from the data set on based on the duration of the fluorescence burst.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A method for detecting target nucleic acid sequences in a sample, the method comprising:
    (a) partitioning a sample comprising a plurality of nucleic acid molecules comprising one or more target nucleic acid sequences into compartments, wherein a plurality of the compartments each comprise one target nucleic acid sequence, amplification reagents comprising a plurality of primer pairs, and a plurality of detectably labeled probes, and wherein each primer pair is specific to amplify a different target nucleic acid sequence and each detectably labeled probe is specific for a different target nucleic acid sequence, wherein the plurality of detectably labeled probes include:
        a first probe specific for a first target of the one or more target nucleic acid sequences, wherein the first probe includes a first fluorophore and is present at a first concentration, and
        a second probe specific for a second target of the one or more target nucleic acid sequences, wherein the second probe includes the first fluorophore and is present at a second concentration different from the first concentration;
    (b) amplifying target nucleic acid sequences in one or more of the compartments to generate fluorescence at a first fluorescent intensity from compartments that contain the first target due to the first concentration of the first probe and to generate the fluorescence at a second fluorescent intensity, different from the first fluorescent intensity, from compartments that contain the second target due to the second concentration of the second probe; and
    (c) detecting the first fluorescent intensity and the second fluorescent intensity to detect presence or absence of each of the first and second targets in the sample.

2. The method of claim 1, wherein the first fluorophore is selected from the group consisting of coumarin, FAM, VIC, ROX, an Atto dye, a fluorescein derivative, HEX, Texas Red, Cy5, and Cy5.5.

3. The method of claim 1, wherein the detecting step creates a 2D plot of fluorescence intensities from the first fluorophore and a second fluorophore from the detectably labeled probes.

4. The method of claim 3, wherein one or both of the first and the second fluorophore are selected from the group consisting of FAM, VIC, ROX, an Atto dye, a fluorescein derivative, coumarin, Texas Red, HEX, Cy5, and Cy5.5.

5. The method of claim 3, wherein each of the target nucleic acid sequences forms a distinct cluster on the 2D plot.

6. The method of claim 1, wherein the sample is partitioned into the compartments at limiting dilution.

7. The method of claim 1, wherein the amplifying and detecting steps comprise digital PCR.

8. The method of claim 1, wherein the compartments are microwells.

9. The method of claim 1, wherein the detecting step is performed using a microscope, photomultiplier tube, a CCD camera, or a photodiode.

10. The method of claim 1, wherein at least two fluorophores from the detectably labeled probes are used for multiplex detection of the target nucleic acid sequences.

11. The method of claim 1, wherein the compartments are not droplets.

12. The method of claim 1, wherein the compartments are containers.

13. The method of claim 1, wherein one or more of the detectably labeled probes are labeled with a fluorophore selected from the group consisting of FAM, VIC, ROX, an Atto dye, a fluorescein derivative, coumarin, Texas Red, HEX, Cy5, and Cy5.5.

* * * * *